US011510936B2

(12) United States Patent
Girault et al.

(10) Patent No.: US 11,510,936 B2
(45) Date of Patent: Nov. 29, 2022

(54) METHODS AND PHARMACEUTICAL COMPOSITION FOR THE TREATMENT OF NEURODEGENERATIVE DISEASE

(71) Applicants: INSERM (INSTITUT NATIONAL DE LA SANTÉ ET DE LA RECHERCHE MÉDICALE), Paris (FR); SORBONNE UNIVERSITÉ, Paris (FR); UNIVERSITAT DE BARCELONA, Barcelona (ES)

(72) Inventors: Jean-Antoine Girault, Paris (FR); Albert Giralt, Paris (FR); Veronica Ines Brito, Barcelona (ES); Silvia Gines, Barcelona (ES)

(73) Assignees: INSERM, Paris (FR); SORBONNE UNIVERSITE, Paris (FR); UNIVERSITAT DE BARCELONA, Barcelona (ES)

( * ) Notice: Subject to any disclaimer, the term of this patent is extended or adjusted under 35 U.S.C. 154(b) by 325 days.

(21) Appl. No.: 16/496,738

(22) PCT Filed: Mar. 23, 2018

(86) PCT No.: PCT/EP2018/057462
§ 371 (c)(1),
(2) Date: Sep. 23, 2019

(87) PCT Pub. No.: WO2018/172527
PCT Pub. Date: Sep. 27, 2018

(65) Prior Publication Data
US 2020/0316102 A1    Oct. 8, 2020

(30) Foreign Application Priority Data

Mar. 24, 2017 (EP) .................................... 17305340

(51) Int. Cl.
| | |
|---|---|
| *C07H 21/04* | (2006.01) |
| *A61K 31/713* | (2006.01) |
| *C12N 9/12* | (2006.01) |
| *C12N 15/86* | (2006.01) |
| *A61K 48/00* | (2006.01) |

(52) U.S. Cl.
CPC .......... *A61K 31/713* (2013.01); *A61K 48/005* (2013.01); *C12N 9/12* (2013.01); *C12N 15/86* (2013.01); *C12Y 207/10002* (2013.01)

(58) Field of Classification Search
CPC .............................. A61K 31/713; C12N 15/86
See application file for complete search history.

(56) References Cited

U.S. PATENT DOCUMENTS

2005/0148650 A1    7/2005 Ohkawa

FOREIGN PATENT DOCUMENTS

WO    2005/02573 A2    1/2005

OTHER PUBLICATIONS

Kimura et al. (Nerual Regeneration Research, 17, 4, 2022, 785-787).*
Dayton et al. (Expert Opinion on Biological Therapy), 2012, 12(6), 757-766.*
Takahashi Tetsuya et al: "Identification and characterization of a novel Pyk2/related adhesion focal tyrosine kinase-associated protein that inhibits alpha-synuclein phosphorylation", Journal of Biological Chemistry, vol. 278, No. 43, Oct. 24, 2003, pp. 42225-42233.
Li Ya-Qing et al: "Common variant in PTK2B is associated with late-onset Alzheimer's disease: A replication study and meta-analyses", Neuroscience Letters, vol. 621, May 2016, pp. 83-87.
Dourlen P et al: "Functional screening of Alzheimer risk loci identifies PTK2B as an in vivo modulator and early marker of Tau pathology", Moledular Psychiatry, Apr. 26, 2016.
Giralt Albert et al: "Phyk2 is essential for astrocytes mobility following brain lesion", GLIA, vol. 64, No. 4, Apr. 2016, pp. 620-634.
Beck Tim N et al: "Adaptors for disorders of the brain? The cancer signaling proteins NEDD9, CASS4, and PTK2B in Alzheimer's disease", ONCOSCIENCE 2014, vol. 1, No. 7.

* cited by examiner

*Primary Examiner* — Amy H Bowman
(74) *Attorney, Agent, or Firm* — WCF IP

(57) ABSTRACT

In the present invention it is shown that the inactivation of the Pyk2 gene does not alter hippocampal development but prevents hippocampal-dependent memory tasks and LTP. Inventors clearly provide evidence for multiple roles of Pyk2 in spine morphology and postsynaptic structure. Thus, the inventors used direct overexpression of PYK2 by AAV-mediated gene transfer into the brain of Huntington's and Alzheimer's mouse models and found that overexpression of PYK2 in these 2 models improves synaptic properties and spine density deficits which is also accompanied by a rescue of spatial memory. Accordingly it was demonstrated that PYK2 may restore cognitive functions in neurodegenerative diseases. Thus the present invention relates to methods and pharmaceutical compositions for the treatment of neurodegenerative disease. In particular the present invention relates to a method of treating neurodegenerative disease in a subject in need thereof comprising administering to the subject a therapeutically effective amount of a vector which comprises a nucleic acid molecule encoding for PYK2 polypeptide.

Figure 1:
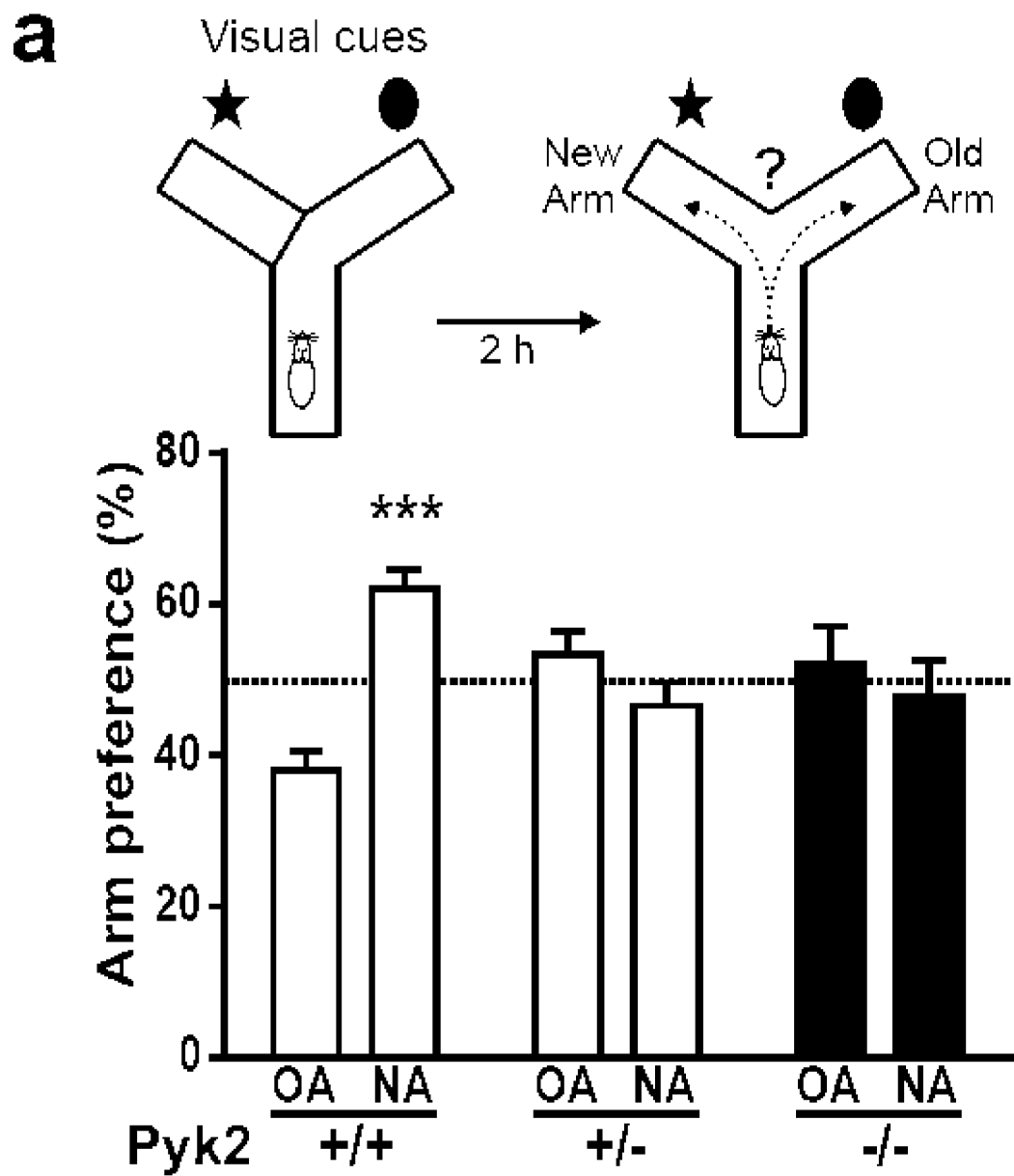

11 Claims, 35 Drawing Sheets
Specification includes a Sequence Listing.

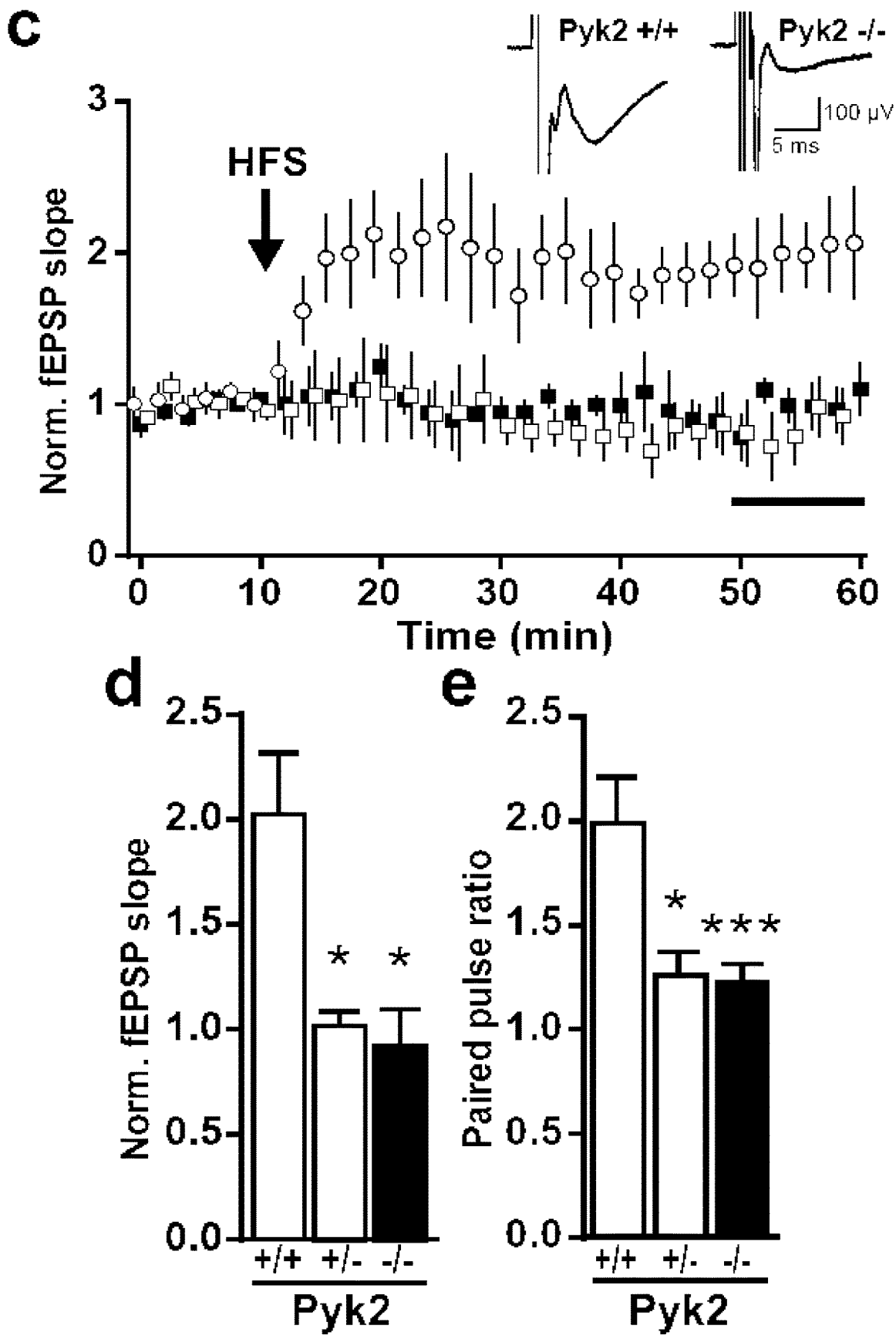
Figure 1C, D and E

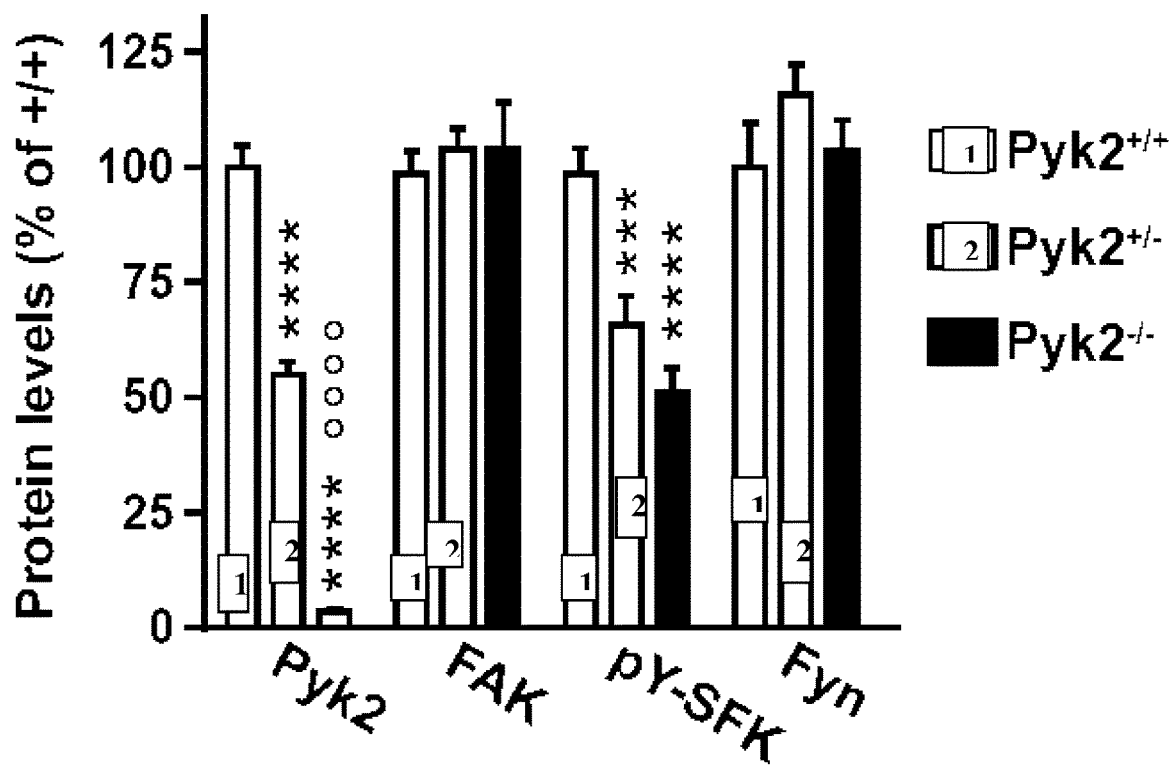
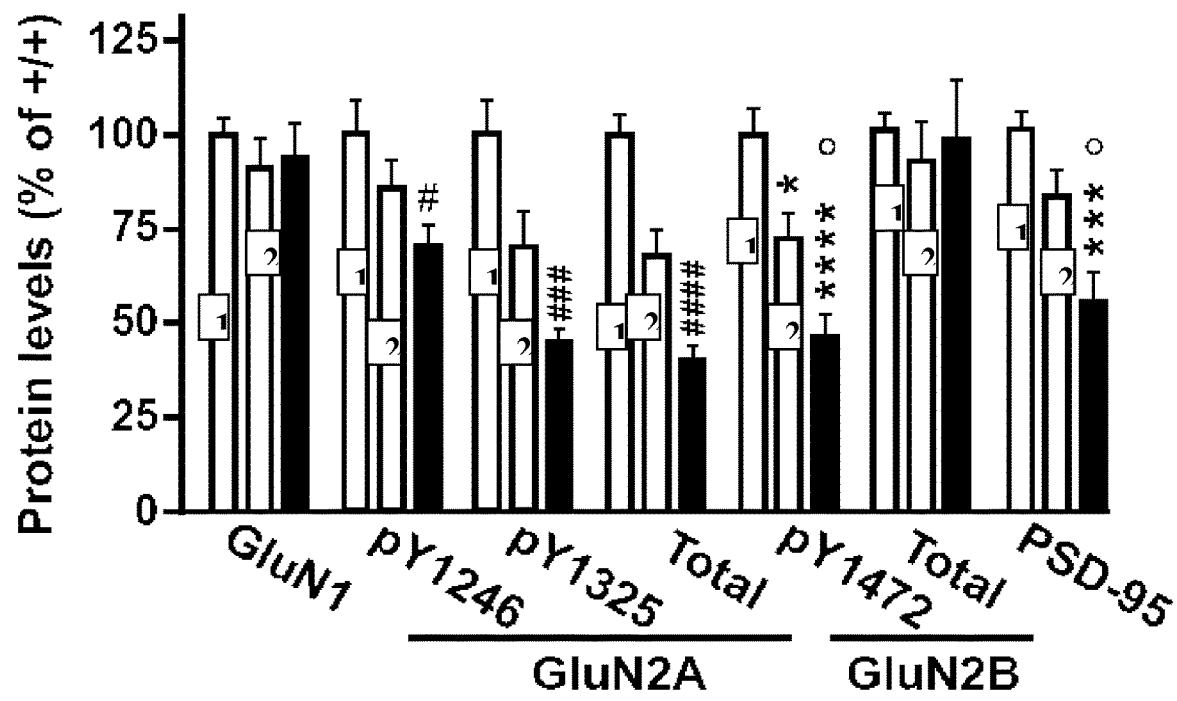
Figure 2A and B

A
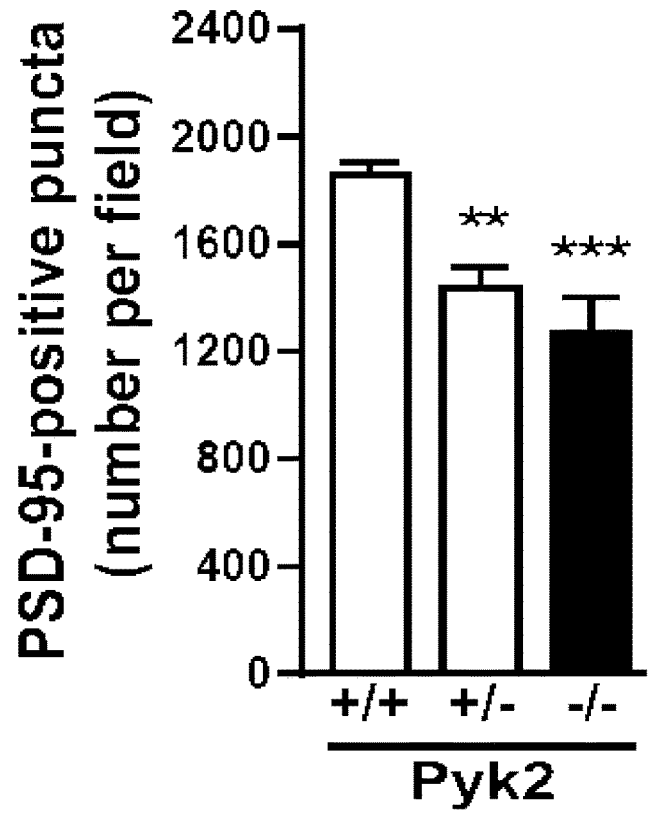
B
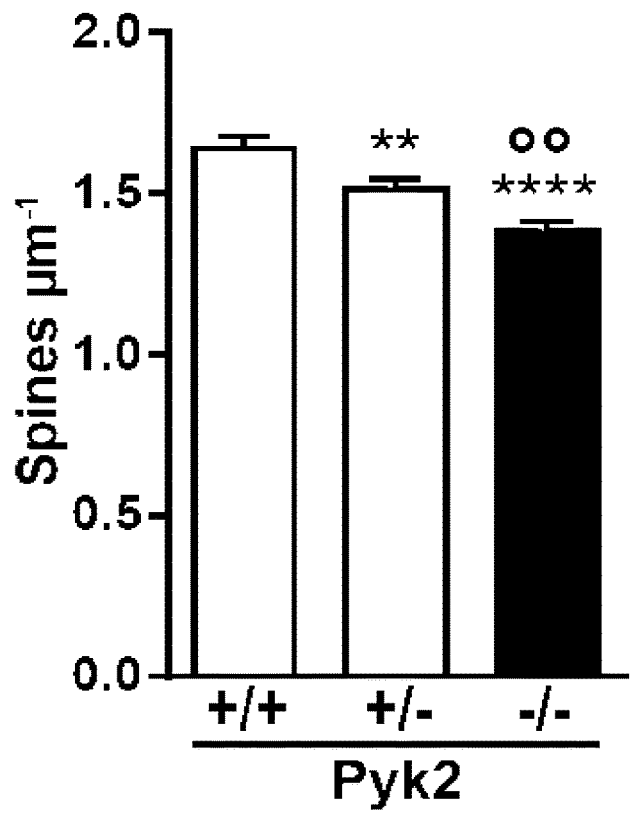
Figure 3A and B

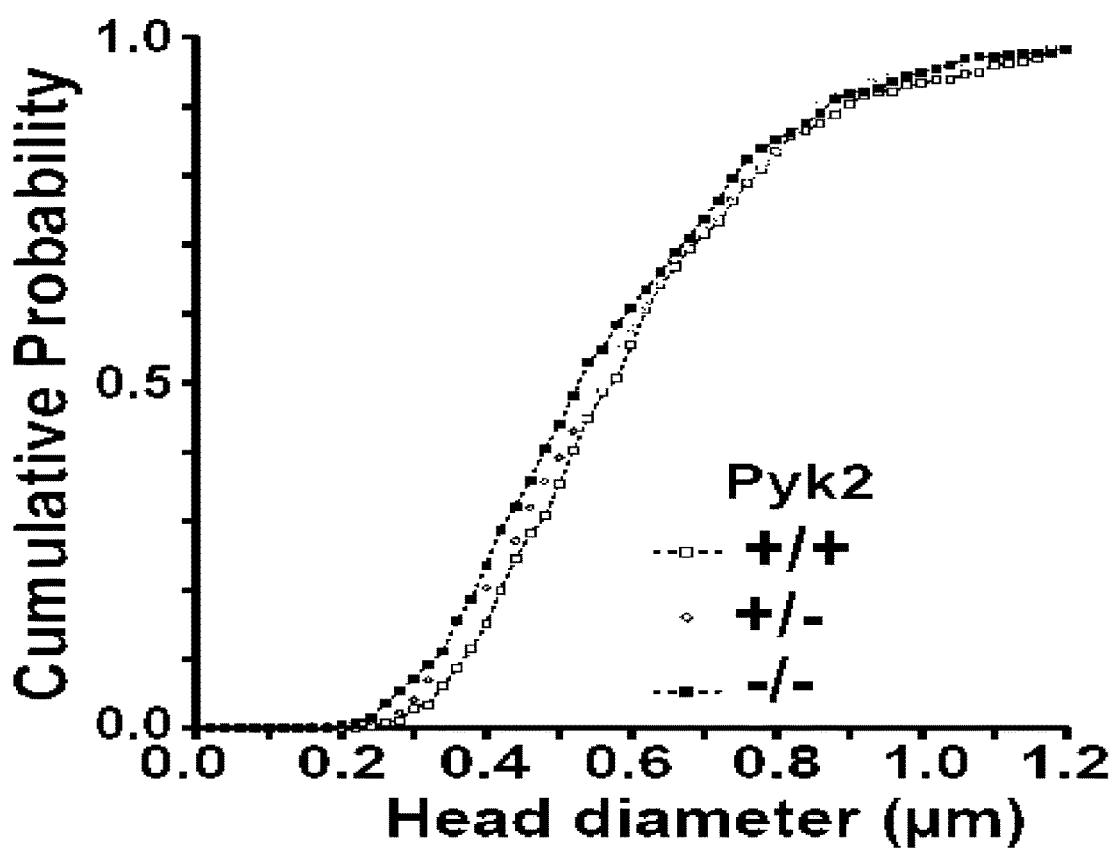
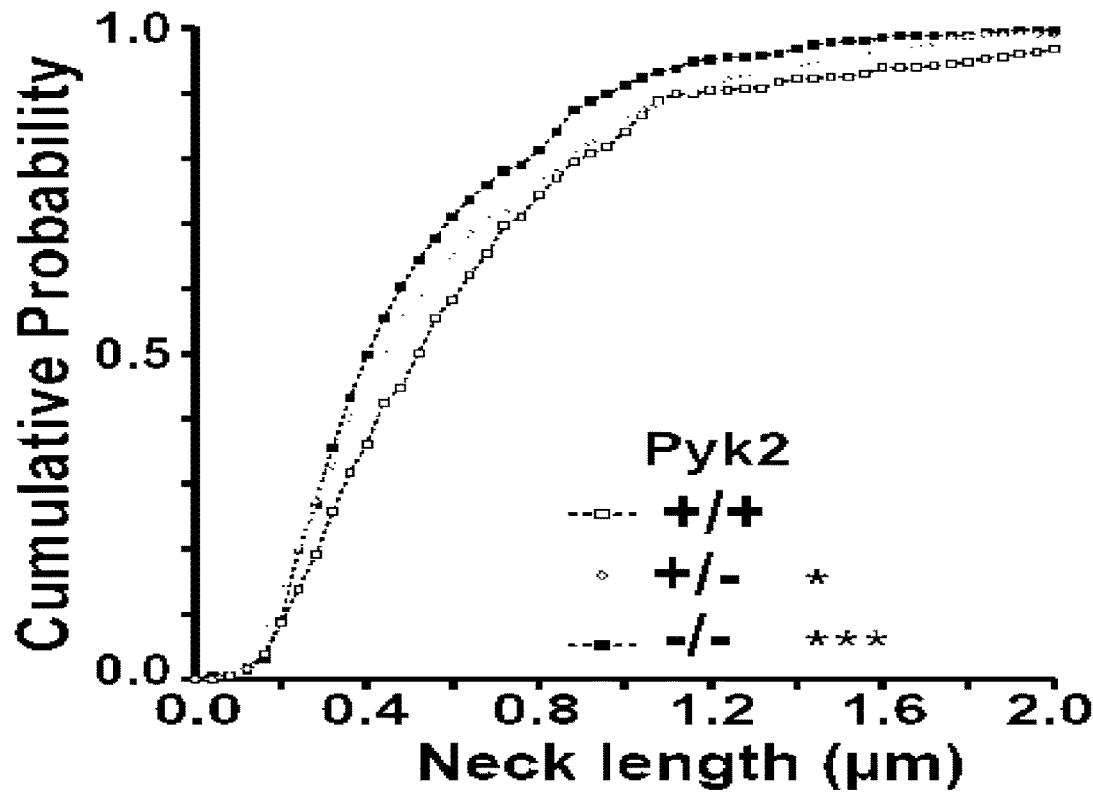
Figure 3C and D

A
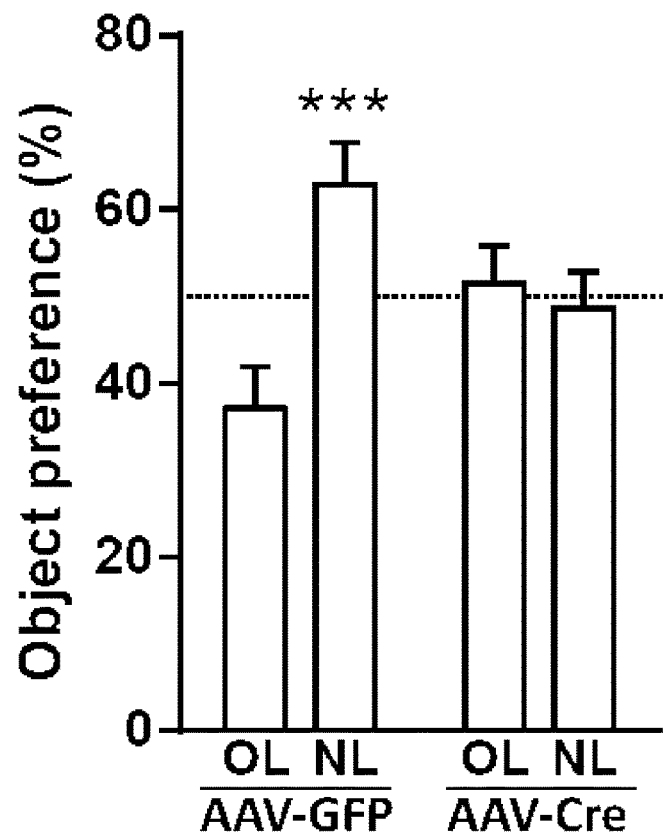
B
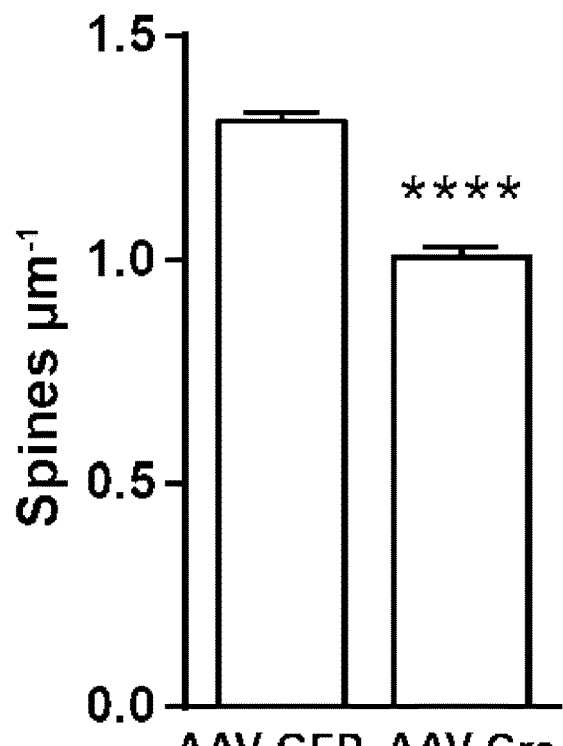
Figure 4A and B

A
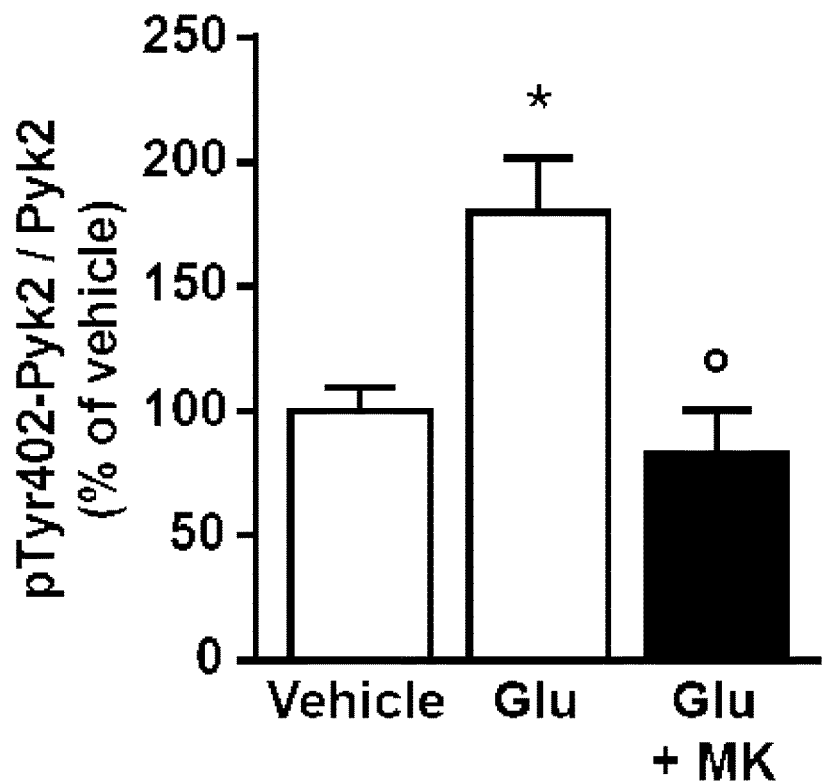
B
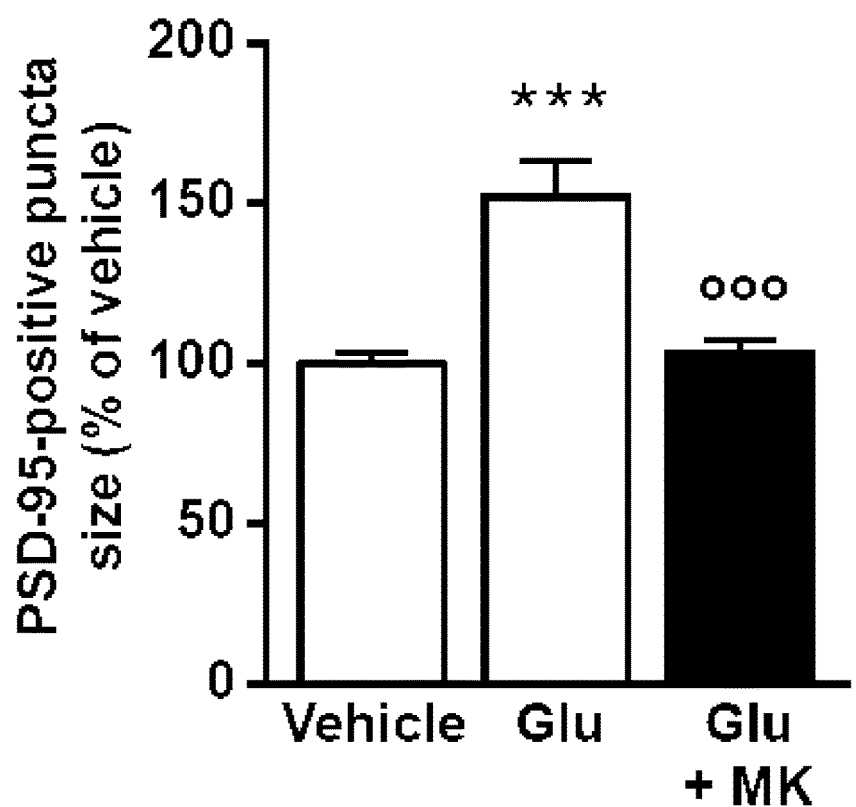
Figure 5A and B

B
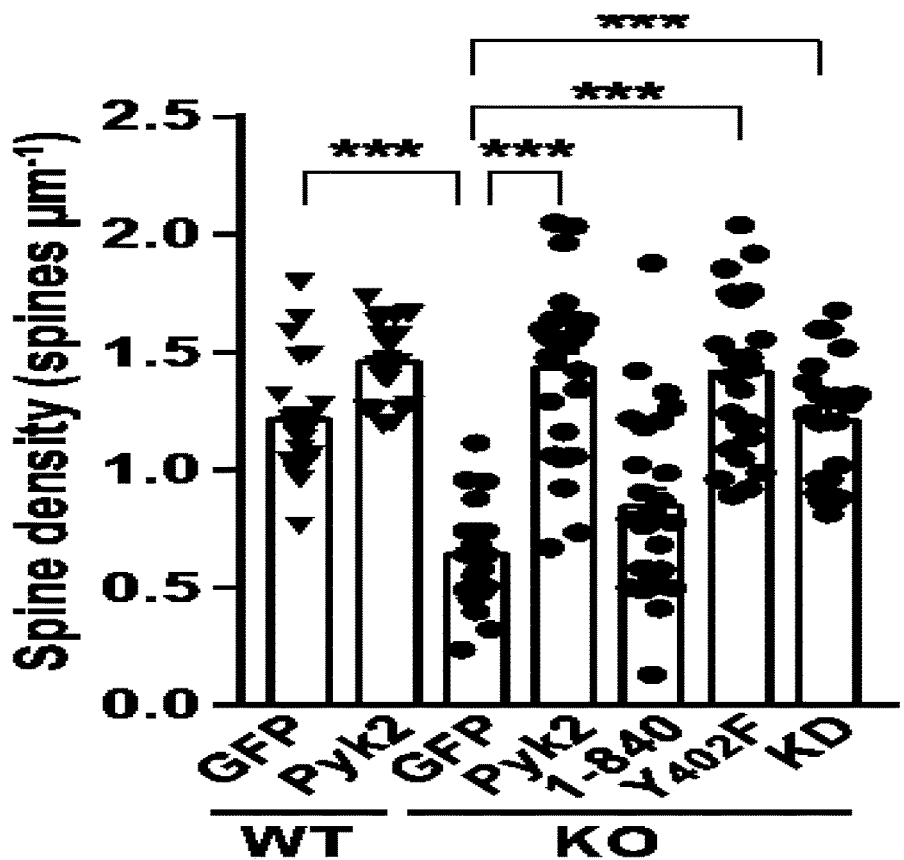
C
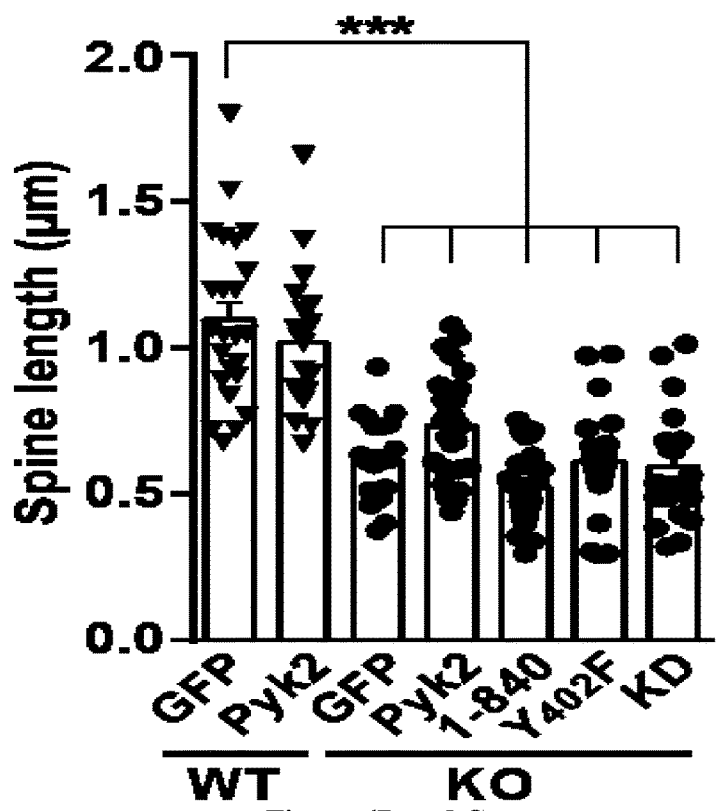
Figure 6B and C

A
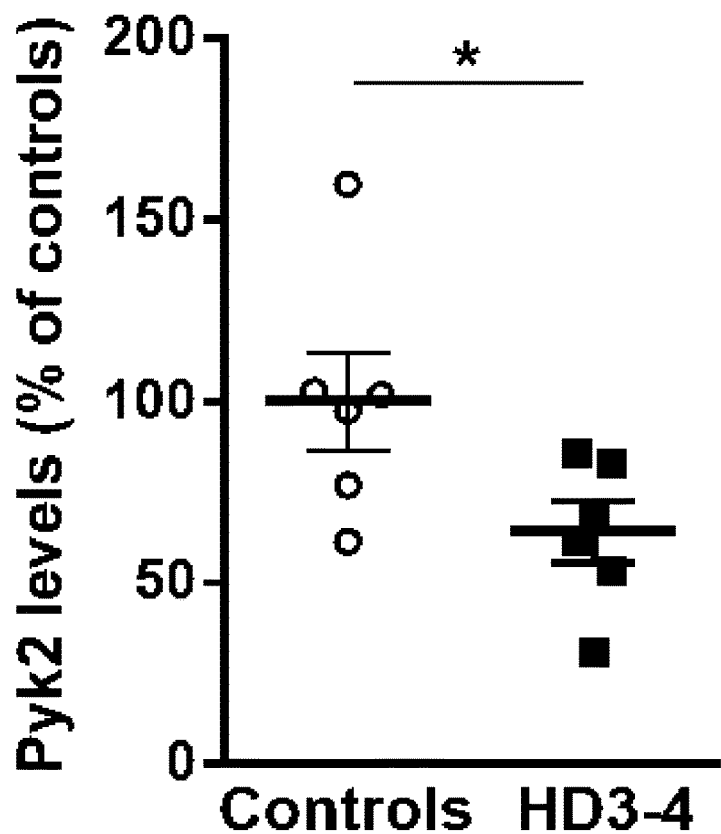
B
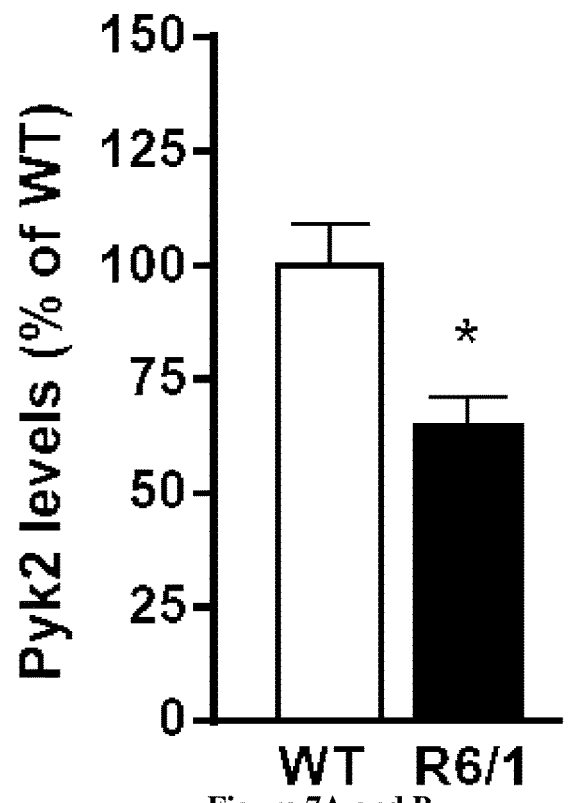
Figure 7A and B

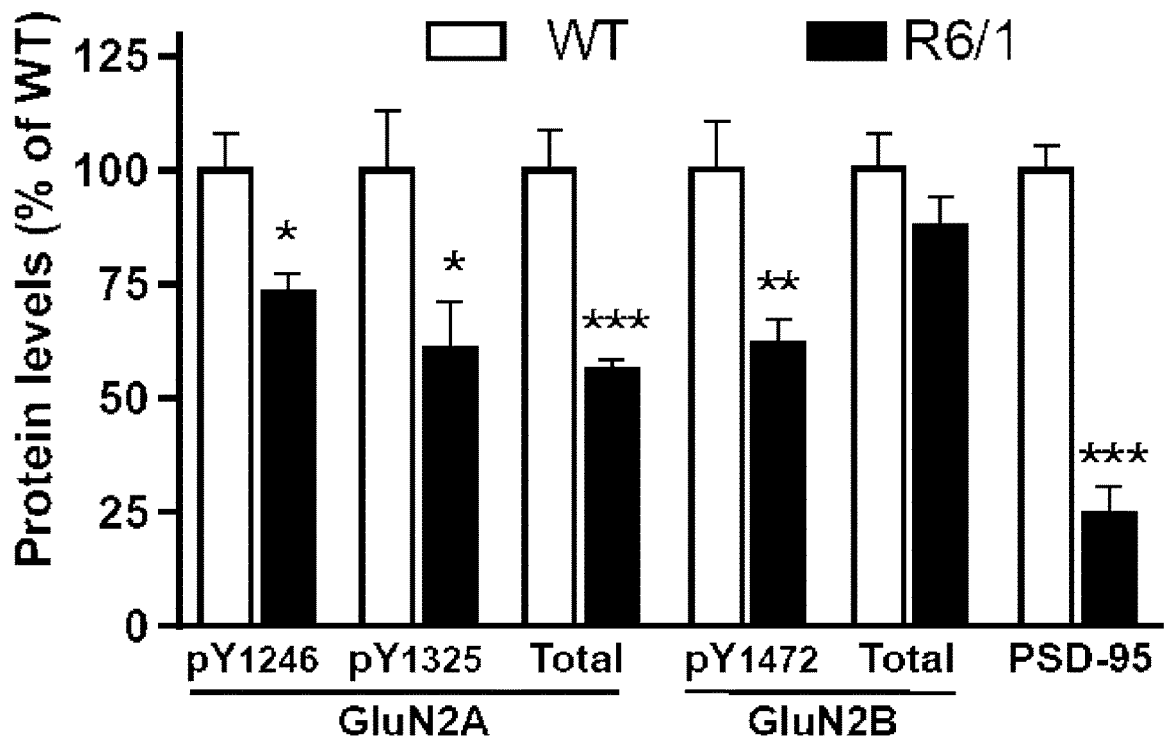
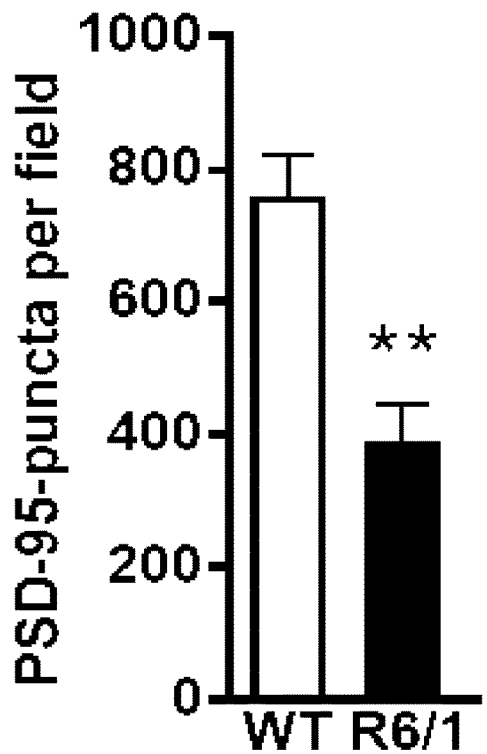
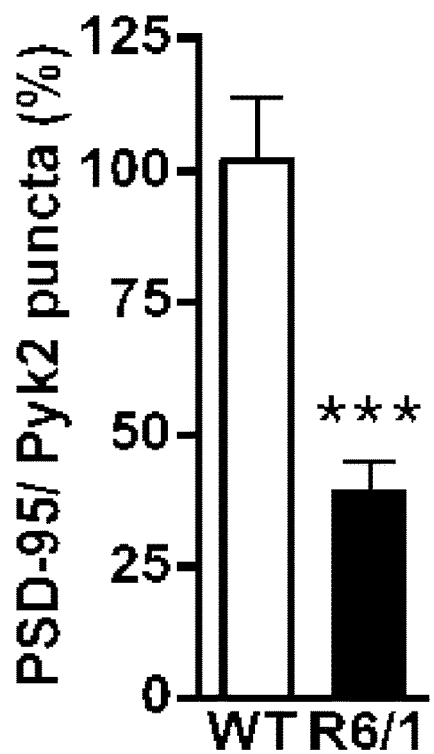
Figure 7C, D and E

A
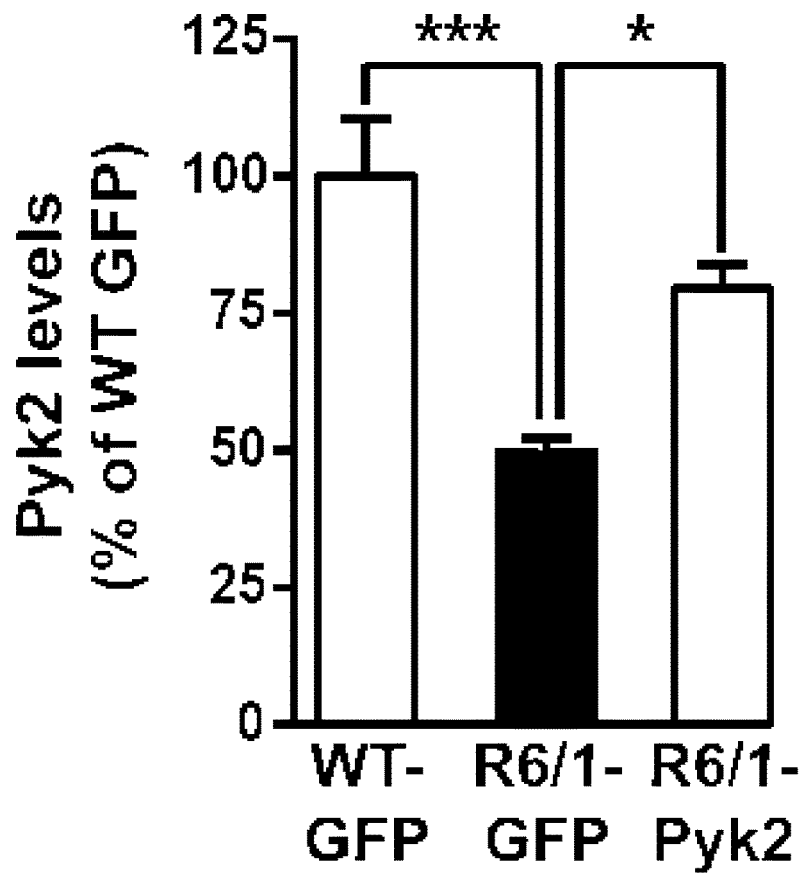
B
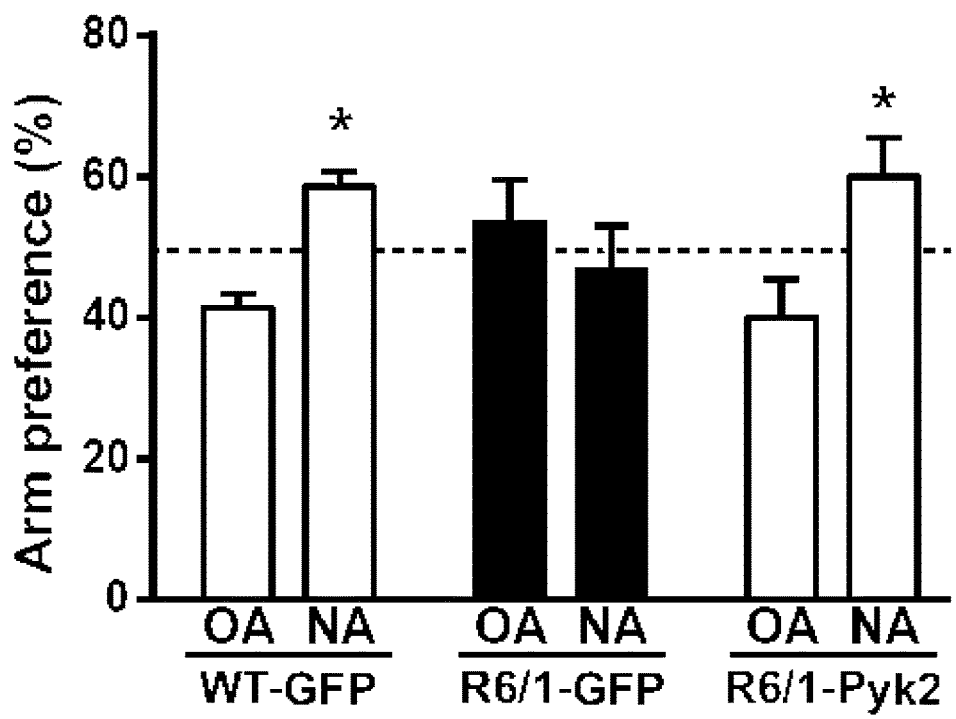
Figure 8A and B

C
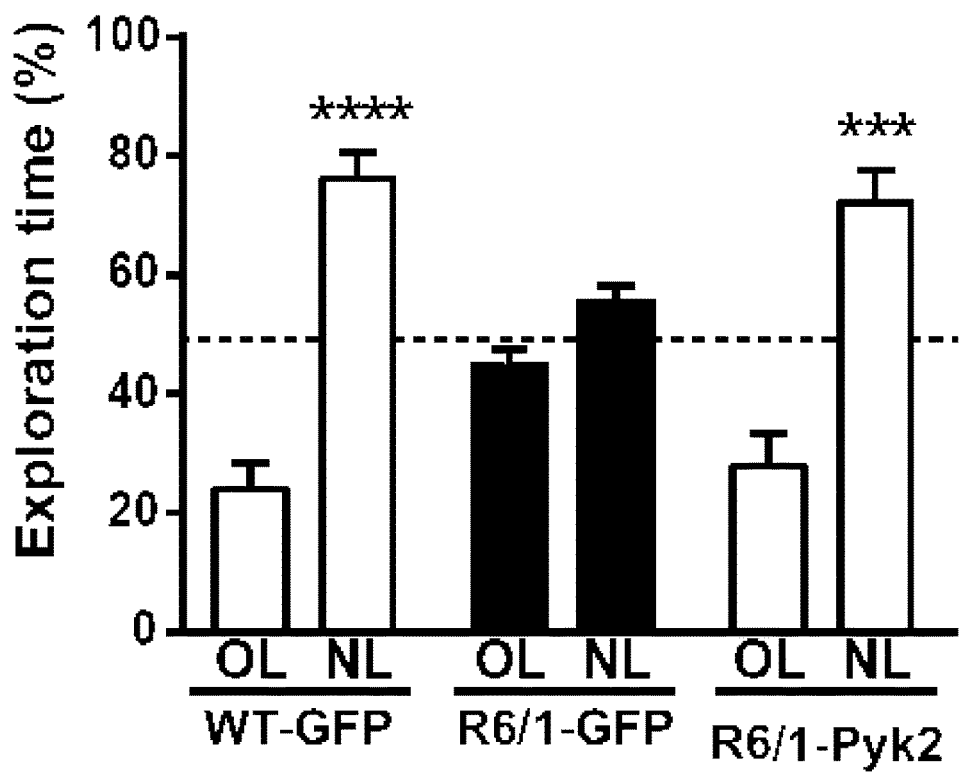
D
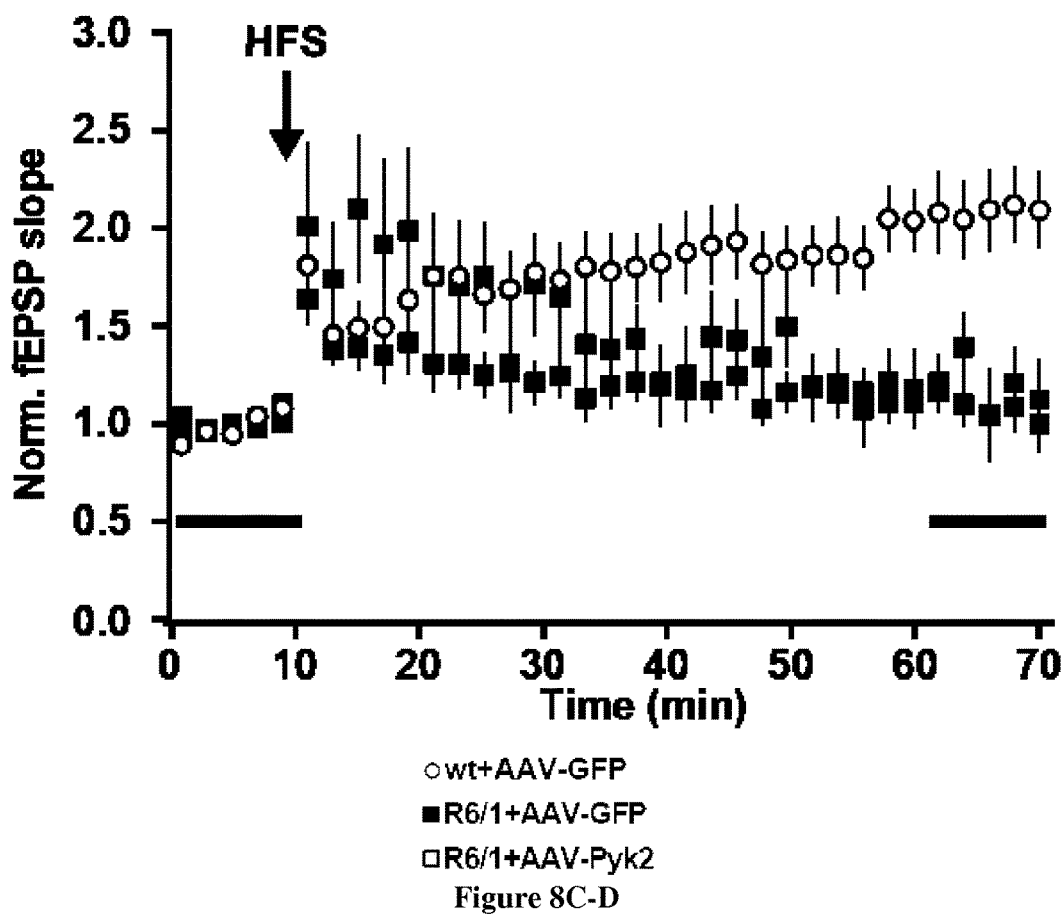
Figure 8C-D

E
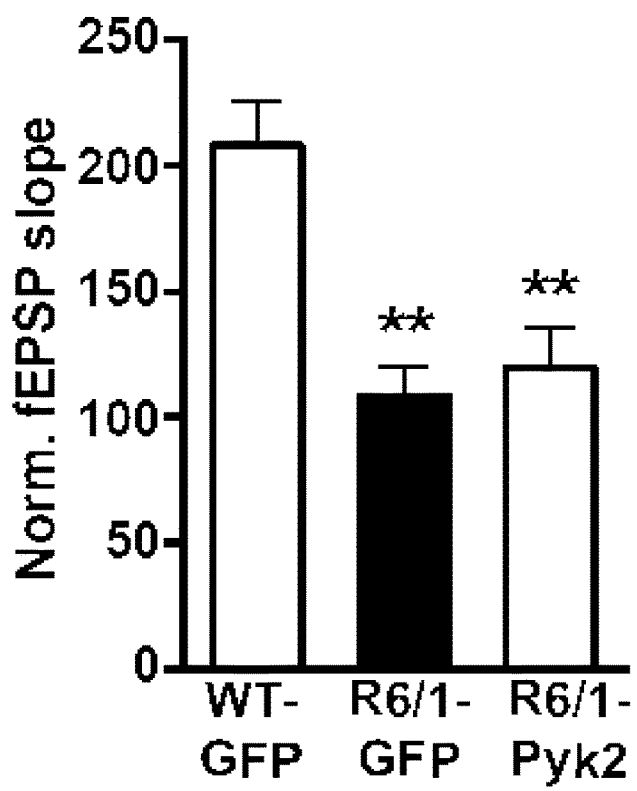
F
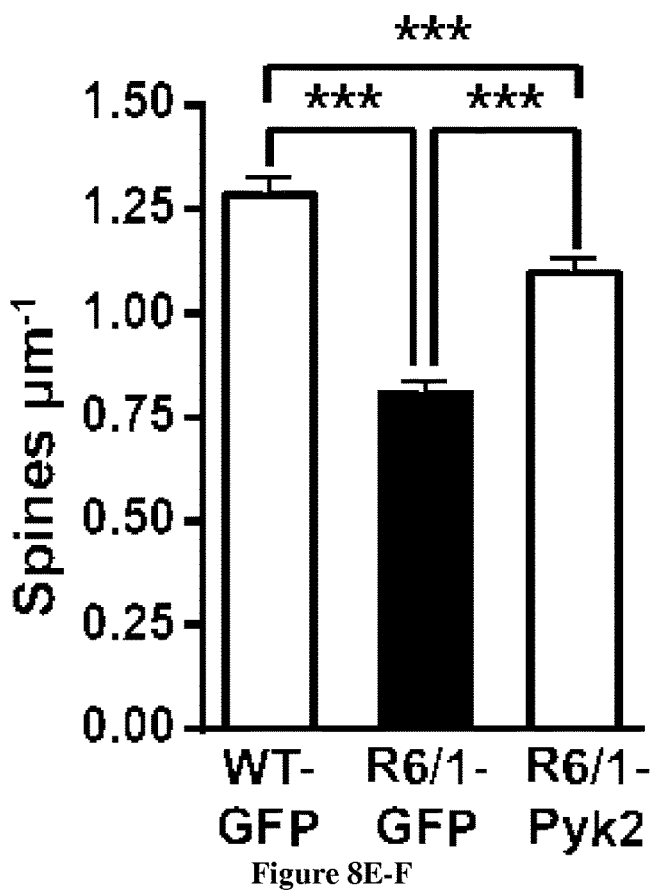
Figure 8E-F

G
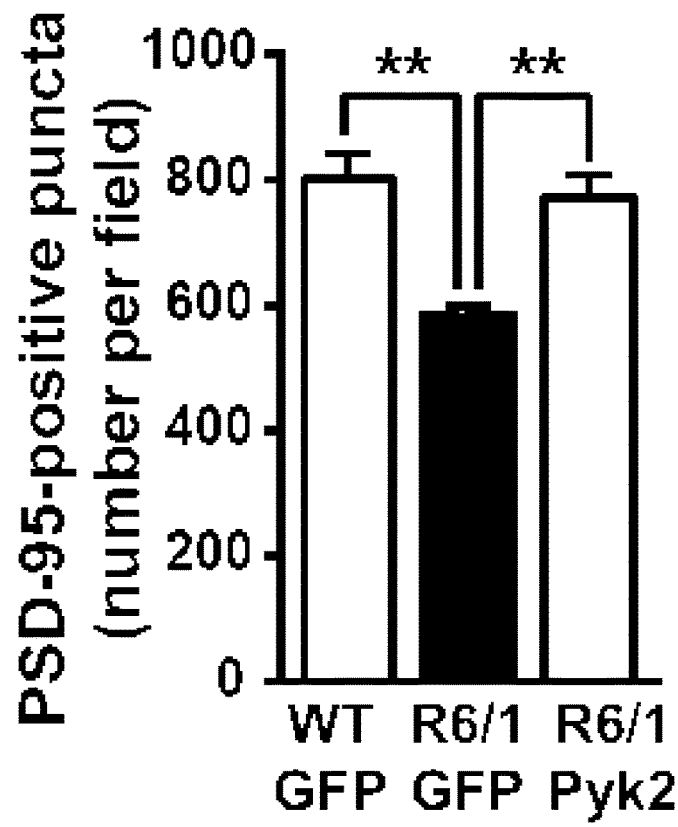
H
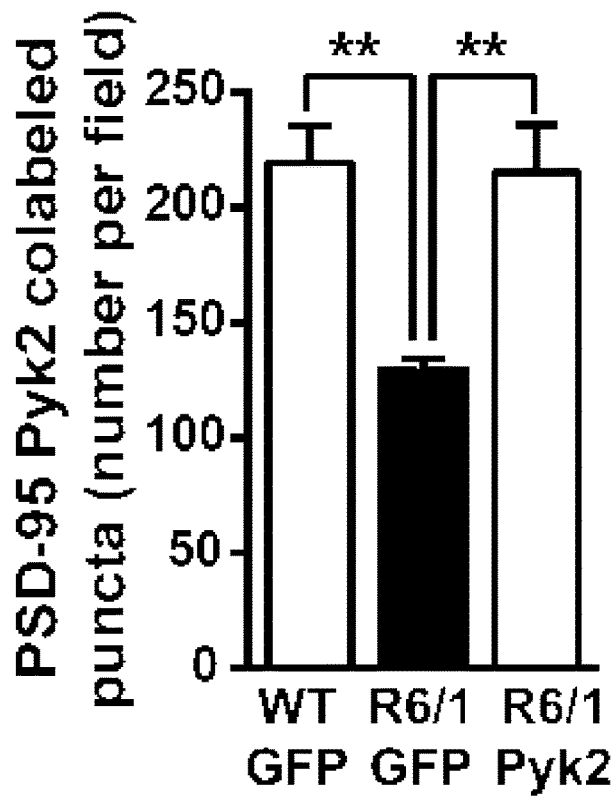
Figure 8G-H

A
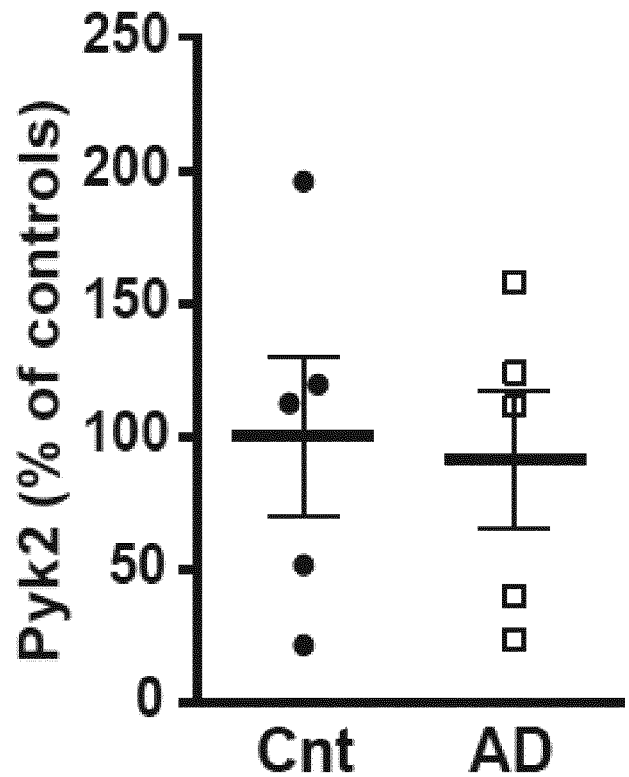
B
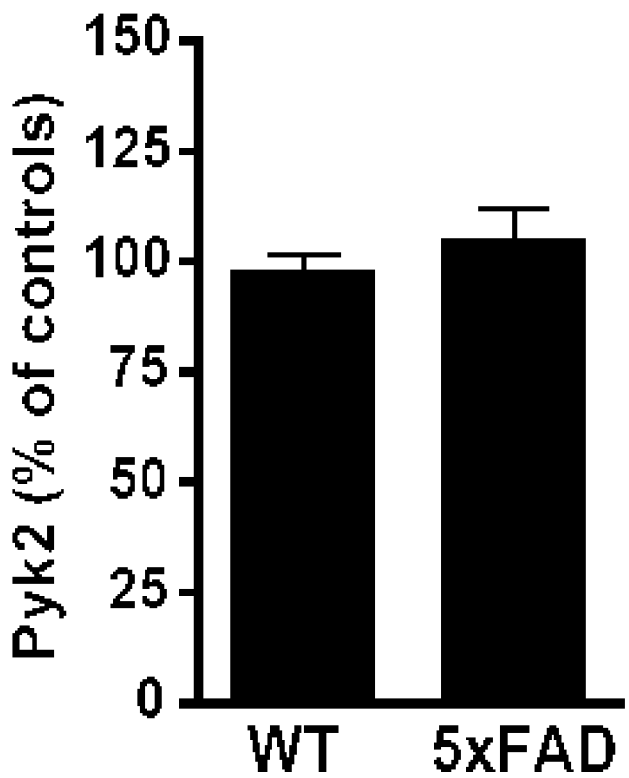
Figure 9A-B

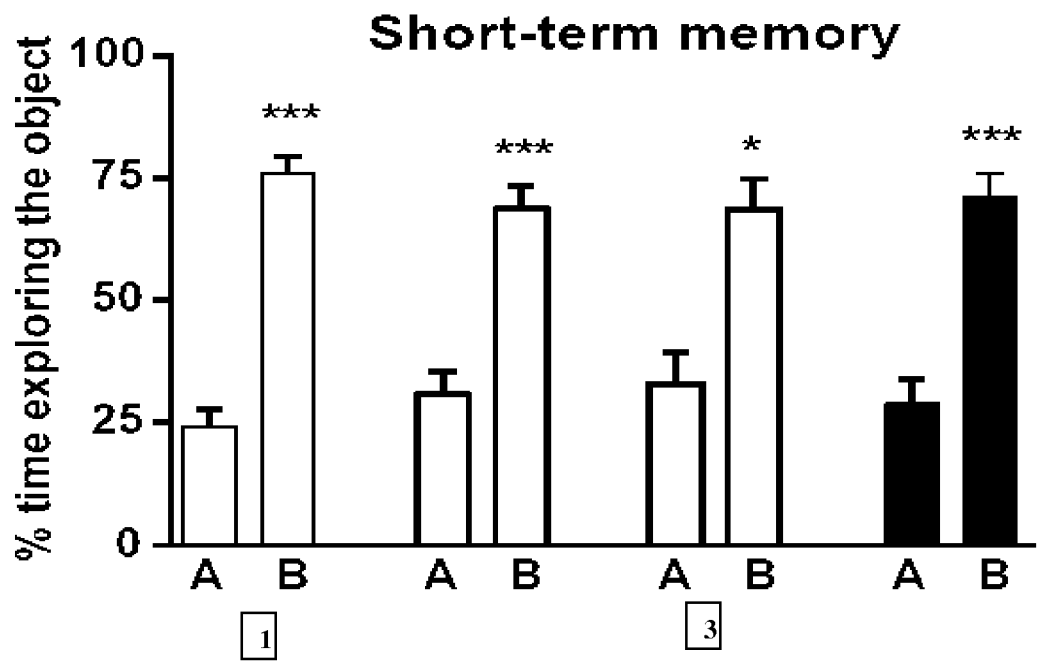
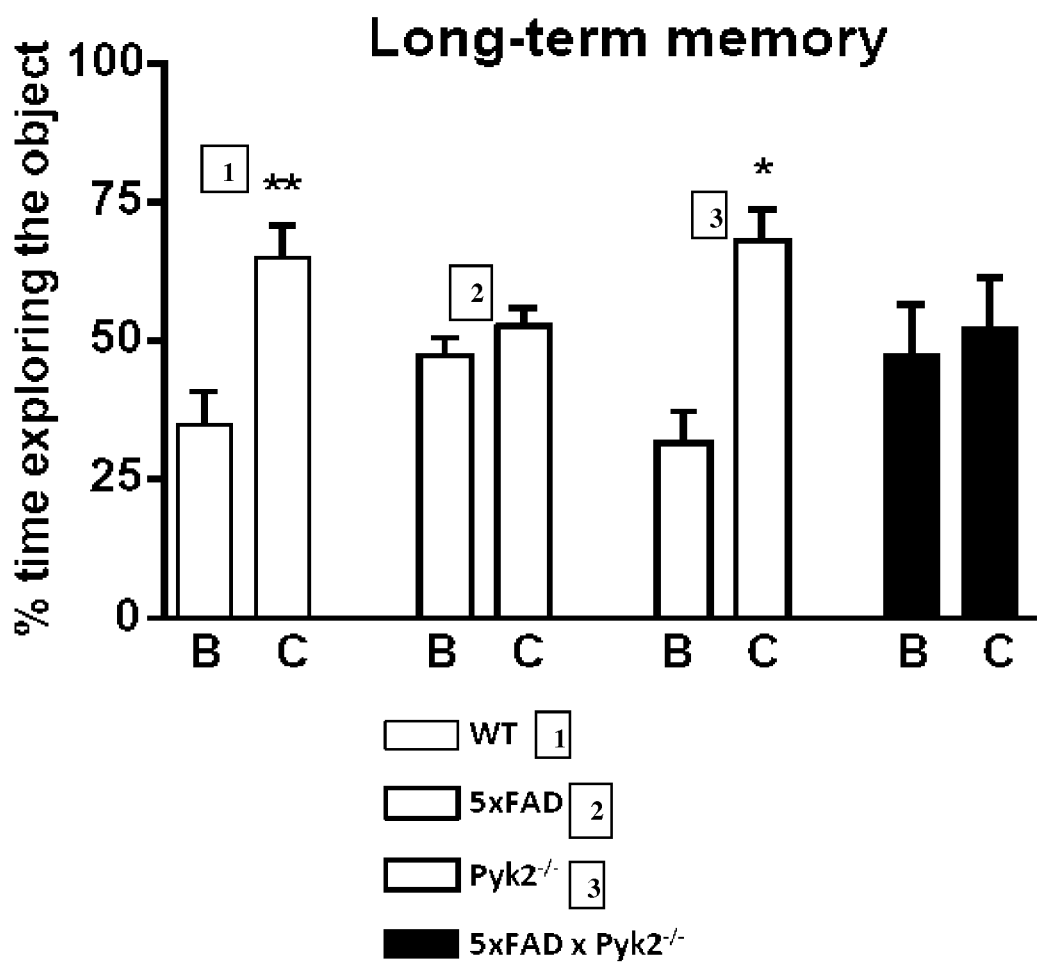
Figure 10B-C

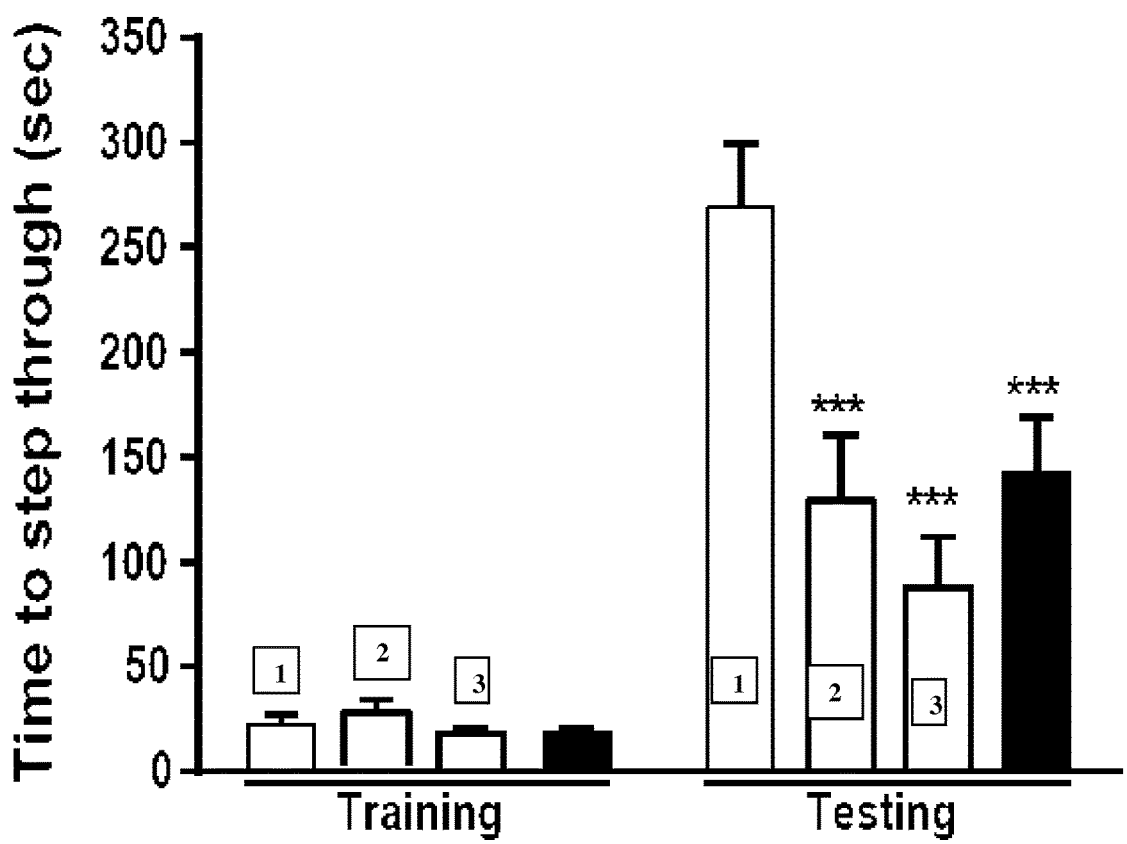
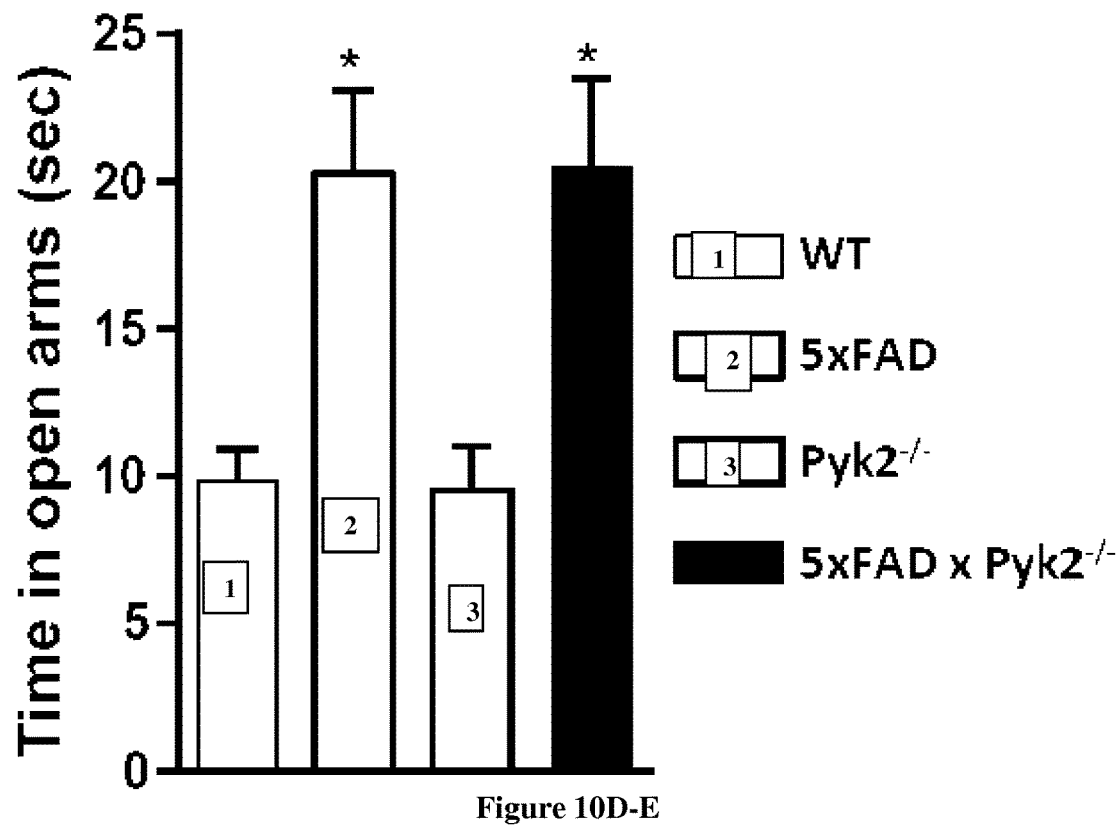
Figure 10D-E

A
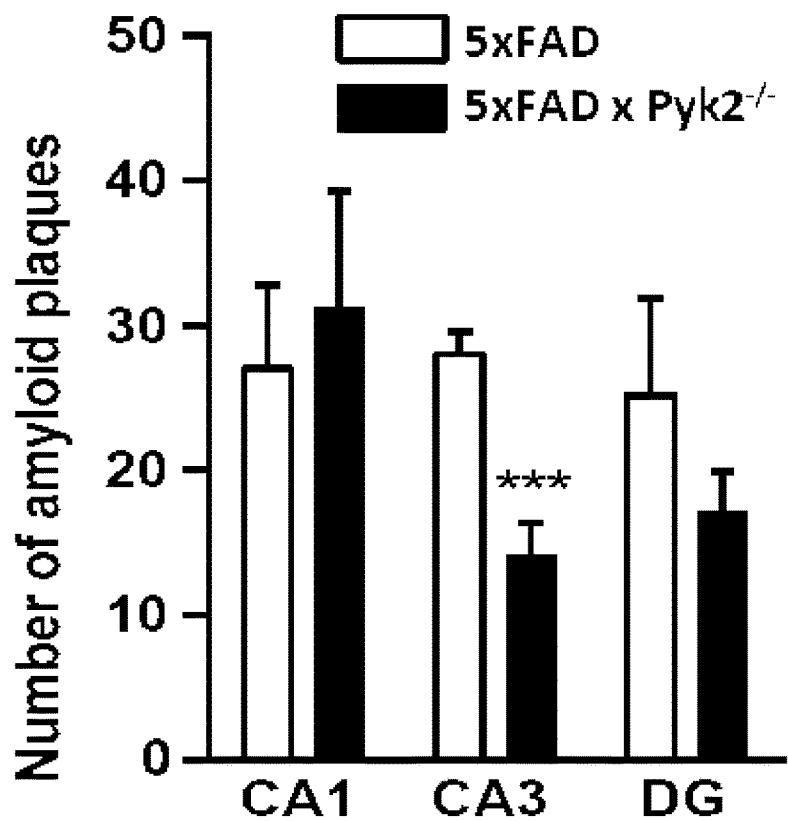
B
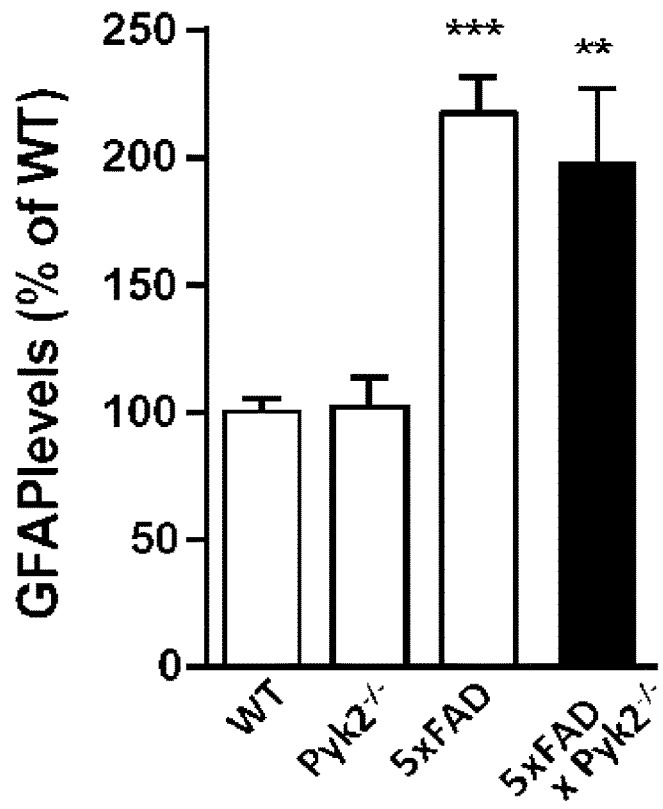
Figure 11A-B

A
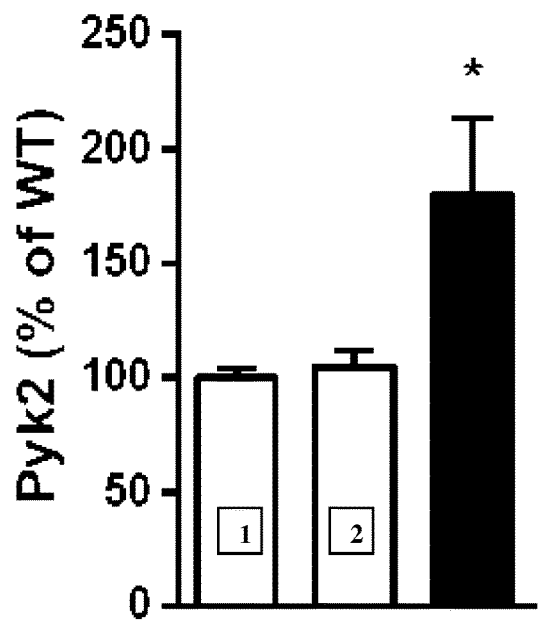
B
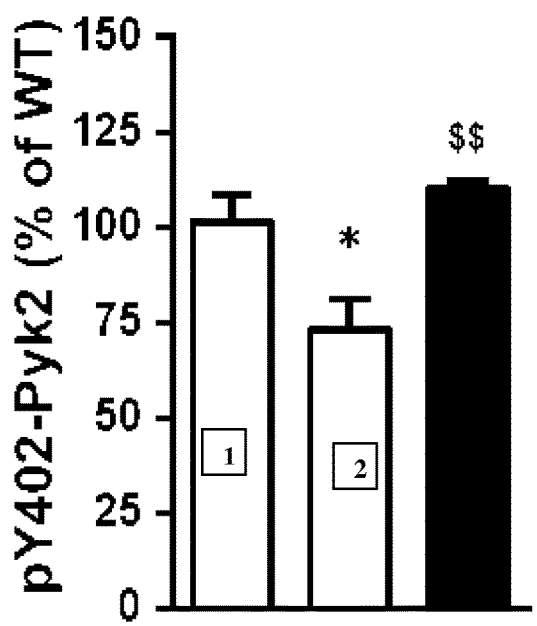
☐₁ WT/GFP  ☐₂ 5XFAD/GFP  ■ 5XFAD/Pyk2
Figure 12A-B

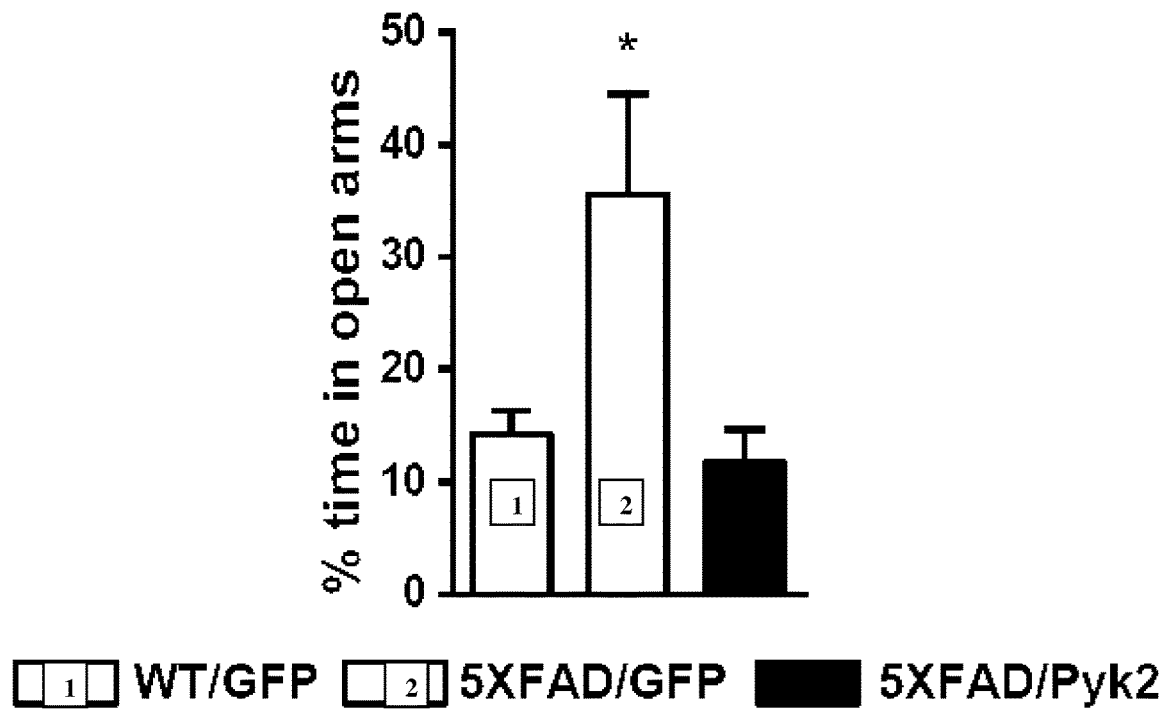
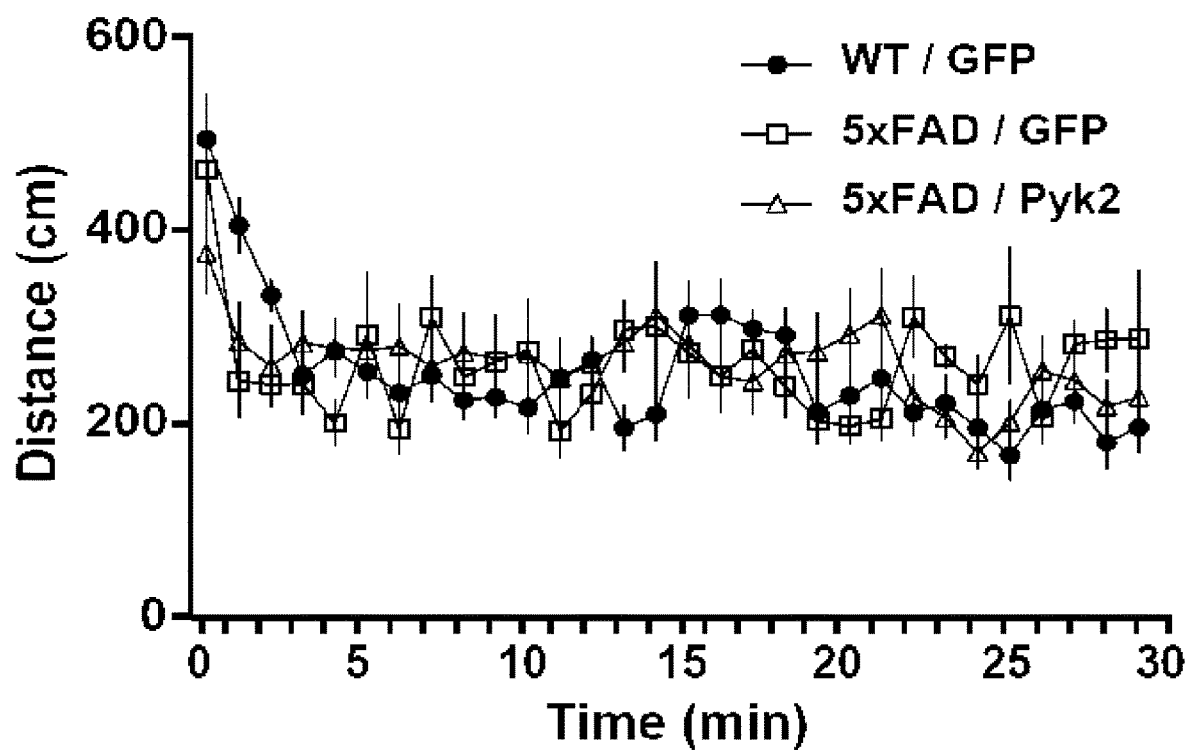
Figure 12C-D

F
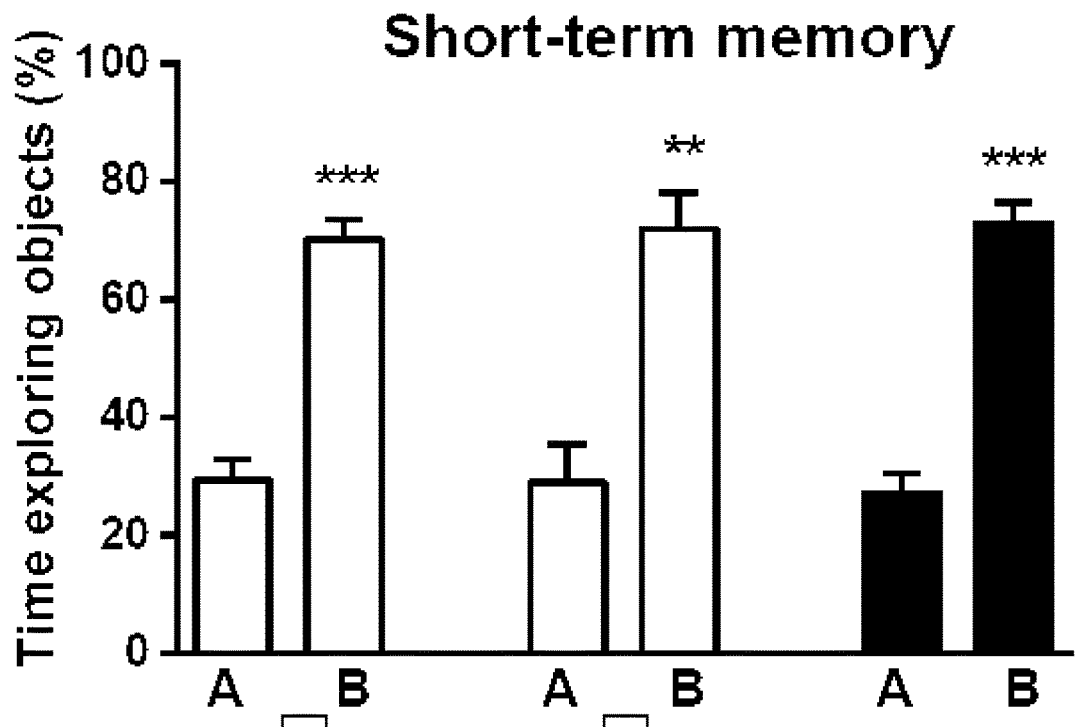
G
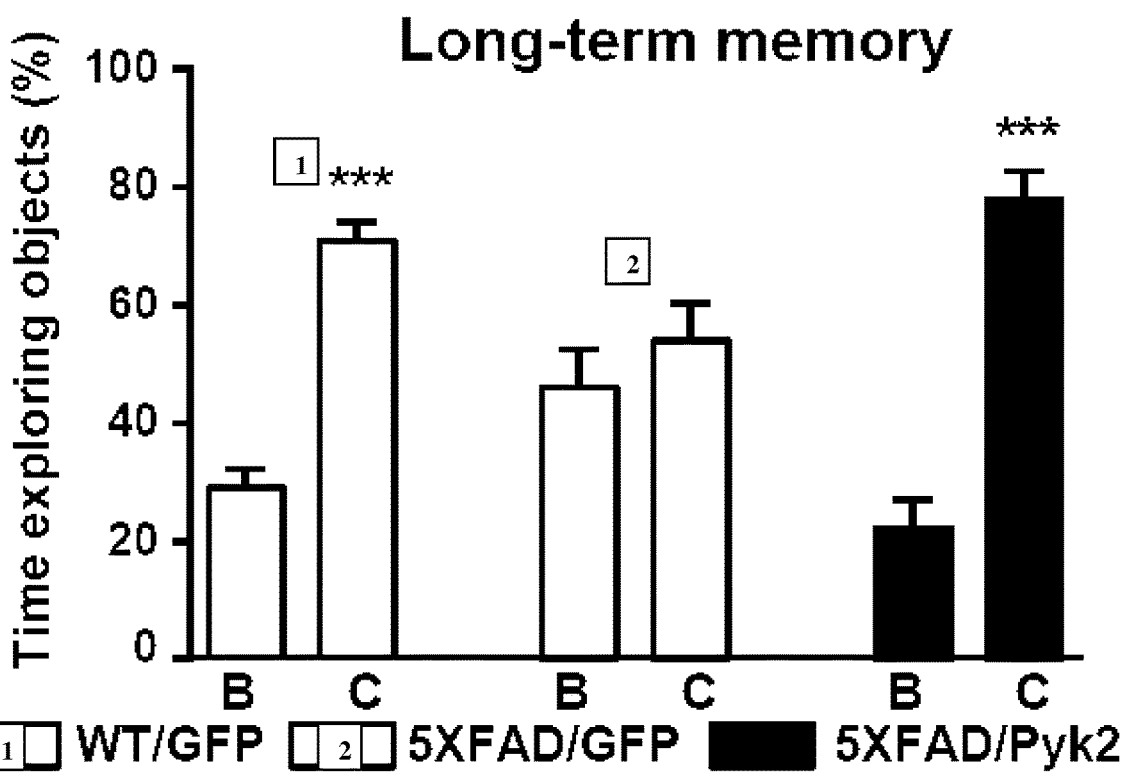
Figure 12F-G

A
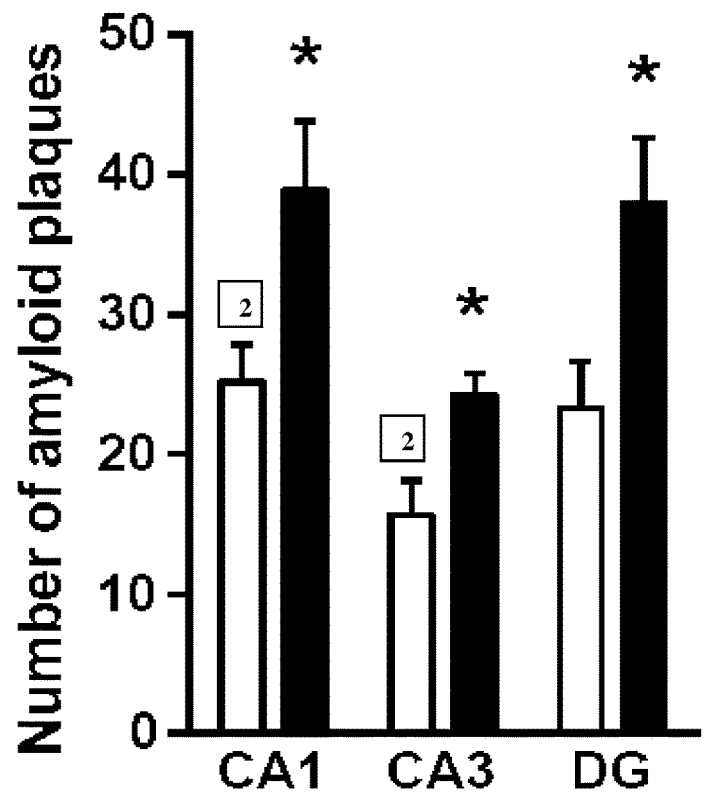
B
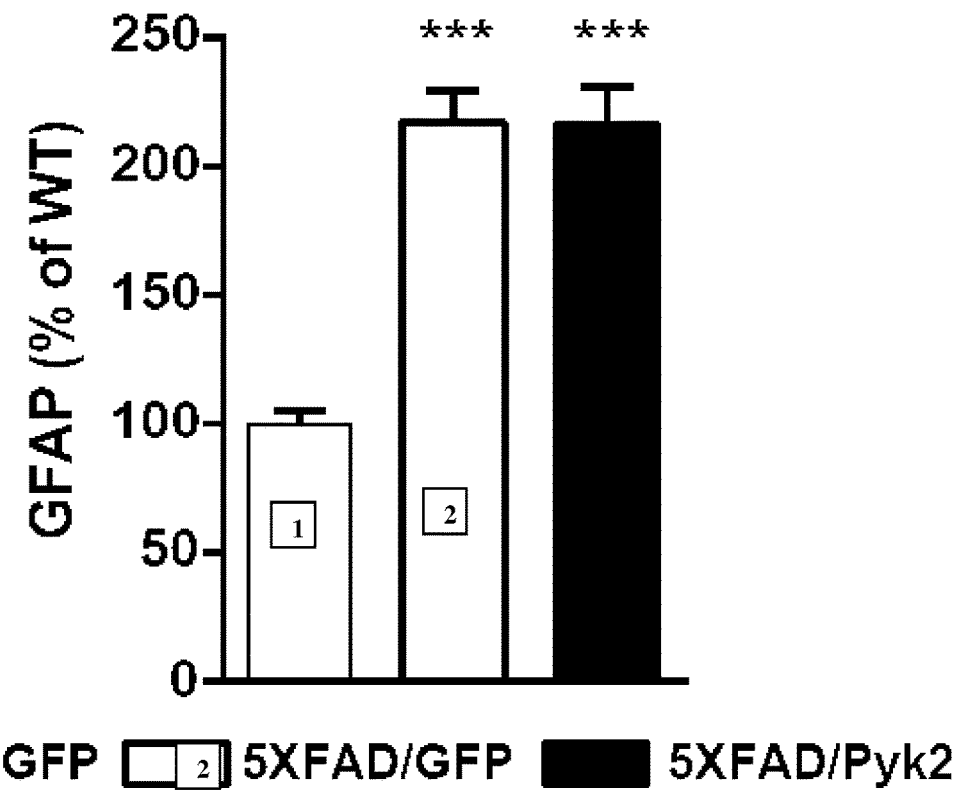
Figure 13A-B

A
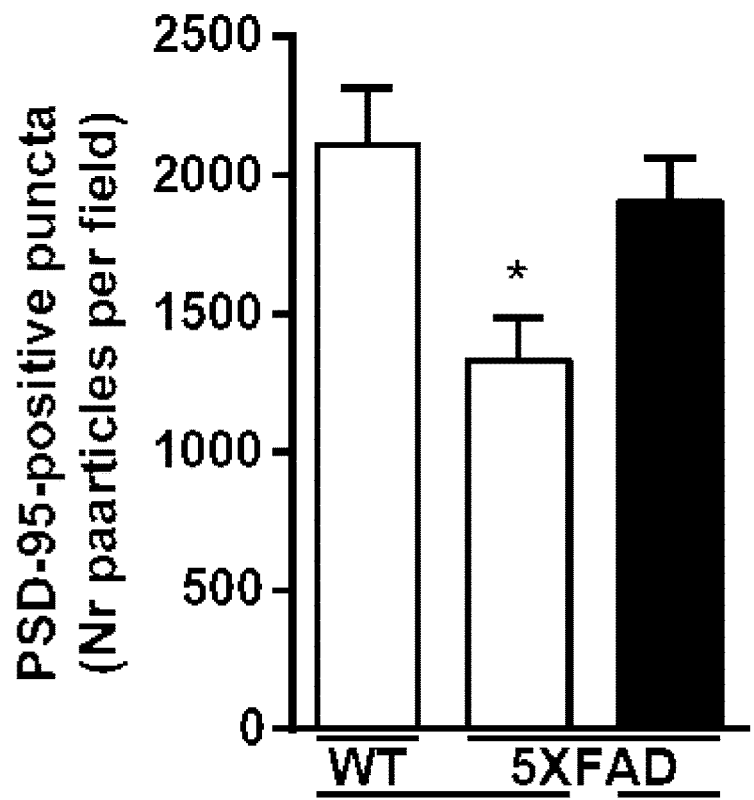
B
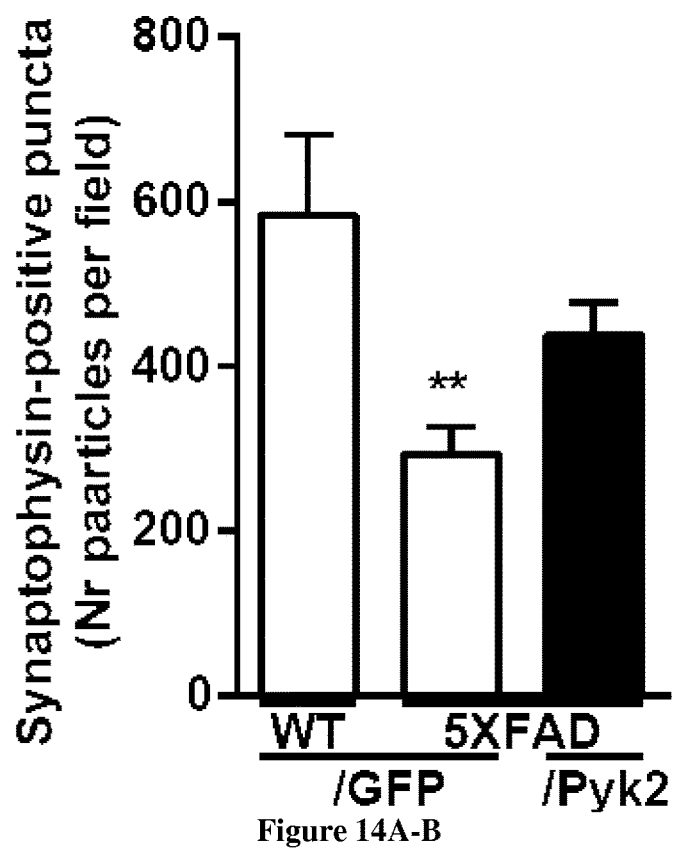
Figure 14A-B

A
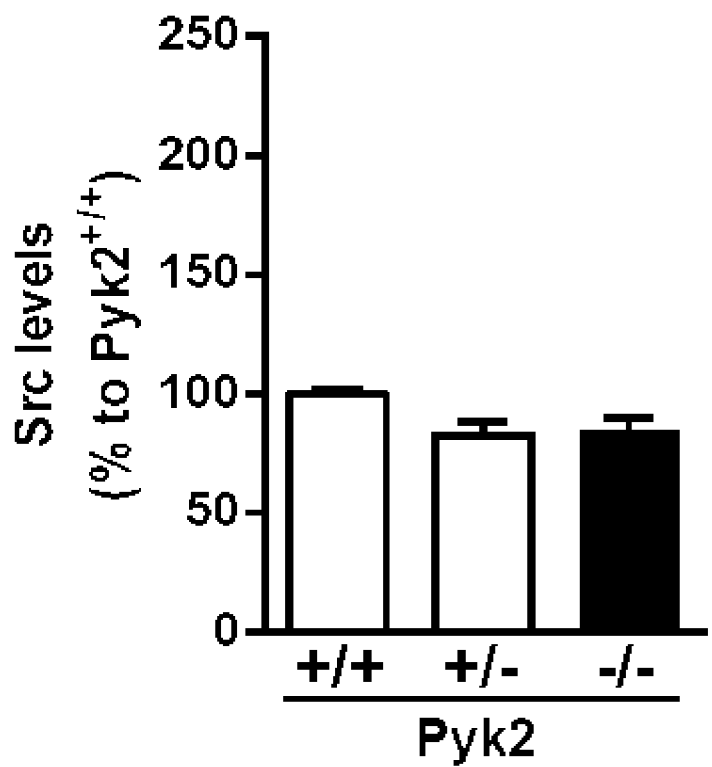
B
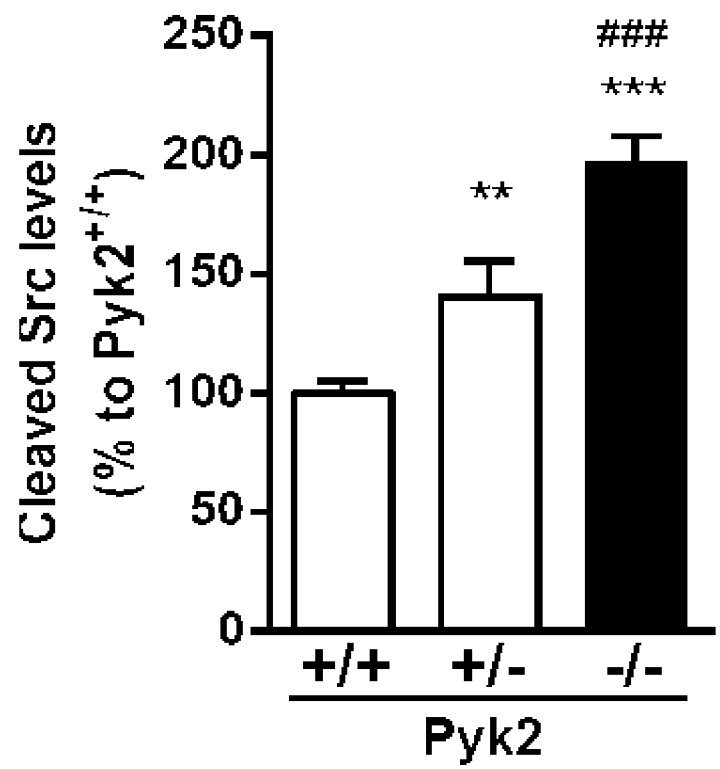
Figure 15A-B

C
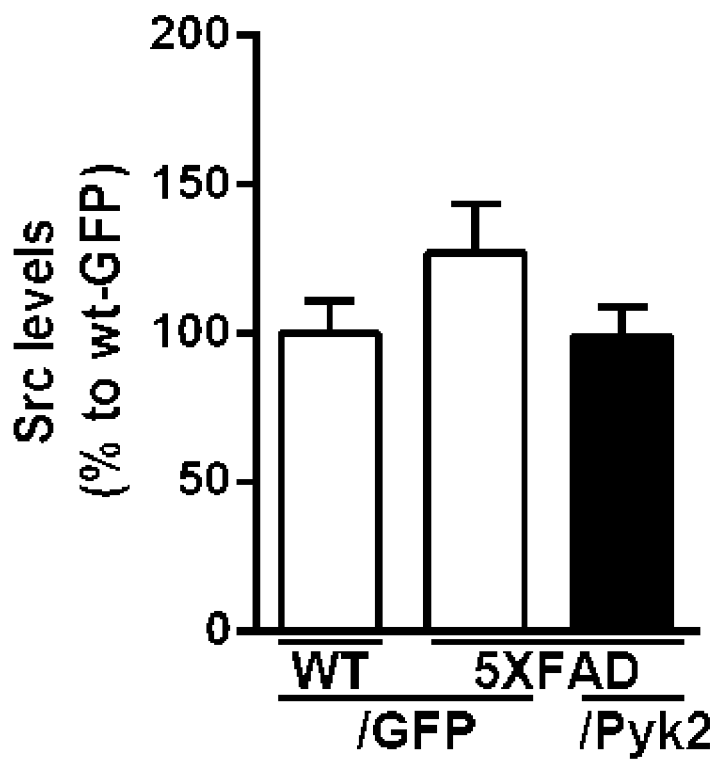
D
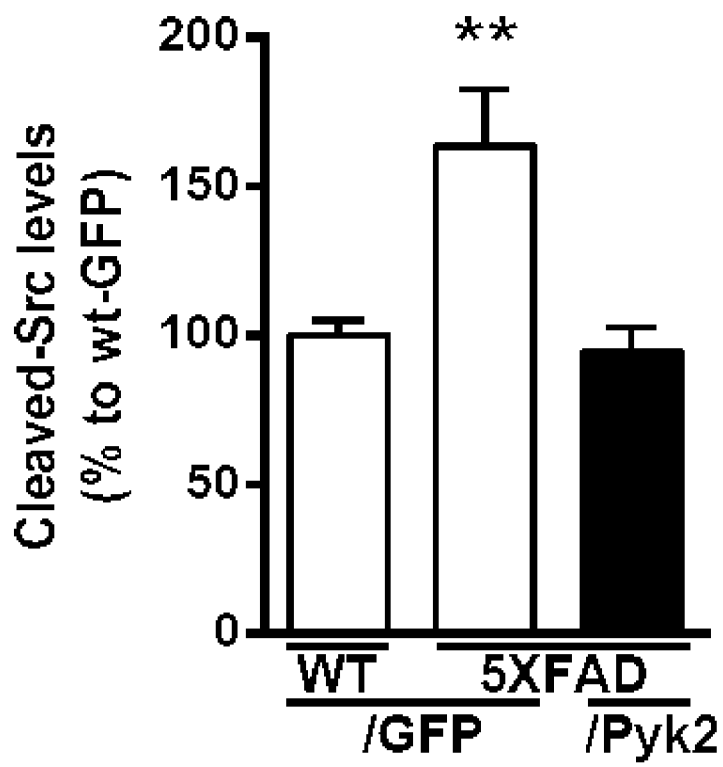
Figure 15C-D

SEQUENCE LISTING

```
<160> NUMBER OF SEQ ID NOS: 7

<210> SEQ ID NO 1
<211> LENGTH: 1009
<212> TYPE: PRT
<213> ORGANISM: Mus musculus

<400> SEQUENCE: 1

Met Ser Gly Val Ser Glu Pro Leu Ser Arg Val Lys Val Gly Thr Leu
1               5                   10                  15

Arg Arg Pro Glu Gly Pro Pro Glu Pro Met Val Val Val Pro Val Asp
            20                  25                  30

Val Glu Lys Glu Asp Val Arg Ile Leu Lys Val Cys Phe Tyr Ser Asn
        35                  40                  45

Ser Phe Asn Pro Gly Lys Asn Phe Lys Leu Val Lys Cys Thr Val Gln
    50                  55                  60

Thr Glu Ile Gln Glu Ile Ile Thr Ser Ile Leu Leu Ser Gly Arg Ile
65                  70                  75                  80
```

-continued

```
Gly Pro Asn Ile Gln Leu Ala Glu Cys Tyr Gly Leu Arg Leu Lys His
                85                  90                  95
Met Lys Ser Asp Glu Ile His Trp Leu His Pro Gln Met Thr Val Gly
            100                 105                 110
Glu Val Gln Asp Lys Tyr Glu Cys Leu His Val Glu Ala Glu Trp Arg
        115                 120                 125
Tyr Asp Leu Gln Ile Arg Tyr Leu Pro Glu Asp Phe Met Glu Ser Leu
    130                 135                 140
Lys Glu Asp Arg Thr Thr Leu Leu Tyr Phe Tyr Gln Gln Leu Arg Asn
145                 150                 155                 160
Asp Tyr Met Gln Arg Tyr Ala Ser Lys Val Ser Glu Gly Met Ala Leu
                165                 170                 175
Gln Leu Gly Cys Leu Glu Leu Arg Arg Phe Phe Lys Asp Met Pro His
            180                 185                 190
Asn Ala Leu Asp Lys Lys Ser Asn Phe Glu Leu Leu Glu Lys Glu Val
        195                 200                 205
Gly Leu Asp Leu Phe Phe Pro Lys Gln Met Gln Glu Asn Leu Lys Pro
    210                 215                 220
Lys Gln Phe Arg Lys Met Ile Gln Gln Thr Phe Gln Gln Tyr Ala Ser
225                 230                 235                 240
Leu Arg Glu Glu Glu Cys Val Met Lys Phe Phe Asn Thr Leu Ala Gly
                245                 250                 255
Phe Ala Asn Ile Asp Gln Glu Thr Tyr Arg Cys Glu Leu Ile Gln Gly
            260                 265                 270
Trp Asn Ile Thr Val Asp Leu Val Ile Gly Pro Lys Gly Ile Arg Gln
        275                 280                 285
Leu Thr Ser Gln Asp Thr Lys Pro Thr Cys Leu Ala Glu Phe Lys Gln
    290                 295                 300
Ile Lys Ser Ile Arg Cys Leu Pro Leu Glu Glu Thr Gln Ala Val Leu
305                 310                 315                 320
Gln Leu Gly Ile Glu Gly Ala Pro Gln Ser Leu Ser Ile Lys Thr Ser
                325                 330                 335
Ser Leu Ala Glu Ala Glu Asn Met Ala Asp Leu Ile Asp Gly Tyr Cys
            340                 345                 350
Arg Leu Gln Gly Glu His Lys Gly Ser Leu Ile Met His Ala Lys Lys
        355                 360                 365
Asp Gly Glu Lys Arg Asn Ser Leu Pro Gln Ile Pro Thr Leu Asn Leu
    370                 375                 380
Glu Ala Arg Arg Ser His Leu Ser Glu Ser Cys Ser Ile Glu Ser Asp
385                 390                 395                 400
Ile Tyr Ala Glu Ile Pro Asp Glu Thr Leu Arg Arg Pro Gly Gly Pro
                405                 410                 415
Gln Tyr Gly Val Ala Arg Glu Val Val Leu Asn Arg Ile Leu Gly
            420                 425                 430
Glu Gly Phe Phe Gly Glu Val Tyr Glu Gly Val Tyr Thr Asn His Lys
        435                 440                 445
Gly Glu Lys Ile Asn Val Ala Val Lys Thr Cys Lys Lys Asp Cys Thr
    450                 455                 460
Gln Asp Asn Lys Glu Lys Phe Met Ser Glu Ala Val Ile Met Lys Asn
465                 470                 475                 480
Leu Asp His Pro His Ile Val Lys Leu Ile Gly Ile Ile Glu Glu Glu
                485                 490                 495
```

-continued

Pro Thr Trp Ile Ile Met Glu Leu Tyr Pro Tyr Gly Glu Leu Gly His
            500                 505                 510

Tyr Leu Glu Arg Asn Lys Asn Ser Leu Lys Val Pro Thr Leu Val Leu
        515                 520                 525

Tyr Thr Leu Gln Ile Cys Lys Ala Met Ala Tyr Leu Glu Ser Ile Asn
    530                 535                 540

Cys Val His Arg Asp Ile Ala Val Arg Asn Ile Leu Val Ala Ser Pro
545                 550                 555                 560

Glu Cys Val Lys Leu Gly Asp Phe Gly Leu Ser Arg Tyr Ile Glu Asp
                565                 570                 575

Glu Asp Tyr Tyr Lys Ala Ser Val Thr Arg Leu Pro Ile Lys Trp Met
            580                 585                 590

Ser Pro Glu Ser Ile Asn Phe Arg Arg Phe Thr Thr Ala Ser Asp Val
        595                 600                 605

Trp Met Phe Ala Val Cys Met Trp Glu Ile Leu Ser Phe Gly Lys Gln
    610                 615                 620

Pro Phe Phe Trp Leu Glu Asn Lys Asp Val Ile Gly Val Leu Glu Lys
625                 630                 635                 640

Gly Asp Arg Leu Pro Lys Pro Glu Leu Cys Pro Pro Val Leu Tyr Thr
                645                 650                 655

Leu Met Thr Arg Cys Trp Asp Tyr Asp Pro Ser Asp Arg Pro Arg Phe
            660                 665                 670

Thr Glu Leu Val Cys Ser Leu Ser Asp Ile Tyr Gln Met Glu Lys Asp
        675                 680                 685

Ile Ala Ile Glu Gln Glu Arg Asn Ala Arg Tyr Arg Pro Pro Lys Ile
    690                 695                 700

Leu Glu Pro Thr Thr Phe Gln Glu Pro Pro Lys Pro Ser Arg Pro
705                 710                 715                 720

Lys Tyr Arg Pro Pro Gln Thr Asn Leu Leu Ala Pro Lys Leu Gln
                725                 730                 735

Phe Gln Val Pro Glu Gly Leu Cys Ala Ser Ser Pro Thr Leu Thr Ser
            740                 745                 750

Pro Met Glu Tyr Pro Ser Pro Val Asn Ser Leu His Thr Pro Pro Leu
        755                 760                 765

His Arg His Asn Val Phe Lys Arg His Ser Met Arg Glu Glu Asp Phe
    770                 775                 780

Ile Arg Pro Ser Ser Arg Glu Glu Ala Gln Gln Leu Trp Glu Ala Glu
785                 790                 795                 800

Lys Ile Lys Met Lys Gln Val Leu Glu Arg Gln Gln Lys Gln Met Val
                805                 810                 815

Glu Asp Ser Gln Trp Leu Arg Arg Glu Glu Arg Cys Leu Asp Pro Met
            820                 825                 830

Val Tyr Met Asn Asp Lys Ser Pro Leu Thr Pro Glu Lys Glu Ala Gly
        835                 840                 845

Tyr Thr Glu Phe Thr Gly Pro Pro Gln Lys Pro Pro Arg Leu Gly Ala
    850                 855                 860

Gln Ser Ile Gln Pro Thr Ala Asn Leu Asp Arg Thr Asp Asp Leu Val
865                 870                 875                 880

Tyr His Asn Val Met Thr Leu Val Glu Ala Val Leu Glu Leu Lys Asn
                885                 890                 895

Lys Leu Gly Gln Leu Pro Pro Glu Asp Tyr Val Val Val Lys Asn
            900                 905                 910

Val Gly Leu Asn Leu Arg Lys Leu Ile Gly Ser Val Asp Asp Leu Leu

```
                915                 920                 925
Pro Ser Leu Pro Ala Ser Ser Arg Thr Glu Ile Glu Gly Thr Gln Lys
    930                 935                 940

Leu Leu Asn Lys Asp Leu Ala Glu Leu Ile Asn Lys Met Lys Leu Ala
945                 950                 955                 960

Gln Gln Asn Ala Val Thr Ser Leu Ser Glu Asp Cys Lys Arg Gln Met
                965                 970                 975

Leu Thr Ala Ser His Thr Leu Ala Val Asp Ala Lys Asn Leu Leu Asp
            980                 985                 990

Ala Val Asp Gln Ala Lys Val Val Ala Asn Leu Ala His Pro Pro Ala
        995                 1000                1005

Glu

<210> SEQ ID NO 2
<211> LENGTH: 1009
<212> TYPE: PRT
<213> ORGANISM: Homo sapiens

<400> SEQUENCE: 2

Met Ser Gly Val Ser Glu Pro Leu Ser Arg Val Lys Leu Gly Thr Leu
1               5                   10                  15

Arg Arg Pro Glu Gly Pro Ala Glu Pro Met Val Val Pro Val Asp
            20                  25                  30

Val Glu Lys Glu Asp Val Arg Ile Leu Lys Val Cys Phe Tyr Ser Asn
            35                  40                  45

Ser Phe Asn Pro Gly Lys Asn Phe Lys Leu Val Lys Cys Thr Val Gln
50                  55                  60

Thr Glu Ile Arg Glu Ile Ile Thr Ser Ile Leu Leu Ser Gly Arg Ile
65                  70                  75                  80

Gly Pro Asn Ile Arg Leu Ala Glu Cys Tyr Gly Leu Arg Leu Lys His
                85                  90                  95

Met Lys Ser Asp Glu Ile His Trp Leu His Pro Gln Met Thr Val Gly
            100                 105                 110

Glu Val Gln Asp Lys Tyr Glu Cys Leu His Val Glu Ala Glu Trp Arg
        115                 120                 125

Tyr Asp Leu Gln Ile Arg Tyr Leu Pro Glu Asp Phe Met Glu Ser Leu
    130                 135                 140

Lys Glu Asp Arg Thr Thr Leu Leu Tyr Phe Tyr Gln Gln Leu Arg Asn
145                 150                 155                 160

Asp Tyr Met Gln Arg Tyr Ala Ser Lys Val Ser Glu Gly Met Ala Leu
                165                 170                 175

Gln Leu Gly Cys Leu Glu Leu Arg Arg Phe Phe Lys Asp Met Pro His
            180                 185                 190

Asn Ala Leu Asp Lys Lys Ser Asn Phe Glu Leu Leu Glu Lys Glu Val
        195                 200                 205

Gly Leu Asp Leu Phe Phe Pro Lys Gln Met Gln Glu Asn Leu Lys Pro
    210                 215                 220

Lys Gln Phe Arg Lys Met Ile Gln Gln Thr Phe Gln Gln Tyr Ala Ser
225                 230                 235                 240

Leu Arg Glu Glu Glu Cys Val Met Lys Phe Phe Asn Thr Leu Ala Gly
                245                 250                 255

Phe Ala Asn Ile Asp Gln Glu Thr Tyr Arg Cys Glu Leu Ile Gln Gly
            260                 265                 270

Trp Asn Ile Thr Val Asp Leu Val Ile Gly Pro Lys Gly Ile Arg Gln
```

```
                275                 280                 285
Leu Thr Ser Gln Asp Ala Lys Pro Thr Cys Leu Ala Glu Phe Lys Gln
290                 295                 300

Ile Arg Ser Ile Arg Cys Leu Pro Leu Glu Glu Gly Gln Ala Val Leu
305                 310                 315                 320

Gln Leu Gly Ile Glu Gly Ala Pro Gln Ala Leu Ser Ile Lys Thr Ser
                325                 330                 335

Ser Leu Ala Glu Ala Glu Asn Met Ala Asp Leu Ile Asp Gly Tyr Cys
                340                 345                 350

Arg Leu Gln Gly Glu His Gln Gly Ser Leu Ile Ile His Pro Arg Lys
                355                 360                 365

Asp Gly Glu Lys Arg Asn Ser Leu Pro Gln Ile Pro Met Leu Asn Leu
370                 375                 380

Glu Ala Arg Arg Ser His Leu Ser Glu Ser Cys Ser Ile Glu Ser Asp
385                 390                 395                 400

Ile Tyr Ala Glu Ile Pro Asp Glu Thr Leu Arg Arg Pro Gly Gly Pro
                405                 410                 415

Gln Tyr Gly Ile Ala Arg Glu Asp Val Val Leu Asn Arg Ile Leu Gly
                420                 425                 430

Glu Gly Phe Phe Gly Glu Val Tyr Glu Gly Val Tyr Thr Asn His Lys
                435                 440                 445

Gly Glu Lys Ile Asn Val Ala Val Lys Thr Cys Lys Lys Asp Cys Thr
450                 455                 460

Leu Asp Asn Lys Glu Lys Phe Met Ser Glu Ala Val Ile Met Lys Asn
465                 470                 475                 480

Leu Asp His Pro His Ile Val Lys Leu Ile Gly Ile Ile Glu Glu Glu
                485                 490                 495

Pro Thr Trp Ile Ile Met Glu Leu Tyr Pro Tyr Gly Glu Leu Gly His
                500                 505                 510

Tyr Leu Glu Arg Asn Lys Asn Ser Leu Lys Val Leu Thr Leu Val Leu
                515                 520                 525

Tyr Ser Leu Gln Ile Cys Lys Ala Met Ala Tyr Leu Glu Ser Ile Asn
530                 535                 540

Cys Val His Arg Asp Ile Ala Val Arg Asn Ile Leu Val Ala Ser Pro
545                 550                 555                 560

Glu Cys Val Lys Leu Gly Asp Phe Gly Leu Ser Arg Tyr Ile Glu Asp
                565                 570                 575

Glu Asp Tyr Tyr Lys Ala Ser Val Thr Arg Leu Pro Ile Lys Trp Met
                580                 585                 590

Ser Pro Glu Ser Ile Asn Phe Arg Arg Phe Thr Thr Ala Ser Asp Val
                595                 600                 605

Trp Met Phe Ala Val Cys Met Trp Glu Ile Leu Ser Phe Gly Lys Gln
610                 615                 620

Pro Phe Phe Trp Leu Glu Asn Lys Asp Val Ile Gly Val Leu Glu Lys
625                 630                 635                 640

Gly Asp Arg Leu Pro Lys Pro Asp Leu Cys Pro Pro Val Leu Tyr Thr
                645                 650                 655

Leu Met Thr Arg Cys Trp Asp Tyr Asp Pro Ser Asp Arg Pro Arg Phe
                660                 665                 670

Thr Glu Leu Val Cys Ser Leu Ser Asp Val Tyr Gln Met Glu Lys Asp
                675                 680                 685

Ile Ala Met Glu Gln Glu Arg Asn Ala Arg Tyr Arg Thr Pro Lys Ile
690                 695                 700
```

Leu Glu Pro Thr Ala Phe Gln Glu Pro Pro Lys Pro Ser Arg Pro
705                 710                 715                 720

Lys Tyr Arg Pro Pro Pro Gln Thr Asn Leu Leu Ala Pro Lys Leu Gln
            725                 730                 735

Phe Gln Val Pro Glu Gly Leu Cys Ala Ser Ser Pro Thr Leu Thr Ser
        740                 745                 750

Pro Met Glu Tyr Pro Ser Pro Val Asn Ser Leu His Thr Pro Pro Leu
    755                 760                 765

His Arg His Asn Val Phe Lys Arg His Ser Met Arg Glu Glu Asp Phe
770                 775                 780

Ile Gln Pro Ser Ser Arg Glu Glu Ala Gln Leu Trp Glu Ala Glu
785                 790                 795                 800

Lys Val Lys Met Arg Gln Ile Leu Asp Lys Gln Gln Lys Gln Met Val
                805                 810                 815

Glu Asp Tyr Gln Trp Leu Arg Gln Glu Lys Ser Leu Asp Pro Met
            820                 825                 830

Val Tyr Met Asn Asp Lys Ser Pro Leu Thr Pro Glu Lys Glu Val Gly
        835                 840                 845

Tyr Leu Glu Phe Thr Gly Pro Pro Gln Lys Pro Pro Arg Leu Gly Ala
    850                 855                 860

Gln Ser Ile Gln Pro Thr Ala Asn Leu Asp Arg Thr Asp Asp Leu Val
865                 870                 875                 880

Tyr Leu Asn Val Met Glu Leu Val Arg Ala Val Leu Glu Leu Lys Asn
                885                 890                 895

Glu Leu Cys Gln Leu Pro Pro Glu Gly Tyr Val Val Val Lys Asn
            900                 905                 910

Val Gly Leu Thr Leu Arg Lys Leu Ile Gly Ser Val Asp Asp Leu Leu
        915                 920                 925

Pro Ser Leu Pro Ser Ser Arg Thr Glu Ile Glu Gly Thr Gln Lys
930                 935                 940

Leu Leu Asn Lys Asp Leu Ala Glu Leu Ile Asn Lys Met Arg Leu Ala
945                 950                 955                 960

Gln Gln Asn Ala Val Thr Ser Leu Ser Glu Glu Cys Lys Arg Gln Met
                965                 970                 975

Leu Thr Ala Ser His Thr Leu Ala Val Asp Ala Lys Asn Leu Leu Asp
            980                 985                 990

Ala Val Asp Gln Ala Lys Val Leu  Ala Asn Leu Ala His  Pro Pro Ala
        995                 1000                1005

Glu

<210> SEQ ID NO 3
<211> LENGTH: 3030
<212> TYPE: DNA
<213> ORGANISM: Mus musculus

<400> SEQUENCE: 3
atgtccgggg tgtctgagcc cttgagccgt gtaaaagtgg gcactttacg ccggcctgag      60
ggccccccag agcccatggt ggtggtacca gtggatgtgg agaaggaaga cgtgcgcatc     120
ctcaaggtct gcttctacag caacagcttc aacccaggga gaacttcaa gcttgtcaaa     180 tgcacagtgc agacagagat ccaggagatc atcacctcca tcctcctgag tgggcgaata     240
gggcccaaca tccagctggc tgaatgctat gggctgaggc tgaagcacat gaagtcagac     300
gagatccact ggctgcaccc acagatgacc gtgggcgaag tgcaggacaa gtatgaatgt     360

```
ctacacgtgg aagctgagtg gaggtatgac cttcaaatcc gctacttgcc ggaagacttc      420
atggagagcc tgaaagaaga caggaccaca ttgctgtact tttatcaaca gctccggaat      480
gactacatgc aacgctacgc cagcaaggtc agtgaaggca tggctctgca gctgggctgt      540
ctggagctca ggagattctt caaggacatg ccccacaatg cactggacaa aaagtccaac      600
tttgaactcc tggaaaaaga agtcggtctg gacctgtttt tcccaaagca gatgcaggaa      660
aacttaaagc ccaagcagtt ccggaagatg atccagcaga ccttccagca gtatgcatca      720
ctccgggagg aagagtgtgt catgaaattc ttcaataccc tagcgggctt tgccaacatt      780
gaccaggaga cctaccgctg cgaactcatt caaggatgga acattactgt ggacctggtc      840
atcggcccta aaggcatccg tcagctgaca agtcaagata caaagcccac ctgcctggcc      900
gagtttaagc agatcaaatc catcaggtgc ctcccattgg aagagaccca ggcagtcctg      960
cagctgggca tcgagggtgc ccccccagtcc ttgtctatca aaacgtcgtc cctggcagag    1020
gctgagaaca tggctgacct catagatggc tactgcaggc tgcaaggaga acataagggc    1080
tctctcatca tgcatgccaa gaaagatggt gagaagagga acagcctgcc tcagatcccc    1140
acactaaacc tggaggctcg gcggtcgcac ctctcagaaa gctgcagcat agagtcagac    1200
atctatgcgg agattcccga tgagaccctg cgaagaccag gaggtccaca gtacggtgtt    1260
gcccgtgaag aagtagttct taaccgcatt ctgggtgaag gcttctttgg ggaggtctat    1320
gaaggtgtct acacgaacca caaaggggaa aaaattaatg tggccgtcaa gacctgtaag    1380
aaagactgta cccaggacaa caaggagaag ttcatgagtg aggcagtgat catgaagaat    1440
cttgaccacc ctcacatcgt gaagctgatt ggcatcattg aagaggaacc cacctggatt    1500
atcatggaac tgtatcctta tggggagctg ggacactacc tggaacgaaa taaaaactcc    1560
ctgaaggtac ccactctggt cctgtacacc ctacagatat gcaaagccat ggcctatctg    1620
gagagcatca actgtgtgca cagggatatt gctgtccgga catcctggt ggcctctcct    1680 gagtgtgtga agctggggga ctttgggctc tcccggtaca ttgaggacga agactattac    1740
aaagcctctg tgacccgtct acccatcaaa tggatgtccc ccgagtccat caacttccgc    1800
cgcttcacaa ccgccagtga tgtctggatg tttgctgtat gcatgtggga gatcctcagc    1860
tttgggaagc agccttttctt ctggctcgaa aataaggatg tcatcggagt gctggagaaa    1920
ggggacaggc tgcccaagcc cgaactctgt ccgcctgtcc tttacacact catgactcgc    1980
tgctgggact acgaccccag tgaccggccc cgcttcacgg agcttgtgtg cagcctcagt    2040
gacatttatc agatggagaa ggacattgcc atagagcaag aaaggaatgc tcgctaccga    2100 cccccccaaaa tattggagcc tactaccttt caggaacccc cacccaagcc cagccggccc    2160
aagtacagac ctcctccaca gaccaacctg ctggctccta gctgcagtt ccaggtccct    2220 gagggtctgt gtgccagctc tcctacgctt accagcccta tggagtatcc atctccagtt    2280
aactcgctac acacccccacc tctccaccgg cacaatgtct tcaagcgcca cagcatgcgg    2340
gaggaggact tcatccggcc cagtagccga gaagaggccc agcagctctg ggaggcagag    2400
aagatcaaga tgaagcaggt cctagaaaga cagcagaagc agatggtgga agattcccag    2460
tggctgaggc gagaggaaag atgcttggac cctatggttt atatgaatga caagtcccca    2520
ctgactccag agaaggaggc cggctacacg gagttcacag gcccccccaca gaaaccacct    2580 cggctcggtg cacagtccat tcagcccaca gccaacctgg acaggaccga tgacctcgtg    2640
taccacaatg tcatgacccct ggtggaggct gtgctggaac tcaagaacaa gcttggccag    2700
```

```
ttgcccoctg aggactatgt ggtggtggtg aagaacgtgg ggctgaacct gcggaagctc      2760
atcggcagtg tggacgatct cttgcccctcc ttgccggcat cttcgaggac agagattgaa    2820
gggacccaga aactgctcaa caaagacctg gcagagctca tcaacaagat gaagttggct    2880
cagcagaacg ccgtgacgtc cctgagtgag gactgcaagc ggcagatgct cacagcgtcc    2940 catacccctgg ctgtggatgc caagaacctg ctggatgctg tggaccaagc caaggttgtg   3000
gctaatctgg cccacccgcc tgcagagtga                                      3030
```

<210> SEQ ID NO 4
<211> LENGTH: 3030
<212> TYPE: DNA
<213> ORGANISM: Homo sapiens

<400> SEQUENCE: 4

```
atgtctgggg tgtccgagcc cctgagccga gtaaagttgg gcacattacg ccggcctgaa      60
ggccctgcag agcccatggt ggtggtacca gtagatgtgg aaaaggagga cgtgcgtatc     120
ctcaaggtct gcttctatag caacagcttc aatcctggga gaaacttcaa actggtcaaa    180
tgcactgtcc agacggagat ccggagatc atcacctcca tcctgctgag cgggcggatc      240
gggcccaaca tccggttggc tgagtgctat gggctgaggc tgaagcacat gaagtccgat    300
gagatccact ggctgcaccc acagatgacg gtgggtgagg tgcaggacaa gtatgagtgt    360
ctgcacgtga agccgagtg gaggtatgac cttcaaatcc gctacttgcc agaagacttc    420
atggagagcc tgaaggagga caggaccacg ctgctctatt tttaccaaca gctccggaac   480
gactacatgc agcgctacgc cagcaaggtc agcgagggca tggccctgca gctgggctgc   540
ctggagctca ggcggttctt caaggatatg ccccacaatg cacttgacaa gaagtccaac   600
ttcgagctcc tagaaaagga agtggggctg gacttgtttt tcccaaagca gatgcaggag   660
aacttaaagc ccaaacagtt ccggaagatg atccagcaga ccttccagca gtacgcctcg    720
ctcagggagg aggagtgcgt catgaagttc ttcaacactc tcgccggctt cgccaacatc   780
gaccaggaga cctaccgctg tgaactcatt caaggatgga acattactgt ggacctggtc    840
attggcccta agggatccg ccagctgact agtcaggacg caaagcccac ctgcctggcc    900
gagttcaagc agatcaggtc catcaggtgc ctcccgctgg aggagggcca ggcagtactt   960
cagctgggca ttgaaggtgc cccccaggcc ttgtccatca aaacctcatc cctagcagag  1020
gctgagaaca tggctgacct catagacggc tactgccggc tgcagggtga gcaccaaggc  1080
tctctcatca tccatcctag gaaagatggt gagaagcgga acagcctgcc ccagatcccc  1140
atgctaaacc tggaggccccg gcggtcccac ctctcagaga gctgcagcat agagtcagac  1200
atctacgcag agattcccga cgaaacccctg cgaaggcccg gaggtccaca gtatggcatt  1260
gcccgtgaag atgtggtcct gaatcgtatt cttggggaag ctttttttgg ggaggtctat   1320
gaaggtgtct acacaaatca caagggggag aaaatcaatg tagctgtcaa gacctgcaag  1380
aaagactgca ctctggacaa caaggagaag ttcatgagcg aggcagtgat catgaagaac   1440
ctcgaccacc cgcacatcgt gaagctgatc ggcatcattg aagaggagcc cacctggatc   1500
atcatggaat gtatccccta tggggagctg gccactacc tggagcggaa caagaactcc   1560
ctgaaggtgc tcaccctcgt gctgtactca ctgcagatat gcaaagccat ggcctacctg   1620
gagagcatca actgcgtgca cagggacatt gctgtccgga acatcctggt ggcctcccct   1680
gagtgtgtga agctggggga cttttggtctt tcccggtaca ttgaggacga ggactattac  1740
aaagcctctg tgactcgtct ccccatcaaa tggatgtccc cagagtccat taacttccga  1800
```

```
cgcttcacga cagccagtga cgtctggatg ttcgccgtgt gcatgtggga gatcctgagc   1860
tttgggaagc agcccttctt ctggctggag aacaaggatg tcatcgggt gctggagaaa    1920 ggagaccggc tgcccaagcc tgatctctgt ccaccggtcc tttataccct catgacccgc   1980
tgctgggact acgaccccag tgaccggccc cgcttcaccg agctggtgtg cagcctcagt   2040
gacgtttatc agatggagaa ggacattgcc atggagcaag agaggaatgc tcgctaccga   2100 accccaaaa tcttggagcc cacagccttc caggaacccc acccaagcc cagccgacct     2160 aagtacagac cccctccgca aaccaacctc ctggctccaa agctgcagtt ccaggttcct   2220
gagggtctgt gtgccagctc tcctacgctc accagcccta tggagtatcc atctcccgtt   2280
aactcactgc acaccccacc tctccaccgg cacaatgtct caaacgcca cagcatgcgg    2340 gaggaggact catccaacc cagcagccga aagaggccc agcagctgtg ggaggctgaa     2400
aaggtcaaaa tgcggcaaat cctggacaaa cagcagaagc agatggtgga ggactaccag  2460
tggctcaggc aggaggagaa gtccctggac cccatggttt atatgaatga taagtccca    2520 ttgacgccag agaaggaggt cggctacctg gagttcacag gccccccaca gaagcccccg  2580
aggctgggcg cacagtccat ccagcccaca gctaacctgg accggaccga tgacctggtg  2640
tacctcaatg tcatggagct ggtgcgggcc gtgctggagc tcaagaatga gctctgtcag  2700 ctgcccccg agggctacgt ggtggtggtg aagaatgtgg ggctgaccct gcggaagctc   2760
atcgggagcg tggatgatct cctgccttcc ttgccgtcat cttcacggac agagatcgag  2820
ggcacccaga aactgctcaa caaagacctg gcagagctca tcaacaagat gcggctggcg  2880
cagcagaacg ccgtgacctc cctgagtgag gagtgcaaga ggcagatgct gacggcttca  2940
cacaccctgg ctgtggacgc caagaacctg ctcgacgctg tggaccaggc caaggttctg  3000
gccaatctgg cccacccacc tgcagagtga                                   3030
```

<210> SEQ ID NO 5
<211> LENGTH: 7841
<212> TYPE: DNA
<213> ORGANISM: Artificial
<220> FEATURE:
<223> OTHER INFORMATION: Synthetic expression cassette of the AAV transfer vector encoding codon-optimized mouse PYK2 (AAV-CaMKII-EGFP-T2A-mPTK2B)

<400> SEQUENCE: 5

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggggttcc tgcggccaat tcagtcgata actataacgg tcctaaggta   180
gcgatttaaa tacgcgctct cttaaggtag ccccgggacg cgtcaattga gcatgatca    240 cttgtggact aagtttgttc gcatcccctt ctccaacccc ctcagtacat caccctgggg  300
gaacagggtc cacttgctcc tgggcccaca cagtcctgca gtattgtgta tataaggcca   360
gggcaaagag gagcaggttt taaagtgaaa ggcaggcagg tgttggggag gcagttaccg   420
gggcaacggg aacagggcgt ttcggaggtg gttgccatgg ggacctggat gctgacgaag   480
gctcgcgagg ctgtgagcag ccacagtgcc ctgctcagaa gccccaagct cgtcagtcaa   540
gccggttctc cgtttgcact caggagcacg ggcaggcgag tggcccctag ttctggggc    600 agcgctagcg tttaaactta agcttggtac cggccgctgc ggcctcgag caagctggct   660 agttaagcta tcaacaagtt tgtataaaaa agcaggcttt aaaggaacca attcagtcga  720
```

| | |
|---|---|
| cgctagctcg ccaccatggt gagcaagggc gaggagctgt tcaccggggt ggtgcccatc | 780 |
| ctggtcgagc tggacggcga cgtaaacggc cacaagttca gcgtgtccgg cgagggcgag | 840 |
| ggcgatgcca cctacggcaa gctgaccctg aagttcatct gcaccaccgg caagctgccc | 900 |
| gtgcccctggc ccaccctcgt gaccaccctg acctacggcg tgcagtgctt cagccgctac | 960 |
| cccgaccaca tgaagcagca cgacttcttc aagtccgcca tgcccgaagg ctacgtccag | 1020 |
| gagcgcacca tcttcttcaa ggacgacggc aactacaaga cccgcgccga ggtgaagttc | 1080 |
| gagggcgaca ccctggtgaa ccgcatcgag ctgaagggca tcgacttcaa ggaggacggc | 1140 |
| aacatcctgg ggcacaagct ggagtacaac tacaacagcc acaacgtcta tatcatggcc | 1200 |
| gacaagcaga agaacggcat caaggtgaac ttcaagatcc gccacaacat cgaggacggc | 1260 |
| agcgtgcagc tcgccgacca ctaccagcag aacacccca tcggcgacgg ccccgtgctg | 1320 |
| ctgcccgaca ccactacct gagcacccag tccgccctga gcaaagaccc caacgagaag | 1380 |
| cgcgatcaca tggtcctgct ggagttcgtg accgccgccg ggatcactct cggcatggac | 1440 |
| gagctgtaca agggatccgg cagtggagag ggcagaggaa gtctgctaac atgcggtgac | 1500 |
| gtcgaggaga atcctggccc aagatctatg tccggggtgt ctgagccctt gagccgtgta | 1560 |
| aaagtgggca ctttacgccg gcctgagggc cccccagagc ccatggtggt ggtaccagtg | 1620 |
| gatgtggaga aggaagacgt gcgcatcctc aaggtctgct ctacagcaa cagcttcaac | 1680 |
| ccagggaaga acttcaagct tgtcaaatgc acagtgcaga cagagatcca ggagatcatc | 1740 |
| acctccatcc tcctgagtgg gcgaataggg cccaacatcc agctggctga atgctatggg | 1800 |
| ctgaggctga agcacatgaa gtcagacgag atccactggc tgcacccaca gatgaccgtg | 1860 |
| ggcgaagtgc aggacaagta tgaatgtcta cacgtggaag ctgagtggag gtatgacctt | 1920 |
| caaatccgct acttgccgga agacttcatg gagagcctga agaagacag gaccacattg | 1980 |
| ctgtactttt atcaacagct ccggaatgac tacatgcaac gctacgccag caaggtcagt | 2040 |
| gaaggcatgg ctctgcagct gggctgtctg gagctcagga gattcttcaa ggacatgccc | 2100 |
| cacaatgcac tggacaaaaa gtccaacttt gaactcctgg aaaaagaagt cggtctggac | 2160 |
| ctgttttcc caaagcagat gcaggaaaac ttaaagccca gcagttccg gaagatgatc | 2220 |
| cagcagacct tccagcagta tgcatcactc cgggaggaag agtgtgtcat gaaattcttc | 2280 |
| aatacccctag cgggctttgc caacattgac caggagacct accgctgcga actcattcaa | 2340 |
| ggatggaaca ttactgtgga cctggtcatc ggccctaaag gcatccgtca gctgacaagt | 2400 |
| caagatacaa agcccacctg cctggccgag tttaagcaga tcagatccat caggtgcctc | 2460 |
| ccattggaag agacccaggc agtcctgcag ctgggcatcg agggtgcccc ccagtccttg | 2520 |
| tctatcaaaa cgtcgtccct ggcagaggct gagaacatgg ctgatctcat agatggctac | 2580 |
| tgcaggctgc aaggagaaca taagggctct ctcatcatgc atgccaagaa agatggtgag | 2640 |
| aagaggaaca gcctgcctca gatccccaca ctaaacctgg aggctcggcg gtcgcacctc | 2700 |
| tcagaaagct gcagcataga gtcagacatc tatgcggaga ttcccgatga accctgcga | 2760 |
| agaccaggag gtccacagta cggtgttgcc cgtgaagaag tagttcttaa ccgcattctg | 2820 |
| ggtgaaggct cttttggga ggtctatgaa ggtgtctaca cgaaccacaa aggggaaaaa | 2880 |
| attaatgtgg ccgtcaagac ctgtaagaaa gactgtaccc aggacaacaa ggagaagttc | 2940 |
| atgagtgagg cagtgatcat gaagaatctt gaccaccctc acatcgtgaa gctgattggc | 3000 |
| atcattgaag aggaacccac ctggattatc atggaactgt atcctatgg ggagctggga | 3060 |
| cactacctgg aacgaaataa aaactccctg aaggtaccca ctctggtcct gtacacccta | 3120 |

```
cagatatgca aagccatggc ctatctggag agcatcaact gtgtgcacag ggatattgct   3180
gtccggaaca tcctggtggc ctctcctgag tgtgtgaagc tgggggactt tgggctctcc   3240
cggtacattg aggacgaaga ctattacaaa gcctctgtga cacgtctacc catcaaatgg   3300
atgtcccccg agtccatcaa cttccgccgc ttcacaaccg ccagtgatgt ctggatgttt   3360
gctgtatgca tgtgggagat cctcagcttt gggaagcagc cttcttctg gctcgaaaat     3420 aaggatgtca tcggagtgct ggagaaaggg gacaggctgc ccaagcccga actctgtccg   3480
cctgtccttt acacactcat gactcgctgc tgggactacg accccagtga ccggccccgc   3540
ttcacggagc ttgtgtgcag cctcagtgac atttatcaga tggagaagga cattgccata   3600
gagcaagaaa ggaatgctcg ctaccgaccc cctaaaatat tggagcctac tacctttcag   3660 gaaccccccac ccaagcccag ccggcccaag tacagacctc ctccacagac caacctgctg   3720
gctcctaagc tgcagttcca ggtccctgag ggtctgtgtg ccagctctcc tacgcttacc   3780
agccctatgg agtatccatc tccagttaac tcgctgcaca ccccacctct ccaccggcac   3840
aatgtcttca gcgccacag catgcgggag gaggacttca tccggcccag tagccgagaa   3900
gaggcccagc agctctggga ggcagagaag atcaagatga agcaggtcct agaaagacag   3960
cagaagcaga tggtggaaga ttcccagtgg ctgaggcgag aggaaagatg cttggaccct   4020
atggtttata tgaatgacaa gtccccactg actccagaga aggaggccgg ctacacggag   4080
ttcacagggc ccccacagaa accacctcgg ctcggtgcac agtccattca gcccacagcc   4140
aacctggaca ggaccgatga cctcgtgtac cacaatgtca tgaccctggt ggaggctgtg   4200
ctggaactca agaacaagct tggccagttg ccccctgagg actatgtggt ggtggtgaag   4260
aacgtggggc tgaacctgcg gaagctcatc ggcagtgtgg acgatctctt gcctccttg    4320 ccggcatctt cgaggacaga gattgaaggg acccagaaac tgctcaacaa agacctggca   4380
gagctcatca caagatgaa gttggctcag cagaacgccg tgacgtccct gagtgaggac    4440
tgcaagcggc agatgctcac agcgtcccat accctggctg tggatgccaa gaacctgctg   4500
gatgctgtgg accaagccaa ggttgtggct aatctggccc accgcctgc agagtgagcg    4560 gccgcctcga gtctagaccc agctttcttg tataaagtgg ttgatctaga gggcccgtaa   4620
ctagttgaca tatgaccggt tagtaatgag tttatccagc acagtggcgg ccgctcgagt   4680
ctagagggcc cttcgaaggt aagcctatcc ctaaccctct cctcggtctc gattctacgc   4740
gtaccggtca tcatcaccat caccattgag tttaaacccg ctgatcagcc tcgactgtgc   4800
cttctagttg ccagccatct gttgtttgcc cctcccccgt gccttccttg acctggaag    4860 gtgccactcc cactgtcctt tcctaataaa atgaggaaat tgcatcgcat tgtctgagta   4920
ggtgtcattc tattctgggg ggtggggtgg ggcaggacac aaggggggag gattgggaag   4980
acaatagcag gcatgctggg gatgcggtgg gctctatggc ttctgaggcg gaaagaacca   5040
gatcctctct taaggtagca tcgagattta aattagggat aacagggtaa tggcgcgggc   5100
cgcaggaacc cctagtgatg gagttggcca ctccctctct gcgcgctcgc tcgctcactg   5160
aggccgggcg accaaaggtc gcccgacgcc cgggctttgc ccgggcggcc tcagtgagcg   5220
agcgagcgcg cagctgcctg caggggcgcc tgatgcggta ttttctcctt acgcatctgt   5280
gcggtatttc acaccgcata cgtcaaagca accatagtac gcgccctgta gcggcgcatt   5340
aagcgcggcg ggtgtggtgg ttacgcgcag cgtgaccgct acacttgcca gcgccctagc   5400
gcccgctcct ttcgctttct tcccttcctt tctcgccacg ttcgccggct ttccccgtca   5460
```

```
agctctaaat cggggctcc ctttagggtt ccgatttagt gctttacggc acctcgaccc     5520
caaaaaactt gatttgggtg atggttcacg tagtgggcca tcgccctgat agacggtttt    5580
tcgccctttg acgttggagt ccacgttctt taatagtgga ctcttgttcc aaactggaac    5640
aacactcaac cctatctcgg gctattcttt tgatttataa gggattttgc cgatttcggc    5700
ctattggtta aaaatgagc tgatttaaca aaaatttaac gcgaatttta acaaaatatt     5760
aacgtttaca attttatggt gcactctcag tacaatctgc tctgatgccg catagttaag    5820
ccagccccga cacccgccaa cacccgctga cgcgccctga cgggcttgtc tgctcccggc    5880
atccgcttac agacaagctg tgaccgtctc cgggagctgc atgtgtcaga ggttttcacc    5940
gtcatcaccg aaacgcgcga gacgaaaggg cctcgtgata cgcctatttt tataggttaa    6000
tgtcatgata ataatggttt cttagacgtc aggtggcact tttcggggaa atgtgcgcgg    6060
aaccctatt tgtttatttt tctaaataca ttcaaatatg tatccgctca tgagacaata     6120
accctgataa atgcttcaat aatattgaaa aggaagagt atgagtattc aacatttccg     6180
tgtcgccctt attcccttt ttgcggcatt ttgccttcct gtttttgctc acccagaaac     6240
gctggtgaaa gtaaaagatg ctgaagatca gttgggtgca cgagtgggtt acatcgaact    6300
ggatctcaac agcggtaaga tccttgagag ttttcgcccc gaagaacgtt ttccaatgat    6360
gagcactttt aaagttctgc tatgtggcgc ggtattatcc cgtattgacg ccgggcaaga    6420
gcaactcggt cgccgcatac actattctca gaatgacttg gttgagtact caccagtcac    6480
agaaaagcat cttacggatg catgacagt aagagaatta tgcagtgctg ccataaccat     6540
gagtgataac actgcggcca acttacttct gacaacgatc ggaggaccga aggagctaac    6600
cgcttttttg cacaacatgg ggatcatgt aactcgcctt gatcgttggg aaccggagct     6660
gaatgaagcc ataccaaacg acgagcgtga ccaccacgatg cctgtagcaa tggcaacaac    6720
gttgcgcaaa ctattaactg gcgaactact tactctagct tcccggcaac aattaataga    6780
ctggatggag gcggataaag ttgcaggacc acttctgcgc tcggcccttc cggctggctg    6840
gtttattgct gataaatctg gagccggtga gcgtgggtct cgcggtatca ttgcagcact    6900
ggggccagat ggtaagccct cccgtatcgt agttatctac acgacgggga gtcaggcaac    6960
tatggatgaa cgaaatagac agatcgctga gataggtgcc tcactgatta gcattggta    7020
actgtcagac caagtttact catatatact ttagattgat ttaaaacttc atttttaatt    7080
taaaaggatc taggtgaaga tccttttttga taatctcatg accaaaatcc cttaacgtga    7140
gttttcgttc cactgagcgt cagaccccgt agaaaagatc aaaggatctt cttgagatcc    7200
ttttttttctg cgcgtaatct gctgcttgca acaaaaaaa ccaccgctac cagcggtggt    7260
ttgtttgccg gatcaagagc taccaactct tttccgaag gtaactggct tcagcagagc     7320
gcagatacca aatactgtcc ttctagtgta gccgtagtta ggccaccact tcaagaactc    7380
tgtagcaccg cctacatacc tcgctctgct aatcctgtta ccagtggctg ctgccagtgg    7440
cgataagtcg tgtcttaccg ggttggactc aagacgatag ttaccggata aggcgcagcg    7500
gtcgggctga acggggggtt cgtgcacaca gcccagcttg gagcgaacga cctacaccga    7560
actgagatac ctacagcgtg agctatgaga aagcgccacg cttcccgaag ggagaaaggc    7620
ggacaggtat ccggtaagcg gcagggtcgg aacaggagag cgcacgaggg agcttccagg    7680
gggaaacgcc tggtatcttt atagtcctgt cgggtttcgc cacctctgac ttgagcgtcg    7740
atttttgtga tgctcgtcag ggggggcgag cctatgaaaa acgccagca acgcggcctt    7800
tttacggttc ctggcctttt gctggccttt tgctcacatg t                       7841
```

```
<210> SEQ ID NO 6
<211> LENGTH: 30
<212> TYPE: DNA
<213> ORGANISM: Artificial
<220> FEATURE:
<223> OTHER INFORMATION: Synthetic Pyk2 forward primer

<400> SEQUENCE: 6
gagagtgctg ggtactccag actcagatag                                30

<210> SEQ ID NO 7
<211> LENGTH: 27
<212> TYPE: DNA
<213> ORGANISM: Artificial
<220> FEATURE:
<223> OTHER INFORMATION: Synthetic Pyk2 reverse primer

<400> SEQUENCE: 7
ttcaggaaca ccagagaact agggtgg                                   27
```

METHODS AND PHARMACEUTICAL COMPOSITION FOR THE TREATMENT OF NEURODEGENERATIVE DISEASE

FIELD OF THE INVENTION

The present invention relates to methods and pharmaceutical compositions for the treatment of neurodegenerative disease. In particular, present invention relates to methods for the treatment of neurodegenerative disease, like Huntinghton's and Alzheimer's disease, comprising administering a therapeutically effective amount of a vector which comprises a nucleic acid molecule encoding for PYK2 polypeptide.

BACKGROUND OF THE INVENTION

Synaptic dysfunction, cognitive decline are hallmark features of neurodegenerative disease such as Alzheimer's disease (AD) and Huntington's disease (HD).

Synaptic function and plasticity, as well as spine morphology are regulated by multiple signaling pathways that integrate the diversity of signals converging on synapses. These pathways include tyrosine phosphorylation, which has been known for many years[1,2] but whose functional importance is still not well understood. Among the known molecular players, proline-rich tyrosine kinase 2 (Pyk2) is particularly intriguing since it is a non-receptor tyrosine kinase that can be activated by $Ca^{2+}$ and is highly expressed in forebrain neurons, especially in the hippocampus[3,4]. Previous findings indicated a role for Pyk2 in synaptic plasticity[1,5-7] and its gene, PTK2B, is a susceptibility locus for Alzheimer's disease[8]. Pyk2 is activated by $Ca^{2+}$, and although the mechanism has not been fully elucidated, it probably involves dimer assembly[9], which triggers its autophosphorylation at Tyr402 and the recruitment of Src-family kinases (SFKs)[10]. Tyr402 phosphorylation is increased by neuronal depolarization[11] and tetanic stimulation in hippocampal slices, and by activation of NMDA[5] or group I metabotropic[12] glutamate receptors in cultured hippocampal neurons. Pyk2 and SFKs are part of the NMDA receptor complex[7,13] and Pyk2 interacts directly with post-synaptic density (PSD) proteins PSD95[14], SAP102[14], and SAPAP3[15]. Long-term potentiation (LTP) of CA1 synapses requires protein tyrosine phosphorylation[16,17] and is prevented by a kinase-dead Pyk2[7] or by competition of Pyk2: PSD95 interaction[5]. These results led to the suggestion of a role of $Ca^{2+}$-induced activation of Pyk2 in regulating NMDA receptor function and synaptic plasticity, likely through recruitment of SFKs[1,2]. However, the functional relevance of these findings in vivo is not known and the role of Pyk2 in hippocampal physiology or pathology has not been investigated. Pyk2 knockout mice display a mild immunological phenotype but their nervous system has not been studied[18].

SUMMARY OF THE INVENTION

The present invention relates to methods and pharmaceutical compositions for the treatment of neurodegenerative disease. In particular, the present invention is defined by the claims.

DETAILED DESCRIPTION OF THE INVENTION

Here inventors show that the inactivation of one or two alleles of the Pyk2 gene does not alter hippocampal development but prevents hippocampal-dependent memory tasks and LTP. Inventors provide evidence for multiple roles of Pyk2 in spine morphology and post-synaptic structure. Moreover, they show that Pyk2 is decreased in the hippocampus of patients with Huntington's disease (HD), an inherited neurodegenerative disorder, which results from the expansion of a CAG trinucleotide repeat in the huntingtin (Htt) gene[19]. Pyk2 is also decreased in R6/1 mice, which express a mutated form of Htt and display a hippocampal phenotype similar to that observed in Pyk2 mutant mice. This phenotype is partly rescued by restoring Pyk2 levels, suggesting a reversible role of Pyk2 deficit in the HD mouse model.

In a second study on Alzheimer disease (AD), inventors investigate the role of Pyk2 in AD by using the severe and well-established, plaque-developing 5×FAD mouse model. These mice show most of the key features of AD such as early hippocampal-related cognitive deficits, neuroinflamation, plaque deposition, and age-dependent synaptic degeneration indicated by the reduction of synaptic markers (Oakley. Craft 2006 J Neurosci). Inventors designed loss and gain of function approaches to test the potential role of Pyk2 in this AD transgenic mouse model. In the first they crossed Pyk2 knockout mice with 5×FAD mice and they evaluated whether the resulting double mutant mice (5×FAD:Pyk2$^{-/-}$) displayed a phenotype improvement or aggravation. They then performed the opposite approach by over-expressing Pyk2 in the hippocampus of 5×FAD mice by using local adeno-associated virus expression/delivery. The results indicated that deletion of the Pyk2 gene did not alter the 5×FAD phenotype. In contrast, over-expression of Pyk2 in the hippocampus promoted a significant rescue of several phenotypic hallmarks of the 5×FAD mice.

Thus, the inventors used direct overexpression of PYK2 by AAV-mediated gene transfer into the brain to explore its potential to ameliorate or rescue structural, electrophysiological and behavioral deficits of AD model mice and in HD mouse model. Unexpectedly, they found that overexpression of PYK2 in these 2 models improves behavioral phenotypes linked to synaptic plasticity and partially rescues spine density deficits. Restoration of synaptic properties (including plasticity) and increased spine density is also accompanied by a rescue of spatial memory. Collectively, these data suggest, that PYK2 may restore cognitive functions in neurodegenerative diseases.

Accordingly, a first object of the present invention relates to a method of treating neurodegenerative disease in a subject in need thereof comprising administering to the subject a therapeutically effective amount of a vector which comprises a nucleic acid molecule encoding for a PYK2 polypeptide Another object of the present invention relates to a method of treating Alzheimer's disease in a subject in need thereof comprising administering to the subject a therapeutically effective amount of a vector which comprises a nucleic acid molecule encoding for PYK2 polypeptide.

Another object of the present invention relates to a method of treating Huntington's disease in a subject in need thereof comprising administering to the subject a therapeutically effective amount of a vector which comprises a nucleic acid molecule encoding for PYK2 polypeptide.

In a specific embodiment, the methods of the invention allow to treat cognitive deficits of neurodegenerative disease.

In a specific embodiment, the methods of the invention allow to treat motor deficits of neurodegenerative disease, in particular Huntington's disease.

As used herein, the term "subject" denotes a mammal, such as a rodent, a feline, a canine, and a primate. Preferably a subject according to the invention is a human. In the context of the present invention, a "subject in need thereof" denotes a subject, preferably a human, with Alzheimer's disease, or Huntington's disease.

As used herein, the term "Neurodegenerative disease" has its general meaning in the art and refers to diseases with neurodegeneration which is the progressive loss of structure or function of neurons, including death of neurons. Many neurodegenerative diseases including amyotrophic lateral sclerosis, Parkinson's, Alzheimer's, and Huntington's occur as a result of neurodegenerative processes. Such diseases are incurable, resulting in progressive degeneration and/or death of neuron cells. As research progresses, many similarities appear that relate these diseases to one another on a subcellular level. Discovering these similarities offers hope for therapeutic advances that could ameliorate many diseases simultaneously. There are many parallels between different neurodegenerative disorders including atypical protein assemblies as well as induced cell death (Rubinsztein D C (2006). Nature. 443 (7113): 780-6 and Bredesen De1., et al (2006). Nature. 443 (7113): 796-802).

Neurodegenerative diseases include but are not limited to Alzheimer's disease, dementia with Lewy bodies (DLB), amyotrophic lateral sclerosis (ALS) with frontotemporal dementia, inclusion body myopathy with Paget's disease of bone and/or frontotemporal dementia (IBMPFD), frontotemporal lobar degeneration, synucleopathies, Huntington's disease and Parkinson's disease, amyloidopathies including amyloid angiopathies, tauopathies including frontotemporal dementia with Parkinsonism linked to chromosome 17, neuromuscular diseases with protein inclusions, as well as developmental diseases including Down syndrome. Preferably, the disease is selected from Alzheimer's disease, amyotrophic lateral sclerosis (ALS) with frontotemporal dementia, inclusion body myopathy with Paget's, disease of bone and/or frontotemporal dementia (IBMPFD), frontotemporal lobar degeneration, synucleopathies, Huntington's disease, amyloidopathies including amyloid, angiopathies, tauopathies including frontotemporal dementia with Parkinsonism linked to chromosome 17. More preferably, the disease is selected from Alzheimer's disease, and Huntington's disease.

As used herein, the term "Alzheimer's disease" has its general meaning in the art and denotes chronic neurodegenerative disease that usually starts slowly and gets worse over time. Alzheimer's disease (AD) is characterized by amyloid deposits, intracellular neurofibrillary tangles, neuronal loss and a decline in cognitive function. The most common early symptom is difficulty in remembering recent events (short-term memory loss). As the disease advances, symptoms can include: problems with language, disorientation (including easily getting lost), mood swings, loss of motivation, not managing self-care, and behavioural issues. AD is undoubtedly multifactorial, but the amyloid protein precursor (APP) is a key element in its development. The physiological functions of APP and of its first cleavage product beta-amyloid peptide are unclear, but it has been shown to play crucial roles for spine density, morphology and plasticity. As used herein, the term "prodromal Alzheimer's" refers to the very early form of Alzheimer's when memory is deteriorating but a person remains functionally independent.

As used herein, the term "Huntington's disease" has its general meaning in the art and refers to the most frequent neurodegenerative disease caused by an expansion of glutamine repeats. The main clinical manifestations of HD are chorea, cognitive impairment and psychiatric disorders. The transmission of HD is autosomic dominant with a complete penetrance. The mutation responsible for HD, an unstable expansion of CAG repeat sequence, is located at the 5' terminal part of the IT15 gene encoding the Huntingtin (Htt). One important characteristic of HD is the vulnerability of a particular brain region, the striatum, despite similar expression of the mutated protein in other brain areas (Roze et al., 2008a). Furthermore, despite the early expression of mutated Htt (Exp-Htt) in all neuronal cells, i.e. as soon as birth, the first symptoms and neuropathological hallmarks appear at adulthood, around 40-45 years old. The age of onset of the disease is conversely proportional to the number of CAG repeats in the affected allele. Once the first symptoms have appeared, the disease progresses and leads progressively to death. One currently admitted hypothesis is that alteration of specific signalling pathways during ageing increases Exp-Htt-induced molecular alterations, specifically or primarily in striatal neurons.

In a specific embodiment, the methods of the invention allow to treat cognitive deficits and/or motor deficits of Huntington's disease.

As used herein, the term "treatment" or "treat" refers to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In particular, the method of the present invention is particularly suitable for rescuing memory impairment, synaptic plasticity and/or spine density, ameliorating both structural and functional synaptic impairments, and/or restoring cognitive functions.

In particular, the method of the present invention is particularly suitable for treating/decreasing chorea, rigidity, writhing motions or abnormal posturing, small unintentionally initiated or uncompleted motions, lack of coordination, difficulties to move, abnormal facial expression, difficulties chewing, eating, swallowing, and speaking, seizures and any others signs of motor deficits.

In some embodiments, the vector of the present invention comprises a nucleic acid encoding for a PYK2 polypeptide.

As used herein the term "PYK2" or "Protein tyrosine kinase 2 beta has its general meaning in the art and refers to the protein (enzyme) that in humans is encoded by the PTK2B gene (Gene ID: 2185 for human). This cytoplasmic protein tyrosine kinase is involved in calcium-induced regulation of ion channels and activation of the MAP kinase signaling pathway. Exemplary amino acid sequences of PYK2 include sequences a set forth in SEQ ID NO:1 and SEQ ID NO:2.

```
SEQ ID NO1: amino acid sequence of the murine
PYK2 protein
MSGVSEPLSR VKVGTLRRPE GPPEPMVVVP VDVEKEDVRI

LKVCFYSNSF NPGKNFKLVK CTVQTEIQEI ITSILLSGRI

GPNIQLAECY GLRLKHMKSD EIHWLHPQMT VGEVQDKYEC

LHVEAEWRYD LQIRYLPEDF MESLKEDRTT LLYFYQQLRN

DYMQRYASKV SEGMALQLGC LELRRFFKDM PHNALDKKSN

FELLEKEVGL DLFFPKQMQE NLKPKQFRKM IQQTFQQYAS

LREEECVMKF FNTLAGFANI DQETYRCELI QGWNITVDLV

IGPKGIRQLT SQDTKPTCLA EFKQIKSIRC LPLEETQAVL

QLGIEGAPQS LSIKTSSLAE AENMADLIDG YCRLQGEHKG

SLIMHAKKDG EKRNSLPQIP TLNLEARRSH LSESCSIESD

IYAEIPDETL RRPGGPQYGV AREEVVLNRI LGEGFFGEVY

EGVYTNHKGE KINVAVKTCK KDCTQDNKEK FMSEAVIMKN

LDHPHIVKLI GIIEEEPTWI IMELYPYGEL GHYLERNKNS

LKVPTLVLYT LQICKAMAYL ESINCVHRDI AVRNILVASP

ECVKLGDFGL SRYIEDEDYY KASVTRLPIK WMSPESINFR

RFTTASDVWM FAVCMWEILS FGKQPFFWLE NKDVIGVLEK

GDRLPKPELC PPVLYTLMTR CWDYDPSDRP RFTELVCSLS

DIYQMEKDIA IEQERNARYR PPKILEPTTF QEPPPKPSRP

KYRPPPQTNL LAPKLQFQVP EGLCASSPTL TSPMEYPSPV

NSLHTPPLHR HNVFKRHSMR EEDFIRPSSR EEAQQLWEAE

KIKMKQVLER QQKQMVEDSQ WLRREERCLD PMVYMNDKSP

LTPEKEAGYT EFTGPPQKPP RLGAQSIQPT ANLDRTDDLV

YHNVMTLVEA VLELKNKLGQ LPPEDYVVVV KNVGLNLRKL

IGSVDDLLPS LPASSRTEIE GTQKLLNKDL AELINKMKLA

QQNAVTSLSE DCKRQMLTAS HTLAVDAKNL LDAVDQAKVV

ANLAHPPAE

SEQ ID NO: 2: amino acid sequence of the human
PYK2 protein
MSGVSEPLSR VKLGTLRRPE GPAEPMVVVP VDVEKEDVRI

LKVCFYSNSF NPGKNFKLVK CTVQTEIREI ITSILLSGRI

GPNIRLAECY GLRLKHMKSD EIHWLHPQMT VGEVQDKYEC

LHVEAEWRYD LQIRYLPEDF MESLKEDRTT LLYFYQQLRN

DYMQRYASKV SEGMALQLGC LELRRFFKDM PHNALDKKSN

FELLEKEVGL DLFFPKQMQE NLKPKQFRKM IQQTFQQYAS

LREEECVMKF FNTLAGFANI DQETYRCELI QGWNITVDLV

IGPKGIRQLT SQDAKPTCLA EFKQIRSIRC LPLEEGQAVL

QLGIEGAPQA LSIKTSSLAE AENMADLIDG YCRLQGEHQG

SLIIHPRKDG EKRNSLPQIP MLNLEARRSH LSESCSIESD

IYAEIPDETL RRPGGPQYGI AREDVVLNRI LGEGFFGEVY

EGVYTNHKGE KINVAVKTCK KDCTLDNKEK FMSEAVIMKN

LDHPHIVKLI GIIEEEPTWI IMELYPYGEL GHYLERNKNS

LKVLTLVLYS LQICKAMAYL ESINCVHRDI AVRNILVASP

ECVKLGDFGL SRYIEDEDYY KASVTRLPIK WMSPESINFR

RFTTASDVWM FAVCMWEILS FGKQPFFWLE NKDVIGVLEK

GDRLPKPDLC PPVLYTLMTR CWDYDPSDRP RFTELVCSLS

DVYQMEKDIA MEQERNARYR TPKILEPTAF QEPPPKPSRP

KYRPPPQTNL LAPKLQFQVP EGLCASSPTL TSPMEYPSPV

NSLHTPPLHR HNVFKRHSMR EEDFIQPSSR EEAQQLWEAE

KVKMRQILDK QQKQMVEDYQ WLRQEEKSLD PMVYMNDKSP

LTPEKEVGYL EFTGPPQKPP RLGAQSIQPT ANLDRTDDLV

YLNVMELVRA VLELKNELCQ LPPEGYVVVV KNVGLTLRKL

IGSVDDLLPS LPSSSRTEIE GTQKLLNKDL AELINKMRLA

QQNAVTSLSE ECKRQMLTAS HTLAVDAKNL LDAVDQAKVL

ANLAHPPAE
```

In some embodiments, the vector of the present invention comprises a nucleic acid molecule encoding for a PYK2 polypeptide comprising an amino acid sequence having at least 90% of identity with the sequence as set forth in SEQ ID NO:1 or 2.

According to the invention a first amino acid sequence having at least 90% of identity with a second amino acid sequence means that the first sequence has 90; 91; 92; 93; 94; 95; 96; 97; 98; 99 or 100% of identity with the second amino acid sequence.

Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989;

Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

As used herein, the term "nucleic acid molecule" has its general meaning in the art and refers to a DNA or RNA molecule. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

In some embodiments, the nucleic acid molecule of the present invention comprises a sequence having at least 70% of identity with the nucleic acid sequence as set forth in SEQ ID NO:3, or SEQ ID NO:4.

According to the invention a first nucleic acid sequence having at least 70% of identity with a second nucleic acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99 or 100% of identity with the second nucleic acid sequence.

SEQ ID NO: 3: nucleic acid sequence encoding for the murine form of the PYK2:

atgtccggggtgtctgagcccttgagccgtgtaaaagtgggcactttacg ccggcctgagggcccccagagccatggtggtggtaccagtggatgtgga gaaggaagacgtgcgcatcctcaaggtctgcttctacagcaacagcttca acccagggaagaacttcaagcttgtcaaatgcacagtgcagacagagatc caggagatcatcacctccatcctcctgagtgggcgaataggcccaacat ccagctggctgaatgctatgggctgaggctgaagcacatgaagtcagacg agatccactggctgcacccacagatgaccgtgggcgaagtgcaggacaag tatgaatgtctacacgtggaagctgagtggaggtatgaccttcaaatccg ctacttgccggaagacttcatggagagcctgaaagaagacaggaccacat tgctgtacttttatcaacagctccggaatgactacatgcaacgctacgcc agcaaggtcagtgaaggcatggctctgcagctgggctgtctggagctcag gagattcttcaaggacatgccccacaatgcactggacaaaaagtccaact ttgaactcctggaaaaagaagtcggtctggacctgttttttcccaaagcag atgcaggaaaacttaaagcccaagcagttccggaagatgatccagcagac cttccagcagtatgcatcactccgggaggaagagtgtgtcatgaaattct tcaatacccctagcgggctttgccaacattgaccaggagacctaccgctgc gaactcattcaaggatggaacattactgtggacctggtcatcggccctaa aggcatccgtcagctgacaagtcaagatacaaagcccacctgcctggccg agtttaagcagatcaaatccatcaggtgcctcccattggaagagacccag gcagtcctgcagctgggcatcgagggtgccccccagtccttgtctatcaa aacgtcgtccctggcagaggctgagaacatggctgacctcatagatggct actgcaggctgcaaggagaacataagggctctctcatcatgcatgccaag aaagatggtgagaagaggaacagcctgcctcagatccccacactaaacct ggaggctcggcggtcgcacctctcagaaagctgcagcatagagtcagaca tctatgcggagattcccgatgagaccctgcgaagaccaggaggtccacag tacggtgttgcccgtgaagaagtagttctaaccgcattctgggtgaaggc ttctttggggaggtctatgaaggtgtctacacgaaccacaaaggggaaaa attaatgtggccgtcaagacctgtaagaaagactgtacccaggacaacaa ggagaagttcatgagtgaggcagtgatcatgaagaatcttgaccaccctc acatcgtgaagctgattggcatcattgaagaggaacccacctggattatc atggaactgtatccttatggggagctgggacactacctggaacgaaataa aaactccctgaaggtacccactctggtcctgtacaccctacagatatgca aagccatggcctatctggagagcatcaactgtgtgcacagggatattgct gtccggaacatcctggtggcctctcctgagtgtgtgaagctgggggactt tgggctctcccggtacattgaggacgaagactattacaaagcctctgtga cccgtctacccatcaaatggatgtccccccgagtccatcaacttccgccgc ttcacaaccgccagtgatgtctggatgtttgctgtatgcatgtgggagat cctcagctttgggaagcagccttcttctggctcgaaaataaggatgtca tcggagtgctggagaaaggggacaggctgcccaagcccgaactctgtccg cctgtccttacacactcatgactcgctgctgggactacgaccccagtga -continued ccggccccgcttcacggagcttgtgtgcagcctcagtgacatttatcaga tggagaaggacattgccatagagcaagaaaggaatgctcgctaccgaccc ccaaaatattggagcctactacctttcaggaaccccacccaagcccagc cggcccaagtacagacctcctccacagaccaacctgctggctcctaagct gcagttccaggtccctgagggtctgtgtgccagctctcctacgcttacca gccctatggagtatccatctccagttaactcgctacacaccccacctctc caccggcacaatgtcttcaagcgccacagcatgcgggaggaggacttcat ccggcccagtagccgagaagaggcccagcagctctgggaggcagagaaga tcaagatgaagcaggtcctagaaagacagcagaagcagatggtggaagat tcccagtggctgaggcgagaggaaagatgcttggaccctatggtttatat gaatgacaagtccccactgactccagagaaggaggccggctacacggagt tcacagggcccccacagaaaccacctcggctcggtgcacagtccattcag cccacagccaacctggacaggaccgatgacctcgtgtaccacaatgtcat gaccctggtggaggctgtgctggaactcaagaacaagcttggccagttgc cccctgaggactatgtggtggtggtgaagaacgtggggctgaacctgcgg aagctcatcggcagtgtggacgatctcttgccctccttgccggcatcttc gaggacagagattgaagggacccagaaactgctcaacaaagacctggcag agctcatcaacaagatgaagttggctcagcagaacgccgtgacgtccctg agtgaggactgcaagcggcagatgctcacagcgtcccataccctggctgt ggatgccaagaacctgctggatgctgtggaccaagccaaggttgtggcta atctggcccacccgcctgcagagtga SEQ ID NO: 4: nucleic acid sequence encoding for the human form of the PYK2:
atgtctggggtgtccgagcccctgagccgagtaaagttgggcacattacg ccggcctgaaggccctcagagcccatggtggtggtaccagtagatgtgga aaaggaggacgtgcgtatcctcaaggtctgcttctatagcaacagcttca atcctgggaagaacttcaaactggtcaaatgcactgtccagacggagatc cgggagatcatcacctccatcctgctgagcgggcggatcgggcccaacat ccggttggctgagtgctatgggctgaggctgaagcacatgaagtccgatg agatccactggctgcacccacagatgacggtgggtgaggtgcaggacaag tatgagtgtctgcacgtggaagccgagtggaggtatgaccttcaaatccg ctacttgccagaagacttcatggagagcctgaaggaggacaggaccacgc tgctatattttaccaacagctccggaacgactacatgcagcgctacgcc agcaaggtcagcgagggcatggcccctgcagctgggctgcctggagctcag gcggttcttcaaggatatgccccacaatgcacttgacaagaagtccaact tcgagctcctagaaaaggaagtggggctggacttgttttcccaaagcag atgcaggagaacttaaagcccaaacagttccggaagatgatccagcagac cttccagcagtacgcctcgctcagggaggaggagtgcgtcatgaagttct tcaacactctcgccggcttcgccaacatcgaccaggagacctaccgctgt gaactcattcaaggatggaacattactgtggacctggtcattggcccctaa agggatccgccagctgactagtcaggacgcaaagcccacctgcctggccg agttcaagcagatcaggtccatcaggtgcctcccgctggaggagggccag gcagtacttcagctgggcattgaaggtgcccccaggccttgtccatcaa aacctcatccctagcagaggctgagaacatggctgacctcatagacggct actgccggctgcagggtgagcaccaaggctctctcatcatccatcctagg aaagatggtgagaagcggaacagcctgccccagatccccatgctaaacct ggaggcccggcggtcccacctctcagagagctgcagcatagagtcagaca tctacgcagagattcccgacgaaaccctgcgaaggcccggaggtccacag tatggcattgcccgtgaagatgtggtcctgaatcgtattcttggggaagg ctttttttggggaggtctatgaaggtgtctacacaaatcacaaaggggaga aaatcaatgtagctgtcaagacctgcaagaaagactgcactctggacaac aaggagaagttcatgagcgaggcagtgatcatgaagaacctcgaccaccc gcacatcgtgaagctgatcggcatcattgaagaggagcccacctggatca tcatggaattgtatccctatggggagctgggccactacctggagcggaac aagaactccctgaaggtgctcacccctcgtgctgtactcactgcagatatg caaagccatggcctacctggagagcatcaactgcgtgcacagggacattg ctgtccggaacatcctggtggcctcccctgagtgtgtgaagctgggggac tttggtctttcccggtacattgaggacgaggactattacaaagcctctgt gactcgtctccccatcaaatggatgtccccagagtccattaacttccgac gcttcacgacagccagtgacgtctggatgttcgccgtgcatgtgggag atcctgagctttgggaagcagcccttcttctggctggagaacaaggatgt catcgggggctgagaaaggagaccggctgcccaagcctgatctctgtc caccggtcctttataccctcagtgacccgctgctgggactacgaccccag tgaccggccccgcttcacggagctggtgtgcagcctcagtgacgtttatc agatggagaaggacattgccatggagcaagagaggaatgctcgctaccga accccaaaatcttggagcccacagccttccaggaaccccacccaagcc agccgacctaagtacagaccccctccgcaaaccaacctcctggctccaa agctgcagttccaggttcctgagggtctgtgtgccagctctcctacgctc accagccctatggagtatccatctcccgttaactcactgcacaccccacc tctccaccggcacaatgtcttcaaacgccacagcatgcgggaggaggact tcatccaacccagcagccgagaagaggcccagcagctgtgggaggctgaa aaggtcaaaatgcggcaaatcctggacaaacagcagaagcagatggtgga ggactaccagtggctcaggcaggaggagaagtccctggaccccatggttt atatgaatgataagtccccattgacgccagagaaggaggtcggctacctg gagttcacagggccccacagaagcccccgaggctgggcgcacagtccat ccagcccacagctaacctggaccggaccgatgacctggtgtacctcaatg tcatggagctggtgcgggccgtgctggagctcaagaatgagctctgtcag ctgccccccgagggctacgtggtggtggtgaagaatgtggggctgaccct gcggaagccatcgggagcgtggatgatctcctgcctccttgccgtcatc ttcacggacagagatcgagggcacccagaaactgctcaacaaagacctgg cagagctcatcaacaagatgcggctggcgcagcagaacgccgtgacctcc ctgagtgaggagtgcaagaggcagatgctgacggcttcacacacccctggc -continued

```
tgtggacgccaagaacctgctcgacgctgtggaccaggccaaggttctgg ccaatctggcccacccacctgcagagtga
```

As used herein, the term "vector" has its general meaning in the art and refers to the vehicle by a nucleic acid molecule can be introduced into a host cell, so as to transform the host and promote expression (e.g. transcription and translation) of the introduced sequence. The terms "Gene transfer" or "gene delivery" refer to methods or systems for reliably inserting foreign DNA into host cells. Such methods can result in transient expression of non-integrated transferred DNA, extrachromosomal replication and expression of transferred replicons (e.g. episomes), or integration of transferred genetic material into the genomic DNA of host cells. Cells could be hematopoietic stem cells (e.g. CD34+ cell fraction) or hematopoietic progenitor cells (particularly monocytic progenitors or microglia precursors) isolated from the bone marrow or the blood of the patient (autologous) or from a donor (allogeneic) genetically modified to stably express PYK2 or a fragment derived from it by transduction with a vector, particularly a lentiviral vector expressing PYK2 under the control of a non-specific (e.g.: phosphoglycerate kinase, EF1alpha) or specific (monocytic-macrophage or microglia specific e.g. CD68 or CD11b) native or modified promoter.

In some embodiments, the vector of the present invention is a non-viral vector. Typically, the non-viral vector may be a plasmid which includes the nucleic acid molecule of the present invention.

In some embodiments, the vector of the present invention is a viral vector. Gene delivery viral vectors useful in the practice of the present invention can be constructed utilizing methodologies well known in the art of molecular biology. Typically, viral vectors carrying transgenes are assembled from polynucleotides encoding the transgene, suitable regulatory elements and elements necessary for production of viral proteins which mediate cell transduction. Examples of viral vector include but are not limited to adenoviral, retroviral, lentiviral, herpesvirus and adeno-associated virus (AAV) vectors.

In some embodiments, the vector of the present invention is an adeno-associated viral (AAV) vector. By an "AAV vector" is meant a vector derived from an adeno-associated virus serotype, including without limitation AAV1, AAV2, AAV3, AAV4, AA5, AAV6, AAV7, AAV8, AAV9, AAVrh10 or any other serotypes of AAV that can infect humans, monkeys or other species. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g. by the insertion, deletion or substitution of nucleotides, so long as the sequences provide for functional rescue, replication and packaging. AAV expression vectors are constructed using known techniques to at least provide as operatively linked components in the direction of transcription, control elements including a transcriptional initiation region, the nucleic acid molecule of the present invention and a transcriptional termination region. The control elements are selected to be functional in a mammalian cell. The resulting construct which contains the operatively linked components is bounded (5' and 3') with functional AAV ITR sequences. By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. See, e.g., Kotin, 1994; Berns, K I "Parvoviridae and their Replication" in Fundamental Virology, 2nd Edition, (B. N. Fields and D. M. Knipe, eds.) for the AAV-2 sequence. As used herein, an "AAV ITR" does not necessarily comprise the wild-type nucleotide sequence, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAV-6, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Additionally, AAV ITRs may be derived from any of several AAV serotypes, including without limitation, AAV-1, AAV-2, AAV-3, AAV-4, AAV 5, AAV-6, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell. In some embodiments, the AAV vector of the present invention is selected from vectors derived from AAV serotypes having tropism for and high transduction efficiencies in cells of the mammalian central and peripheral nervous system, particularly neurons, neuronal progenitors, astrocytes, oligodendrocytes and glial cells. In some embodiments, the AAV vector is an AAV4, AAV9 or an AAVrh10 that have been described to well transduce brain cells especially neurons. In some embodiments, the AAV vector of the present invention is a double-stranded, self-complementary AAV (scAAV) vector. Alternatively to the use of single-stranded AAV vector, self-complementary vectors can be used. The efficiency of AAV vector in terms of the number of genome-containing particles required for transduction, is hindered by the need to convert the single-stranded DNA (ssDNA) genome into double-stranded DNA (dsDNA) prior to expression. This step can be circumvented through the use of self-complementary vectors, which package an inverted repeat genome that can fold into dsDNA without the requirement for DNA synthesis or base-pairing between multiple vector genomes. Resulting self-complementary AAV (scAAV) vectors have increased resulting expression of the transgene. For an overview of AAV biology, ITR function, and scAAV constructs, see McCarty D M. Self-complementary AAV vectors; advances and applications. Mol. Ther. 2008 October; 16 (10): at pages 1648-51, first full paragraph, incorporated herein by reference for disclosure of AAV and scAAV constructs, ITR function, and role of ΔTRS ITR in scAAV constructs. A rAAV vector comprising a ΔTRS ITR cannot correctly be nicked during the replication cycle and, accordingly, produces a self-complementary, double-stranded AAV (scAAV) genome, which can efficiently be packaged into infectious AAV particles. Various rAAV, ssAAV, and scAAV vectors, as well as the advantages and drawbacks of each class of vector for specific applications and methods of using such vectors in gene transfer applications are well known to those of skill in the art (see, for example, Choi V W, Samulski R J, McCarty D M. Effects of adeno-associated virus DNA hairpin structure on recombination. J. Virol. 2005 June; 79(11):6801-7; McCarty D M, Young S M Jr, Samulski R J. Integration of adeno-associated virus (AAV) and recombinant AAV vectors. Annu Rev Genet. 2004; 38:819-45; McCarty D M, Monahan P E, Samulski R J. Self-complementary recombinant adeno-associated virus (scAAV) vectors promote efficient transduction independently of DNA synthesis. Gene Ther. 2001 August; 8(16):1248-54; and McCarty D M. Self-complementary AAV vectors; advances and applications. Mol. Ther. 2008 October; 16(10):1648-56; all references cited in this application are incorporated herein by reference for disclosure of AAV, rAAV, and scAAV vectors).

The AAV vector of the present invention can be constructed by directly inserting the selected sequence (s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g. U.S. Pat. Nos. 5,173,414 and 5,139,941; International Publications Nos. WO 92/01070 (published 23 Jan. 1992) and WO 93/03769 (published 4 Mar. 1993); Lebkowski et al., 1988; Vincent et al., 1990; Carter, 1992; Muzyczka, 1992; Kotin, 1994; Shelling and Smith, 1994; and Zhou et al., 1994. Alternatively, AAV ITRs can be excised from the viral genome or from an AAV vector containing the same and fused 5' and 3' of a selected nucleic acid construct that is present in another vector using standard ligation techniques. AAV vectors which contain ITRs have been described in, e.g. U.S. Pat. No. 5,139,941. In particular, several AAV vectors are described therein which are available from the American Type Culture Collection ("ATCC") under Accession Numbers 53222, 53223, 53224, 53225, and 53226. Additionally, chimeric genes can be produced synthetically to include AAV ITR sequences arranged 5' and 3' of one or more selected nucleic acid sequences. Preferred codons for expression of the chimeric gene sequence in mammalian CNS and PNS cells can be used. The complete chimeric sequence is assembled from overlapping oligonucleotides prepared by standard methods. See, e.g., Edge, 1981; Nambair et al., 1984; Jay et al., 1984. In order to produce AAV virions, an AAV expression vector is introduced into a suitable host cell using known techniques, such as by transfection. A number of transfection techniques are generally known in the art. See, e.g., Graham et al., 1973; Sambrook et al. (1989) Molecular Cloning, a laboratory manual, Cold Spring Harbor Laboratories, New York, Davis et al. (1986) Basic Methods in Molecular Biology, Elsevier, and Chu et al., 1981. Particularly suitable transfection methods include calcium phosphate co-precipitation (Graham et al., 1973), direct microinjection into cultured cells (Capecchi, 1980), electroporation (Shigekawa et al., 1988), liposome mediated gene transfer (Mannino et al., 1988), lipid-mediated transduction (Felgner et al., 1987), and nucleic acid delivery using high-velocity microprojectiles (Klein et al., 1987).

Typically the vector of the present invention comprises an expression cassette. The term "expression cassette", as used herein, refers to a nucleic acid construct comprising nucleic acid elements sufficient for the expression of the nucleic acid molecule of the present invention. Typically, an expression cassette comprises the nucleic acid molecule of the present invention operatively linked to a promoter sequence. The term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (e.g., the coding sequence is under the transcriptional control of the promoter). Encoding sequences can be operatively linked to regulatory sequences in sense or antisense orientation. In some embodiments, the promoter is a heterologous promoter. The term "heterologous promoter", as used herein, refers to a promoter that is not found to be operatively linked to a given encoding sequence in nature. In some embodiments, an expression cassette may comprise additional elements, for example, an intron, an enhancer, a polyadenylation site, a woodchuck response element (WRE), and/or other elements known to affect expression levels of the encoding sequence. As used herein, the term "promoter" refers to a nucleotide sequence capable of controlling the expression of a coding sequence or functional RNA. In general, the nucleic acid molecule of the present invention is located 3' of a promoter sequence. In some embodiments, a promoter sequence consists of proximal and more distal upstream elements and can comprise an enhancer element. An "enhancer" is a nucleotide sequence that can stimulate promoter activity and may be an innate element of the promoter or a heterologous element inserted to enhance the level or tissue-specificity of a promoter. In some embodiments, the promoter is derived in its entirety from a native gene. In some embodiments, the promoter is composed of different elements derived from different naturally occurring promoters. In some embodiments, the promoter comprises a synthetic nucleotide sequence. It will be understood by those skilled in the art that different promoters will direct the expression of a gene in different tissues or cell types, or at different stages of development, or in response to different environmental conditions or to the presence or the absence of a drug or transcriptional co-factor. Ubiquitous, cell-type-specific, tissue-specific, developmental stage-specific, and conditional promoters, for example, drug-responsive promoters (e.g. tetracycline-responsive promoters) are well known to those of skill in the art. Examples of promoter include, but are not limited to, the CamKII promoter, the phophoglycerate kinase (PKG) promoter, CAG (composite of the CMV enhancer the chicken beta actin promoter (CBA) and the rabbit beta globin intron.), NSE (neuronal specific enolase), synapsin or NeuN promoters, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), SFFV promoter, rous sarcoma virus (RSV) promoter, synthetic promoters, hybrid promoters, and the like. The promoters can be of human origin or from other species, including from mice. In addition, sequences derived from non-viral genes, such as the murine metallothionein gene, will also find use herein. Such promoter sequences are commercially available from, e.g. Stratagene (San Diego, Calif.).

In some embodiments, the vector of the present invention comprises the nucleic acid sequence set forth in SED ID NO:5.

SEQ ID NO: 5: complete sequence of the expression cassette of the AAV transfer vector encoding codon-optimized mouse PYK2 (AAV-CaMKII-EGFP-T2A-mPTK2B)

```
cctgcaggca gctgcgcgct cgctcgctca ctgaggccgc ccgggcaaag cccgggcgtc gggcgacctt tggtcgcccg
gcctcagtga gcgagcgagc gcgcagagag ggagtggcca actccatcac tagggggtcc tgcggccaat tcagtcgata
actataacgg tcctaaggta gcgatttaaa tacgcgctct cttaaggtag ccccgggacg cgtcaattga gcgatgatca
cttgtggact aagtttgttc gcatccccct ctccaacccc ctcagtacat caccctgggg gaacagggtc cacttgctcc
tgggcccaca cagtcctgca gtattgtgta tataaggcca gggcaaagag gagcaggttt taaagtgaaa ggcaggcagg
tgttggggag gcagttaccg gggcaacggg aacagggcgt tcggaggtg gttgccatgg ggacctggat gctgacgaag
gctcgcgagc tgtgagcag ccacagtgcc ctgctcagaa gccccaagct cgtcagtcaa gccggttctc cgtttgcact
caggagcacg ggcaggcgag tggcccctag ttctgggggc agcgctagcg tttaaactta agcttggtac cggccgctgc
ggccctcgag caagctggct agttaagcta tcaacaagtt tgtataaaaa agcaggcttt aaaggaacca attcagtcga
cgctagctcg ccaccatggt gagcaaggc gaggagctgt tcaccggggt ggtgcccatc ctggtcgagc tggacggcga
cgtaaacggc cacaagttca gcgtgtccgg cgagggcgag ggcgatgcca cctacggcaa gctgaccctg aagttcatct
gcaccaccgg caagctgccc gtgccctggc ccaccctcgt gaccaccctg acctacggcg tgcagtgctt cagccgctac
cccgaccaca tgaagcagca cgacttcttc aagtccgcca tgcccgaagg ctacgtccag gagcgcacca tcttcttcaa
ggacgacggc aactacaaga cccgcgccga ggtgaagttc gagggcgaca ccctggtgaa ccgcatcgag ctgaagggca
tcgacttcaa ggaggacggc aacatcctgg ggcacaagct ggagtacaac tacaacagcc acaacgtcta tatcatggcc
gacaagcaga agaacggcat caaggtgaac ttcaagatcc gccacaacat cgaggacggc agcgtgcagc tcgccgacca
ctaccagcag aacacccca tcggcgacgg ccccgtgctg ctgcccgaca ccactacct gagcacccag tccgccctga
gcaaagaccc caacgagaag cgcgatcaca tggtcctgct ggagttcgtg accgccgccg ggatcactct cggcatggac
gagctgtaca agggatccgg cagtggagag ggcagaggaa gtctgctaac atgcggtgac gtcgaggaga tcctggccc
aagatctatg tccggggtgt ctgagcccttt gagccgtgta aaagtgggca ctttacgccg gctgagggc cccccagagc
ccatggtggt ggtaccagtg gatgtggaga aggaagacgt gcgcatcctc aaggtctgct tctacagcaa cagcttcaac
ccagggaaga acttcaagct tgtcaaatgc acagtgcaga cagagatcca ggagatcatc acctccatcc tcctgagtgg
gcgaatagg ccaacatcc agctggctga atgctatggg ctgaggctga agcacatgaa gtcagacgag atccactggc
tgcacccaca tgaccgtg gggcgaagtg caggacaagta tgaatgctc acgtggaag ctgagtggag gtatgacctt
caaatccgct acttgccgga agacttcatg gagagcctga aagaagacag gaccacattg ctgtacttt atcaacagct
ccggaatgac tacatgcaac gctacgccag caaggtcagt gaaggcatgg ctctgcagct gggctgtctg gagctcagga
gattcttcaa ggacatgccc cacaatgcac tggacaaaaa gtccaacttt gaactcctgg aaaagagagt cggtctggac
ctgtttttcc caaagcagat gcaggaaaac ttaaagccca agcagttccg gaagatgatc cagcagacct tccagcagta
tgcatcactc cggggaggaag agtgtgtcat gaaattcttc aataccctag cgggctttgc caacattgac caggagacct
accgctgcga actcattcaa ggatggaaca ttactgtgga cctggtcatc ggccctaaag catccgtca gctgacaagt
caagatacaa agcccacctg cctggccgag tttaagcaga tcagatccat caggtgcctc ccattggaag agacccaggc
agtcctgcag ctgggcatcg agggtgcccc ccagtccttg tctatcaaaa cgtcgtccct ggcagaggct gagaacatgg
ctgatctcat agatggctac tgcaggctgc aaggagaaca taagggctct ctcatcatgc atgccaagaa agatggtgag
aagaggaaca gcctgcctca gatccccaca ctaaacctgg aggctcggcg gtcgcacctc tcagaaagct gcagcataga
gtcagacatc tatgcggaga ttcccgatga ccctgcga agaccaggag gtccacagta cggtgttgcc cgtgaagaag
tagttcttaa ccgcattctg ggtgaaggct ctttggggga ggtctatgaa ggtgtctaca cgaaccacaa aggggaaaaa
attaatgtgc ccgtcaagac ctgtaagaaa gactgtaccc aggacaacaa ggagaagttc atgagtgagg cagtgatcat
gaagaatctt gaccaccctc acatcgtgaa gctgattggc atcattgaag aggaacccac ctggattatc atggaactgt
atccttatgg ggagctggga cactacctgg aacgaaataa aaactccctg aaggtaccca ctctggtcct gtacacccta
cagatatgca aagccatggc ctatctggag agcatcaact gtgtgcacag ggatattgct gtccggaaca tcctggtggc
```

-continued

```
ctctcctgag tgtgtgaagc tgggggactt tgggctctcc cggtacattg aggacgaaga ctattacaaa gcctctgtga cacgtctacc catcaaatgg atgtcccccg agtccatcaa cttccgccgc ttcacaaccg ccagtgatgt ctggatgttt gctgtatgca tgtgggagat cctcagcttt gggaagcagc cttctttctg gctcgaaaat aaggatgtca tcggagtgct ggagaaaggg gacaggctgc ccaagcccga actctgtccg cctgtccttt acacactcat gactcgctgc tgggactacg accccagtga ccggccccgc ttcacggagc ttgtgtgcag cctcagtgac atttatcaga tggagaagga cattgccata gagcaagaaa ggaatgctcg ctaccgaccc cctaaaatat tggagcctac tacctttcag gaacccccac ccaagcccag ccggcccaag tacagacctc ctccacagac caacctgctg gctcctaagc tgcagttcca ggtccctgag ggtctgtgtg ccagctctcc tacgcttacc agccctatgg agtatccatc tccagttaac tcgctgcaca cccacctct ccaccggcac aatgtcttca agcgccacag catgcgggag gaggacttca tccggcccag tagccgagaa gaggcccagc agctctggga ggcagagaag atcaagatga agcaggtcct agaaagacag cagaagcaga tggtggaaga ttcccagtgg ctgaggcgag aggaaagatg cttggaccct atggtttata tgaatgacaa gtccccactg actccagaga aggaggccgg ctacacggag ttcacagggc ccccacagaa accacctcgg ctcggtgcac agtccattca gcccacagcc aacctggaca ggaccgatga cctcgtgtac cacaatgtca tgaccctggt ggaggctgtg ctggaactca agaacaagct tggccagttg cccctgagg actatgtggt ggtggtgaag aacgtgggc tgaacctgcg gaagctcatc ggcagtgtgg acgatctctt gccctccttg ccggcatctt cgaggacaga gattgaaggg acccagaaac tgctcaacaa agacctggca gagctcatca acaagatgaa gttggctcag cagaacgccg tgacgtccct gagtgaggac tgcaagcggc agatgctcac agcgtcccat accctggctg tggatgccaa gaacctgctg gatgctgtgg accaagccaa ggttgtggct aatctggccc acccgcctgc agagtgagcg gccgcctcga gtctagaccc agctttcttg tataaagtgg ttgatctaga gggcccgtaa ctagttgaca tatgaccggt tagtaatgag tttatccagc acagtggcgg ccgctcgagt ctagagggcc cttcgaaggt aagcctatcc ctaaccctct cctcggtctc gattctacgc gtaccggtca tcatcaccat caccattgag tttaaacccg ctgatcagcc tcgactgtgc cttctagttg ccagccatct gttgtttgcc cctcccccgt gccttccttg accctggaag gtgccactcc cactgtcctt tcctaataaa atgaggaaat tgcatcgcat tgtctgagta ggtgtcattc tattctgggg ggtggggtgg ggcaggacag caagggggag gattgggaag acaatagcag gcatgctggg gatgcggtgg gctctatggc ttctgaggcg gaaagaacca gatcctctct taaggtagca tcgagattta aattagggat aacagggtaa tggcgcgggc cgcaggaacc cctagtgatg gagttggcca ctccctctct gcgcgctcgc tcgctcactg aggccgggcg accaaaggtc gcccgacgcc cgggctttgc ccgggcggcc tcagtgagcg agcgagcgcg cagctgcctg caggggcgcc tgatgcggta ttttctcctt acgcatctgt gcggtatttc acaccgcata cgtcaaagca accatagtac gcgccctgta gcggcgcatt aagcgcggcg ggtgtggtgg ttacgcgcag cgtgaccgct acacttgcca gcgccctagc gcccgctcct ttcgctttct tcccttcctt tctcgccacg ttcgccggct ttccccgtca agctctaaat cgggggctcc ctttagggtt ccgatttagt gctttacggc acctcgaccc caaaaaactt gatttgggtg atggttcacg tagtgggcca tcgccctgat agacggtttt tcgccctttg acgttggagt ccacgttctt taatagtgga ctcttgttcc aaactggaac aacactcaac cctatctcgg gctattcttt tgatttataa gggattttgc cgatttcggc ctattggtta aaaaatgagc tgatttaaca aaaatttaac gcgaatttta acaaaatatt aacgtttaca atttatggt gcactctcag tacaatctgc tctgatgccg catagttaag ccagccccga cacccgccaa cacccgctga cgcgccctga cgggcttgtc tgctcccggc atccgcttac agacaagctg tgaccgtctc cgggagctgc atgtgtcaga ggttttcacc gtcatcaccg aaacgcgcga gacgaaaggg cctcgtgata cgcctatttt tataggttaa tgtcatgata ataatggttt cttagacgtc aggtggcact tttcgggaa atgtgcgcgg aacccctatt tgtttatttt tctaaataca ttcaaatatg tatccgctca tgagacaata accctgataa atgcttcaat aatattgaaa aaggaagagt atgagtattc aacatttccg tgtcgccctt attccctttt ttgcggcatt ttgccttcct gttttgctc acccagaaac gctggtgaaa gtaaaagatg ctgaagatca gttgggtgca cgagtgggtt acatcgaact ggatctcaac agcggtaaga tccttgagag ttttcgcccc gaagaacgtt ttccaatgat gagcactttt aaagttctgc tatgtggcgc ggtattatcc
```

-continued

```
cgtattgacg ccgggcaaga gcaactcggt cgccgcatac actattctca gaatgacttg gttgagtact caccagtcac agaaaagcat cttacggatg gcatgacagt aagagaatta tgcagtgctg ccataaccat gagtgataac actgcggcca acttacttct gacaacgatc ggaggaccga aggagctaac cgcttttttg cacaacatgg gggatcatgt aactcgcctt gatcgttggg aaccggagct gaatgaagcc ataccaaacg acgagcgtga caccacgatg cctgtagcaa tggcaacaac gttgcgcaaa ctattaactg gcgaactact tactctagct tcccggcaac aattaataga ctggatggag gcggataaag ttgcaggacc acttctgcgc tcggcccttc cggctggctg gtttattgct gataaatctg gagccggtga gcgtgggtct cgcggtatca ttgcagcact ggggccagat ggtaagccct cccgtatcgt agttatctac acgacgggga gtcaggcaac tatggatgaa cgaaatagac agatcgctga gataggtgcc tcactgatta agcattggta actgtcagac caagtttact catatatact ttagattgat ttaaaacttc attttaatt taaaaggatc taggtgaaga tccttttga taatctcatg accaaaatcc cttaacgtga gttttcgttc cactgagcgt cagacccgt agaaaagatc aaaggatctt cttgagatcc ttttttctg cgcgtaatct gctgcttgca aacaaaaaaa ccaccgctac cagcggtggt ttgtttgccg gatcaagagc taccaactct ttttccgaag gtaactggct tcagcagagc gcagatacca aatactgtcc ttctagtgta gccgtagtta ggccaccact tcaagaactc tgtagcaccg cctacatacc tcgctctgct aatcctgtta ccagtggctg ctgccagtgg cgataagtcg tgtcttaccg ggttggactc aagacgatag ttaccggata aggcgcagcg tcgggctga acggggggtt cgtgcacaca gcccagcttg gagcgaacga cctacaccga actgagatac ctacagcgtg agctatgaga aagcgccacg cttcccgaag ggagaaaggc ggacaggtat ccggtaagcg gcagggtcgg aacaggagag cgcacgaggg agcttccagg gggaaacgcc tggtatcttt atagtcctgt cgggtttcgc cacctctgac ttgagcgtcg attttgtga tgctcgtcag ggggcggag cctatggaaa aacgccagca acgcggcctt tttacggttc ctggccttt gctggccttt tgctcacatg t (7841)
```

(m) CaMKII(0.4) (−273/+101): 230-603
EGFP-T2A-mPTK2B: 736-4557
EGFP: 736-1452
T2A: 1459-1521
mPTK2B: 1528-4557
bGH poly(A): 4792-5019
right inverted terminal repeat 5104-5244
ampicillin resistance (bla) ORF 6161-7018
pUC origin 7169-7836

The expression cassette of the AAV transfer vector encoding codon-optimized human PYK2 could be the same as SEQ ID No. 5 with substitution of the murine PYK2 coding sequence with the human PYK2 coding sequence (see seq ID No 4) and also the human CaMKIIα promoter sequence (available in switchgeargenomics (Product ID S705854). Eukaryotic Promoter Database (EPD) allows to reach human CAMK2A promoter sequence: http://epd.vital-it.ch/cgi-bin/get_doc?db=hgEpdNew&format=genome&entry=CAMK2A_1).

By a "therapeutically effective amount" of the vector of the present invention is meant a sufficient amount of the vector for the treatment of neurodegenerative disease. It will be understood, however, that the total daily usage of the vector of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific vector employed; and like factors well known in the medical arts. For example, it is well within the skill of the art to start doses of the compound at levels lower than those required to achieve the desired therapeutic effect and to gradually increase the dosage until the desired effect is achieved. Typically, from $10^8$ to $10^{10}$ viral genomes (vg) are administered per dose in mice. Typically, the doses of AAV vectors to be administered in humans may range from $10^{10}$ to $10^{12}$ vg.

Typically, the vector or the cell of the present invention are delivered directly and specifically into selected brain regions by intracerebral injections into, the striatum, the cerebral cortex and particularly the entorhinal cortex, or the hippocampus. In some embodiments, the vector of the present invention or the cells transduced with the vector is delivered by intrathecal delivery. In some embodiments, the vector of the present invention of the cells are delivered into the brain by intracerebral injection and/blood by intravenously injection, in the spinal fluid by intrathecal delivery, by or intracerebroventricular injection or by intra-nasal injection. Particularly, any routes of administration that allow a strong expression of the vector in the spinal cord, brain, including cortex, hippocampus, striatum and other brain regions as determined to be appropriate dentate nucleus can be used in the invention. In some embodiments, the cells are delivered by infusion in the peripheral blood (intravenous or intra-arterial injection) or in the CSF.

In some embodiments, the vector of the present invention is administrated to the subject in need thereof one time, two times, three times or more. In some embodiments, the vector of the present invention is administrated to the subject in need thereof one time and re-administered several months or years later to said subject.

The vectors used herein may be formulated in any suitable vehicle for delivery. For instance they may be placed into a pharmaceutically acceptable suspension, solution or emulsion. Suitable mediums include saline and liposomal preparations. More specifically, pharmaceutically acceptable carriers may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, exosomes and liposomes.

In another aspect, the present invention relates to a method of treating neurodegenerative disease in a subject in need thereof comprising administering to the subject a therapeutically effective amount of cells transduced with a vector which comprises a nucleic acid molecule encoding for a PYK2 polypeptide.

In one embodiment, the cells administrated according to the invention are autologous hematopoietic stem cell or hematopoietic progenitors that could be isolated from the patient, transduced with a vector, particularly a lentiviral vector and reinfused directly or after bone marrow conditioning.

The invention will be further illustrated by the following figures and examples. However, these examples and figures should not be interpreted in any way as limiting the scope of the present invention.

FIGURES

Huntington Study

FIG. 1. Spatial learning and memory, and CA1 long-term potentiation deficits in Pyk2 mutant mice. (a) In the spontaneous alternation test, $Pyk2^{+/+}$, $Pyk2^{+/-}$ and $Pyk2^{-/-}$ 3-month-old mice were placed for 10 min in a Y-maze with one arm closed (upper left panel). Two hours later they were put in the same maze with the new arm (NA) open and the percentage of time exploring the new arm (NA) and the previously explored (old arm OA) was compared (upper right panel). Two-way ANOVA interaction $F_{(2,48)}=11.6$, $p<0.0001$, OA vs NA Holm-Sidak's test, $Pyk2^{+/+}$, $t=4.6$, $p<0.0001$, $Pyk2^{+/-}$, $t=1.58$, $Pyk2^{-/-}$ $t=0.81$. (b) In the novel object location test the percentage of time exploring the displaced object (new location, NL, 24 h after first exposure) and the unmoved object (old location, OL) was compared (upper panels). Two-way ANOVA interaction $F_{(2,50)}=3.41$, $p=0.041$, OL vs NL Holm-Sidak's test, $Pyk2^{+/+}$, $t=3.1$, $p<0.01$, $Pyk2^{+/-}$, $t=0.23$, $Pyk2^{-/-}$ $t=0.14$. In a and b, 7-12 mice were used per genotype; the dotted line indicates the chance level. (c, d) Schaffer collaterals were stimulated in hippocampal slices (1-3 slices per animal) from 3-4-week-old $Pyk2^{+/+}$ (n=5), $Pyk2^{+/-}$ (n=6) and $Pyk2^{-/-}$ (n=4) mice, and field excitatory post-synaptic potentials (fEPSP) were recorded in CA1, before and after high frequency stimulation (HFS, 5×1 s at 100 Hz). (c) Time course of fEPSP slope. Insets show typical traces before (grey) and 40 min after (black) HFS in $Pyk2^{+/+}$ and $Pyk2^{-/-}$ slices. (d) Ten-min average of fEPSP slope 40 minutes after HFS, normalized to the mean of 10-min baseline (corresponding time points are indicated in c by grey and black horizontal lines). Kruskal-Wallis=9.37, p=0.0024, post-hoc analysis with Dunn's multiple comparisons test. (e) Paired-pulse ratio at the same synapses. n=3-5 mice per group, 2-4 slices per mouse. Kruskal-Wallis=15.62, p=0.0004. In a-e values are means+SEM, *p<0.05, p<0.01, *p<0.001.

FIG. 2. Hippocampal proteins phosphorylation and levels in Pyk2-deficient mice.

(a) Densitometry quantification of immunoblotting analysis of Pyk2, the related tyrosine kinase FAK, the active autophosphorylated form of Src-family kinases (pY-SFK, pTyr-420 in Fyn), Fyn, and tubulin as a loading control in 3-month-old $Pyk2^{+/+}$, $Pyk2^{+/-}$ and $Pyk2^{-/-}$ littermates. Data were normalized to tubulin for each sample and expressed as percentage of wild-type. (b) NMDA receptors subunits phosphorylated residues, total levels, and PSD-95 analyzed by immunoblotting were quantified and analyzed as indicated in a. In a and b statistical analysis was done with one-way ANOVA and Holm-Sidak's multiple comparisons test or Kruskal-Wallis and Dunn's test depending on the normality of distribution. (c) Quantification of immunoblots of NMDA receptor subunits and PSD-95 in PSD fraction prepared from hippocampus of Pyk2 +/+ and −/− mice. Data are expressed as a percentage of the mean values in wild type PSDs. Two-tailed Mann and Whitney test (n=7 +/+ and 5 −/−): GluN1, $t_{10}=3.52$, p 0.0056, GluN2A, $t_{10}=2.68$, p=0.023, GluN2B, $t_{10}=2.69$, p=0.022, PSD-95, $t_{10}=2.66$, p=0.024. In a and b, Holm-Sidak's vs. wild type, *p<0.05, p<0.01, *p<0.001, and ****p<$10^{-4}$; significant differences between −/− and −/+ are indicated with °p<0.05, °°p<0.01, and °°°°p<$10^{-4}$. In Dunn's test (b) and Mann and Whitney's test (c), significant differences vs wild type are indicated with #p<0.05, ###p<0.01, and ####p<$10^{-4}$. In all graphs data are means+SEM.

FIG. 3. Pyk2 localization and dendritic spines density and morphology in Pyk2-deficient mice. (a) Quantification of PSD-95-positive puncta in the CA1 stratum radiatum from $Pyk2^{+/+}$ and $Pyk2^{-/-}$ mice. Data are means+SEM (7-10 mice per genotype, 3 quantified sections/mouse). One-way ANOVA $F_{(2,21)}=10.23$, p=0.0008. Holm-Sidak's multiple comparisons test vs +/+, p<0.01, *p<0.001. (b) Quantification of spine density in Golgi-Cox-stained apical dendrites of CA1 stratum radiatum pyramidal neuron from $Pyk2^{+/+}$, $Pyk2^{+/-}$, and $Pyk2^{-/-}$ mice, 3-4 animals/genotype, one-way ANOVA, $F_{(2,146)}=14.95$, p<$10^{-4}$ (n=47-54 dendrites/group), post-hoc analysis with Holm-Sidak's multiple comparisons test vs +/+, p<0.01, **p<$10^{-4}$ and −/− vs −/+, °°p<0.01. (c, d) Cumulative probability of spine head diameter (c, n=80) and spine neck length (d, n=115) in ~60 dendrites from 3-4 animals per genotype. Distributions were compared with the Kolmogorov-Smirnov test: spine head diameter no significant difference, neck length +/+ vs +/−, D=0.108, p=0.04, +/+ vs −/−, D=0.154, p=0.0005. In a and b, data are means+SEM. All mice were 3-4-month-old.

FIG. 4. Pyk2 ablation in CA1 from adult mice induces spatial learning deficits, spine loss and PSD-95-positive puncta decrease. (a). (a) Mice with floxed Pyk2 alleles ($Pyk2^{f/f}$, 4-week-old) were bilaterally injected in dorsal hippocampus CA1 with AAV expressing GFP (AAV-GFP) or GFP-Cre (AAV-Cre).AAV-GFP and AAV-Cre mice were subjected to the novel object location test as in FIG. 1b and the percentage of time exploring the displaced object (NL) compared to that exploring the unmoved object (OL). Two-way ANOVA interaction $F_{(1,44)}=9.94$, p=0.003, OL vs NL Holm-Sidak's test, AAV-GFP, t=4.0, p<0.001, AAV-Cre, t=0.45, ns (12 mice per group). The dotted line indicates the chance level. (b) Quantification of spine density in Golgi-Cox-stained apical from CA1 pyramidal neurons of AAV-GFP and AAV-Cre mice, 81-86 dendrites from 4 mice per genotype. Student's t-test $t_{165}$=10.1, $p<10^{-4}$. (c) Quantification of PSD-95-positive puncta density in CA1 stratum radiatum of AAV-GFP and AAV-Cre mice, 3 sections/mouse, 6-8 mice per genotype, Student's t-test $t_{12}$=2.36, $p<0.5$. In a, b, and c, data are means+SEM, *$p<0.05$, *$p<0.001$, and **$p<10^{-4}$.

FIG. 5. Pyk2 modulates glutamate-induced PSD-95 accumulation in dendritic spines. (a) Hippocampal neurons were cultured for 3 weeks and treated for 15 min with vehicle or glutamate (Glu, 40 μM) without or with MK801 (MK, 10 μM), added 30 min before Densitometric quantification of PhosphoTyr402-Pyk2 (pY402-Pyk2), Pyk2, and α-tubulin as a loading control. One-way ANOVA ($F_{(2,13)}$=8.02, $p=0.005$, n=4-7 per group) and post-hoc Holm-Sidak's test for multiple comparisons. (b) Cultured hippocampal neurons were treated with vehicle or glutamate (40 μM) without or with MK801 (10 μM) for 3 hours, fixed and labeled for PSD-95 immunoreactivity and rhodamine-phalloidin (an F-actin marker) to identify PSD-95-positive puncta localized in dendritic spines. The size of these PSD-95-positive puncta was measured and analyzed with one-way ANOVA ($F_{(2,30)}$=15.37, $p<0.0001$, n=10-12 per group) and Holm-Sidak's test. (c) The size of spine-associated PSD-95-positive puncta was measured in Pyk2$^{+/+}$ and Pyk2$^{-/-}$ hippocampal cultures treated for 3 hours with vehicle (Veh) or glutamate (40 μM) and immunostained for PSD-95 and quantified (n=18-27 per group). Statistical analysis with two-way ANOVA (interaction $F_{(1,89)}$=12.42, $p=0.0007$, glutamate effect, $F_{(1,89)}$=1.84, $p=0.18$, genotype effect, $F_{(1,89)}$=35.29, $p<10^{-4}$) and post-hoc multiple comparisons Holm-Sidak's test. In b and c 1-2 dendrites per neuron from 2-3 independent experiments were measured. In a, b, and c data are means+SEM, *$p<0.05$, $p<0.01$, *$p<0.001$, as compared to vehicle-treated Pyk2$^{+/+}$ cultures; °$p<0.05$, °°°$p<0.001$, and °°°°$p<10^{-4}$, as compared to glutamate-treated Pyk2$^{+/+}$ cultures. Scale bars in c and e, 5 μm.

FIG. 6. Autophosphorylation-dependent and -independent roles of Pyk2 in dendritic spines. (a) Hippocampal neurons from wild-type (WT) and Pyk2 KO mice were cultured for 21-22 days, transfected with plasmids coding GFP or GFP fused to wild-type Pyk2, to Pyk2(1-840), Pyk2(Y402F), or Pyk2-KD (as indicated), and treated with vehicle or glutamate (Glu, 40 μM, 3 h) Quantification of GFP/PSD-95 double-positive puncta size. Two-way ANOVA: interaction, $F_{(6,312)}$=19.07, $p<10^{-4}$, glutamate effect, $F_{(1,312)}$=134.3, $p<10^{-4}$, Pyk2 expression effect, $F_{(6,312)}$=20.06, $p<0^{-4}$. (c) Spine density and length were studied, in the absence of treatment, using GFP or Pyk2:GFP fluorescence. (b) Quantification of spine density. One-way ANOVA: $F_{(6,155)}$=24.90, $p<10^{-4}$. (c) Quantification of spine length. One-way ANOVA: $F_{(6,157)}$=30.68, $p<10^{-4}$ and. In a, b, and c, individual data points and means+SEM are shown, 15-20 dendrites per condition (1-2 dendrites per neuron) from 2-3 independent experiments. Post-hoc multiple comparisons were done with Holm-Sidak's test (a, b, and c), *$p<0.001$, **$p<10^{-4}$.

FIG. 7. Hippocampal alterations of Pyk2 and synaptic markers in Huntington's disease. (a, b) Hippocampal post-mortem samples from human patients grade 3-4 (HD3-4) and controls were analyzed for Pyk2 by immunoblotting and quantified by densitometry as a percentage of the mean in controls (n=6 per group, Student's t test, $t_{10}$=2.25, $p<0.05$). (b) Quantification of results for WT and R6/1 mice (percentage of WT mean, n=4-6 mice/group, Student's t test, $t_8$=3.23, $p=0.012$). (c) Quantification of phosphorylated forms and total GluN2A and GluN2B, and PSD-95 in hippocampus of WT and R6/1 mice (percentage of WT mean), Student's t test, pY1246-GluN2A, $t_9$=3.10, $p=0.013$, pY1325-GluN2A, $t_9$=2.37, $p=0.04$, GluN2A, $t_9$=5.21, $p=0.0006$, pY1472-GluN2B, $t_8$=3.64, $p=0.0066$, GluN2B, $t_8$=1.22, $p=0.26$, PSD-95, $t_9$=9.18, $p<10^{-4}$. (d, e) Quantification of PSD95 and Pyk2 in the stratum radiatum of CA1 hippocampal sections from WT and R6/1 mice in (3 slices/mouse, 5-6 mice/genotype. (d) Number of PSD95-positive puncta, Student's t test, $t_9$=3.98, $p=0.003$. (e) Number of Pyk2/PSD-95-double-positive puncta, expressed as a percentage of WT mean, Student's t test, $t_{10}$=4.66, $p=0.0009$. All data are means+SEM. *$p<0.05$, $p<0.01$, and *$p<0.001$. R6/1 mice were 5-month-old.

FIG. 8. Pyk2 protein levels restoration in the hippocampus partly rescues R6/1 mice phenotype. (a) Quantification of Pyk2 in WT mice injected with AAV-GFP (wt-GFP), or R6/A mice injected with AAV-GFP (R6/1-GFP) or AAV-Pyk2 and GFP (R6/1-Pyk2) (6-9 mice per group). One-way ANOVA: $F_{(2,18)}$=4.39, $p<0.05$, Holm-Sidak's test vs R6/1-GFP. (b) Y-maze spontaneous alternation test (10-11 mice/group). Two-way ANOVA interaction $F_{(2,56)}$=4.39, $p<0.05$, OA vs NA, Holm-Sidak's test wt-GFP t=2.64, $p<0.05$, R6/1-GFP, t=0.97, ns, R6/1-Pyk2, t=2.93, $p<0.05$. (c) Novel object location test (9-12 mice/group). Two-way ANOVA interaction $F_{(2,54)}$=11.9, $p<0.0001$, OL vs NL, Holm-Sidak's test wt-GFP t=9.08, $p<0.0001$, R6/1-GFP, t=1.60, ns, R6/1-Pyk2, t=6.66, $p<0.0001$. (d) LTP was studied as in FIG. 1c in hippocampal slices from 5-month wt-GFP, R6/1-GFP, and R6/1-Pyk2 mice (n=3-4 mice per group, 2-3 slices per mouse, 10-11 slices total). (e) Ten-min average of fEPSP slope 40 minutes after HFS, normalized to the mean of 10-min baseline (corresponding time points are indicated in e by an horizontal line). Kruskal-Wallis=15.63, $p<0.05$, post-hoc analysis with Dunn's multiple comparisons test. (f) Quantitative analysis of dendritic spine density in CA1 pyramidal neurons (59-62 dendrites from 4 mice per group). One-way ANOVA: $F_{(2,177)}$=46.7, $p<10^{-4}$, Holm-Sidak's test vs R6/1-GFP. (g) Quantification of PSD-95-positive puncta density in Hippocampal sections of WT and R6/1 mice injected with AAV-GFP or AAV-Pyk2 as indicated. One-way ANOVA $F_{(2,14)}$=10.81, $p=0.0014$, Holm-Sidak's multiple comparisons test. (h) Quantification of PSD-95/Pyk2 double-positive puncta density in Hippocampal sections of WT and R6/1 mice injected with AAV-GFP or AAV-Pyk2 as in figure g. One-way ANOVA $F_{(2,14)}$=9.76, $p=0.0022$, Holm-Sidak's multiple comparisons test. In g and h 5-7 mice per group. In all graphs values are means+SEM. *$p<0.05$, $p<0.01$, *$p<0.001$, and ****$p<10^{-4}$.

Alzheimer Study

FIG. 9. Characterization of Pyk2 in Alzheimer disease patients and 5×FAD mice. (A) Densitometry quantification of Pyk2 immunoblotting of human post-mortem prefrontal cortex samples from controls and patients with Alzheimer disease (AD). (B) Densitometry quantification of Pyk2, in WT and 5×FAD mice at 8 months of age. (C) Densitometry quantification of phosphoTyr402-Pyk2 in WT and 5×FAD mice at 8 months of age. Data were normalized to tubulin for each sample and expressed percentage of wild-type/controls.

FIG. 10. 5×FAD:Pyk2$^{-/-}$ mice generation and characterization. (A) In the open field the spontaneous locomotor activity was monitored in WT, Pyk2$^{-/-}$, 5×FAD and 5×FAD: Pyk2$^{-/-}$ mice during 30 min. (B) In the novel object recognition test (NORT) short-term memory was evaluated as the percentage of time exploring the new object (object B) versus the time exploring the old object (object A) 20 min after a training session. (C) Long-term memory was evaluated in the same test as the percentage of time exploring the new object (object C) versus the time exploring the old object (object B) 24 h after the first trial shown in B. (D) In the passive avoidance paradigm the latency (sec) to step-through was evaluated in the training trial and in the testing trial 24h after receiving an electric shock (2 sec/1 mA). (E) In the plus maze the time spent in the open arms was monitored for 5 min. In B: two-way ANOVA repeated measures and Tukey's post hoc test. In B and C: Student's t-test (intra-group comparisons). In D and E: one-way ANOVA and Tukey's post hoc test. Data are means±SEM. In A, n=6-14. In B and C, n=11-13. In D, n=11-16. In E, n=8-15. In B and C: *$p<0.001$, $p<0.01$ and *$p<0.05$ compared to % of time exploring the old object (A in left panel and B in right panel). In D and E: ***$p<0.001$, *$p<0.05$ compared to WT mice.

FIG. 11. Analysis of gross neuropathology in 5×FAD: Pyk2$^{-/-}$ mice. (A) Quantification of the Aβ-positive plaques in the three main hippocampal subfields CA1, CA3 and DG of 5×FAD and 5×FAD:Pyk2$^{-/-}$ mice. ( ). (B) Densitometry quantification of GFAP in the hippocampus of WT, Pyk2$^{-/-}$, 5×FAD and 5×FAD:Pyk2$^{-/-}$ mice. Data are means±SEM. Statistical analysis; in B: Student's t-test, in B: one-way ANOVA and Tukey's post hoc test. In A: *$p<0.05$ as compared to 5×FAD mice. In B: *$p<0.001$, $p<0.01$ and *$p<0.05$ compared to WT mice. In A n=6-8/group; in B n=5-6/genotype.

FIG. 12. Pyk2 over-expression in the hippocampus of 5×FAD mice. WT and 5×FAD mice were bilaterally injected in the hippocampus with adeno-associated virus expressing Pyk2 and GFP under the CaMKII promoter (AAV-Pyk2) or GFP alone (AAV-GFP) obtaining three groups: WT injected with AAV-GFP (WT/GFP), 5×FAD mice injected with AAV-GFP (5×FAD/GFP) and 5×FAD mice injected with AAV-Pyk2 (5×FAD/Pyk2). (A) Pyk2-positive densitometry quantification in WT/GFP, 5×FAD/GFP and 5×FAD/Pyk2 mice at 8 months of age. (B) PhosphoTyr402-Pyk2-positive densitometry quantification of in WT/GFP, 5×FAD/GFP and 5×FAD/Pyk2 mice at 8 months of age. (C) In the plus maze the time spent in the open arms was monitored for 5 min in WT/GFP, 5×FAD/GFP and 5×FAD/Pyk2 mice. (D) In the open field the spontaneous locomotor activity was monitored in all four groups during 30 min. (E) In the passive avoidance paradigm the latency (sec) to step-through was evaluated in the training trial and in the testing trial 24h after receiving an electric shock (2 sec/1 mA). (F and G) In the novel object recognition test (NORT) short-term memory (F) was evaluated as the percentage of time exploring the new object (object B) versus the time exploring the old object (object A). Long-term memory was evaluated as the percentage of time exploring the new object (object C) versus the time exploring the old object (object B) 24 h after the STM trial (G). In A-C and E: one-way ANOVA and Tukey's post hoc test. In D: two-way ANOVA repeated measures and Tukey's post hoc test. In F and G: Student's t-test (intra-group comparisons). Data are means±SEM. In A-B, n=7-9 mice/genotype. In C, n=9-13 mice/genotype. In D, n=10-13 mice/genotype. In E, n=10-12 mice/genotype. In F and G, n=9-13 mice/genotype. In G, n=10-12 mice/genotype. In A-C and E: *$p<0.05$ compared to WT-GFP, $^{\$\$}$$p<0.01$ compared to 5×FAD-GFP. In F and G: *$p<0.001$ and $p<0.01$ compared to % of time exploring the old object (A in left panel and B in right panel).

FIG. 13. Analysis of gross neuropathology in WT-GFP, 5×FAD-GFP and 5×FAD-Pyk2 mice. (A) Quantification of the Aβ-positive plaques in the three main hippocampal subfields CA1, CA3 and DG of 5×FAD/GFP and 5×FAD/Pyk2 mice. (B) Densitometry quantification of for GFAP in the hippocampus of WT/GFP, 5×FAD/GFP and 5×FAD/Pyk2 mice. Data are means±SEM. Statistical analysis; in A: Student's t-test (intra-group comparisons). In B: one-way ANOVA and Tukey's post hoc test. In A: *$p<0.05$ as compared to 5×FAD-GFP mice. In B: ***$p<0.001$ as compared to WT mice; in B, n=6-9 mice/genotype.

FIG. 14. PSD-95- and synaptophysin-positive synaptic puncta analysis in the stratum radiatum of the CA1 in WT/GFP, 5×FAD/GFP and 5×FAD/Pyk2 mice. (A) Quantification of the number of the post-synaptic PSD-95-positive puncta per field in the stratum radiatum of the hippocampal CA1 in 8-month old WT/GFP, 5×FAD/GFP and 5×FAD/Pyk2 mice. (B) Quantification of the number of the post-synaptic Synaptophysin-positive puncta per field in the stratum radiatum of the hippocampal CA1 in 8-month old WT-GFP, 5×FAD-GFP and 5×FAD-Pyk2 mice. Data are means±SEM. Statistical analysis; one-way ANOVA and Tukey's post hoc test. In A and B: **$p<0.01$ and *$p<0.05$ as compared to WT-GFP mice. N=5-8/group.

FIG. 15. Total and cleaved Src levels in Pyk2 knockout lines and in WT/GFP, 5×FAD/GFP and 5×FAD/Pyk2 mice. (A) Total Src (mature (m-Src) and cleaved Src (c-Src)) densitometry quantification in the hippocampus of Pyk2$^{+/+}$, Pyk2$^{+/-}$ and Pyk2$^{-/-}$ mice. (B) Cleaved Src densitometry quantification in the hippocampus of Pyk2$^{+/+}$, Pyk2$^{+/-}$ and Pyk2$^{-/-}$ mice. (C) Total Src (mature (m-Src) and cleaved Src (c-Src)) densitometry quantification in the hippocampus of WT/GFP, 5×FAD/GFP and 5×FAD-Pyk2 mice. (D) Cleaved Src densitometry quantification in the hippocampus of WT/GFP, 5×FAD-/GFP and 5×FAD/Pyk2 mice. Data are means±SEM. Statistical analysis, one-way ANOVA and Tukey's post hoc test. In B: *$p<0.001$ and $p<0.01$ compared to Pyk2$^{+/+}$ mice, $^{\#\#\#}$$p<0.001$ compared to Pyk2$^{+/-}$ mice. In D: *$p<0.05$ as compared to WT-GFP mice. In A-B n=7-12 mice/group. In C-D n=6-15/genotype.

Figure 16:
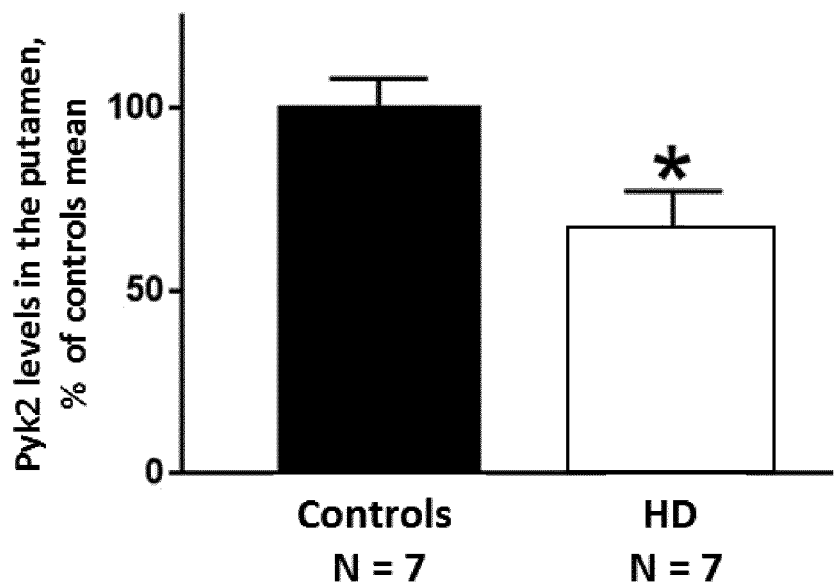

FIG. 16. Pyk2 levels in the putamen from controls and patients with Huntington's disease (HD). Samples were homogenized in a SDS solution and analyzed by immunoblotting with Pyk2 antibodies. Statistics with Student's t test. * P<0.05.

Figure 17:
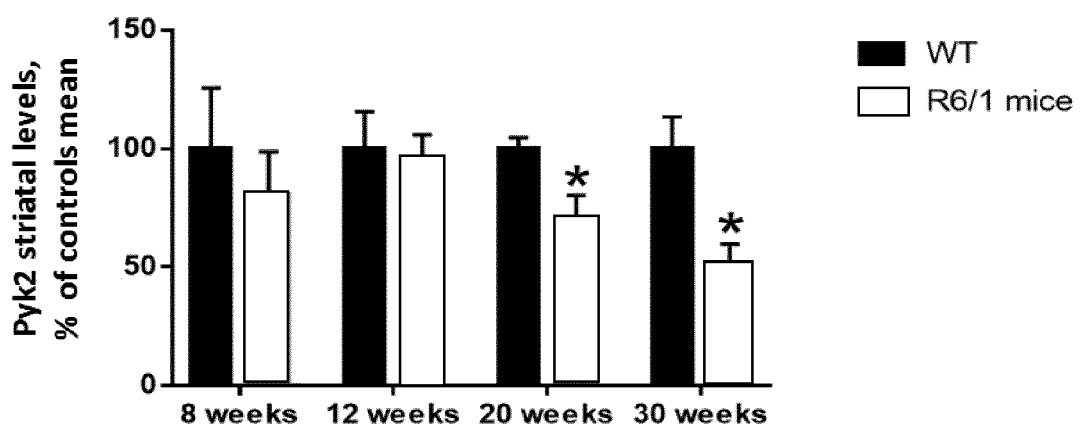

FIG. 17. Pyk2 levels in the striatum of wild type (WT) and R6/1 mutant mice at various ages, as indicated. Samples were analyzed by immunoblotting with Pyk2 antibodies. At every age the results are expressed as a percentage of the mean in WT. N=6-7 per genotype and per age. Statistics with Student's t test. * P<0.05.

Figure 18:
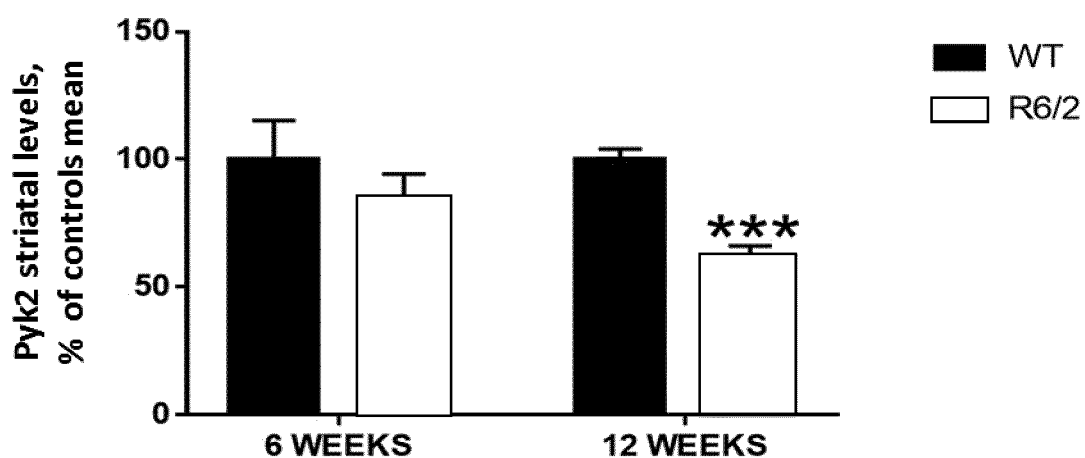

FIG. 18. Pyk2 levels in the striatum of wild type (WT) and R6/2 mutant mice at 6 and 12 weeks. Samples were analyzed by immunoblotting with Pyk2 antibodies. At every age the results are expressed as a percentage of the mean in WT. N=6-7 per genotype and per age. Statistics with Student's t test. *** P<0.001.

Figure 19:
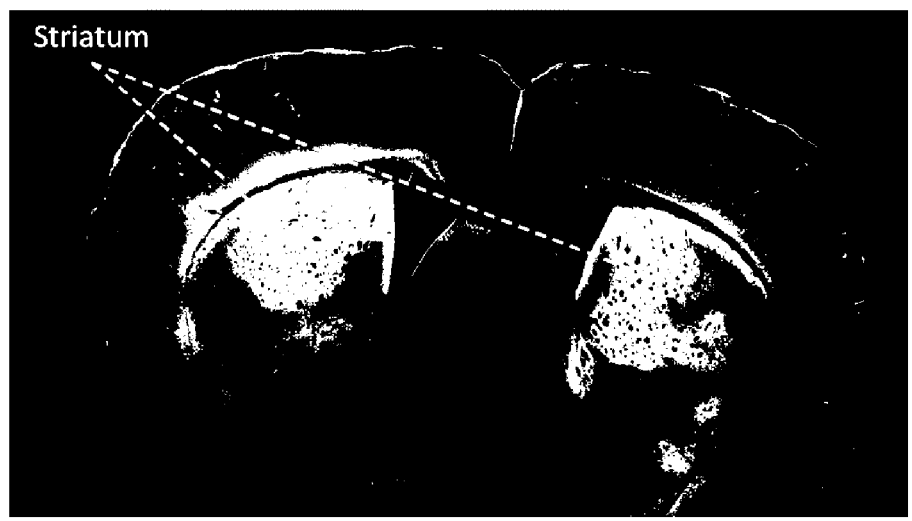

FIG. 19. A wild type mouse was stereotactically injected in the dorsal striatum with a suspension of AAV1-CamKIIa0.4-GFP-2A-mPTK2B with a T2A cleavable link (Vector Biolabs Malvern, Pa., USA). GFP expression was detected with a fluorescent microscope 1 week later.

EXAMPLE 1: HUNTINGTON'S DISEASE

Material & Methods
Animals
We used recently generated C57Bl/6 mice with floxed PTK2B exons 15b to 18 (Pyk2f/f), in collaboration with Gen-O-way (Lyon, France). These mice were used for conditional deletion of Pyk2 and were crossed with Cre line to generate a line with constitutive deletion of Pyk220. The deletion disrupts the protein kinase domain. Mouse genotyping was done from a tail biopsy as described for Pyk2−/− mice[20] and for Pyk2f/f mice, by Charles River services. The primers used for DNA amplification of Pyk2 floxed genes were: Pyk2 forward: 5'-GAGAGTGCTGGGTACTCCA-GACTCAGATAG-3' (SEQ ID No. 6), Pyk2 reverse: 5'-TTCAGGAACACCAGAGAACTAGGGTGG-3' (SEQ ID No. 7). The primers for the recombined (deleted) allele were as previously reported[1]. Breeding strategy used crossing of heterozygous mice to generate +/+, +/− and −/− progeny. Male R6/1 transgenic mice[37] (4-5-month-old) expressing exon-1 mutant huntingtin with 145 glutamines under the HD human promoter and their wild-type littermates were obtained from Jackson Laboratory (Bar Harbor, Me., USA). The animals were housed with access to food and water ad libitum in a colony room kept at 19-22° C. and 40-60% humidity, under a 12:12 h light/dark cycle. Animals were used in accordance with the ethical guidelines (Declaration of Helsinki and NIH, publication no. 85-23, revised 1985, European Community Guidelines, and French Agriculture and Forestry Ministry guidelines for handling animals, decree 87849, license A 75-05-22) and approved by the local ethical committee.

Behavioral Phenotyping

Hanging wire, plus maze and open field paradigms were carried out as described elsewhere[66]. Novel object location test (NOL) and spontaneous alternation in a Y-maze task (Y-SAT) were performed as previously described33. Briefly, for NOL an open-top arena (45×45×45 cm) was used. Mice were first habituated to the arena (2 days, 15 min per day). On the third day during the acquisition phase, mice were allowed to explore 2 duplicate objects (A1 and A2) for 10 minutes. After a delay of 24 hours, 1 object was placed in the corner diagonally opposite to its original location and mice were allowed to explore the arena for 5 minutes. The object preference was measured as the time exploring each object× 100/time exploring both objects. For Y-SAT, a Y-maze apparatus, made of clear Perspex, was used (Y-maze dimensions: arms, 35-cm length, 25-cm height, 15-cm width). In the training trial, one arm was closed (novel arm) and mice were placed in the stem arm of the Y (home arm) and allowed to explore this arm and the other available arm (familiar arm) for 10 min, after which they were returned to the home cage. After an inter-trial interval of 2 h mice were placed in the stem arm of the T-maze and allowed to freely explore all three arms for 5 min. Big and highly perceptible objects were situated surrounding the maze at 20-40 cm. The arm preference was measured as the time exploring each arm×100/time exploring both arms. Animals were tracked and recorded with Smart junior software (Panlab).

Viral Constructs and Stereotaxic Injection

For specific deletion of Pyk2 in dorsal hippocampus expression, 4-week-old Pyk2f/f mice were stereotaxically injected with adeno-associated viruses (AAV) expressing Cre recombinase and (AV-9-PV2521, AAV9.CamKII.HI.eGFP-Cre.WPRE.SV40 (AAV-Cre)) (from Perelman School of Medicine, University of Pennsylvania, USA). To over-express Pyk2 we used AAV1-CamKIIa0.4-GFP-2A-mPTK2B (AAV-Pyk2) with a T2A cleavable link (Vector Biolabs Malvern, Pa., USA). As a control we injected AAVs expressing GFP (AV-9-PV1917, AAV9.CamKII0.4.eGFP.WPRE.rBG (AAV-GFP) from Perelman). Following anesthesia with pentobarbital (30 mg kg−1), we performed bilateral injections of AAV-GFP, AAV-Cre or AAV-Pyk2 (2.6×109 GS per injection) in the dorsal hippocampus following coordinates from the bregma (millimeters); anteroposterior, −2.0; lateral, +/−1.5; and dorsoventral, +/−0.8. For R6/1 mice we performed an additional injection at dorsoventral +/− 1.2. AAVs were injected over 2 minutes, leaving the cannula in place for 5 additional minutes to ensure complete diffusion of the viruses, and then slowly retracted from the brain. The animals were monitored for 2 hours after administration and then returned to the housing facility for 21 days. After this period, animals were subjected to behavioral assessment and morphological and biochemical analysis.

Long-Term Potentiation

For fEPSP recordings, 1- to 2-month old littermate mice were anesthetized by intraperitoneal injection of ketamine/xylazine (of 75/10 mg kg$^{-1}$) and perfused with ice-cold cutting solution containing (in mM): 110 choline chloride, 25 NaHCO3, 1.25 NaH2PO4, 2.5 KCl, 0.5 CaCl2, 7 MgCl2, 25 glucose, 11.6 ascorbic acid, and 3.1 pyruvic acid. The brain was then rapidly removed and 350 μm-thick horizontal slices were prepared with a vibratome (Microm, Thermofisher). Slices were then transferred and allowed to recover for 1 hour in an interface chamber filled with ACSF (ACSF) pre-heated at 37° C. and oxygenated with 5% CO2 in O2, containing (in mM): 124 NaCl, 1 NaH2PO4, 26.2 NaHCO3, 2.5 KCl, 1.6 CaCl2, 1.2 MgCl2, 11 glucose. For recording, slices were transferred in a submerged recording chamber and superfused with ACSF supplemented with bicuculline after a cut was made between the CA3 and CA1 areas. A recording borosilicate glass pipette (2-4 MΩ) filled with ACSF was inserted in the stratum radiatum of CA1 region and a tungsten bipolar electrode (0.5 MΩ) was used to stimulate the Schaffer collaterals (HFS, 5×1 s at 100 Hz). Field excitatory post-synaptic potentials (fEPSPs) were recorded using a multiclamp 700B amplifier (Molecular Devices) low-pass filtered at 5 kHz and digitized at 20 kHz. fEPSP slopes were analyzed offline using Clampfit software (Molecular Devices). Briefly, baseline potential was set to zero and recordings were low-pass filtered at 1 kHz using Bessel filter. The initial slope of the fEPSP was then automatically measured using a 1 ms time-window manually positioned at the onset of the fEPSP. Data were acquired and analyzed blind to the experimental condition. LTP in AAV-injected R6/1 mice was done in similar conditions except that mice were 5-month old at the time of the recording.

Electron Microscopy

Mice were transcardially perfused with a solution containing 40 g/l paraformaldehyde and 1 ml l$^{-1}$ glutaraldehyde in 0.1 M sodium phosphate buffer (PB), pH 7.4. Brains were then immersed in the same fixative 12 h at 4° C. Tissue blocks containing the hippocampus were dissected and washed in 0.1 M PB, cryoprotected in 10 and 20% sucrose in 0.1 M PB, freeze-thawed in isopentane and liquid nitrogen. Samples were post-fixed in 25 ml 1-1 glutaraldehyde in 0.1 M phosphate buffer for 20 min, washed and treated with 20 g 1-1 osmium tetroxide in PB for 20 min. They were dehydrated in a series of ethanol and flat embedded in epoxy resin (EPON 812 Polysciences). After polymerization, blocks from the CA1 region were cut at 70 nm thickness using an ultramicrotome (Ultracut E Leica). Sections were cut with a diamond knife, picked up on formvar-coated 200 mesh nickel grids. For etching resin and remove osmium, sections were treated with saturated aqueous sodium periodate (NaIO4). They were then immunostained for Pyk2 with rabbit antibodies (see below) by indirect immunolabeling protein A-gold probes (20 nm) (CMC Utrecht; Netherlands) following a published method[67]. The sections were then double stained with uranyl acetate and lead citrate prior to observation with a Philips (CM-100) electron microscope. Digital images were obtained with a CCD camera (Gatan Orius). To test the immunostaining specificity, the primary antibody was omitted.

Tissue Preparation, Immunofluorescence

Animals were deeply anesthetized with pentobarbital (60 mg/kg) and intracardially perfused with a 40 g 1-1 paraformaldehyde solution in 0.1 M sodium phosphate, pH 7.2. Brains were removed and post-fixed for o.n. in the same solution, cryoprotected with 300 g 1-1 sucrose in PBS with 0.2 g 1-1 sodium azide and frozen in dry-ice cooled isopentane. Serial coronal sections (30 µm) obtained with a cryostat were processed for immunohistochemistry as free floating. The sections were washed three times in PBS, permeabilized 15 min by shaking at room temperature in PBS with 3 ml 1$^{-1}$ Triton X-100 and 30 ml 1$^{-1}$ normal goat serum (Pierce Biotechnology, Rockford, Ill., USA). After three washes, brain slices were incubated overnight by shaking at 4° C. with the corresponding primary antibodies in PBS with 0.2 g 1$^{-1}$ sodium azide: rabbit anti-Pyk2 1:500 (#07M4755) and mouse anti-MAP2 1:500 (Sigma, Chemical Co., St. Louis, Mo.), mouse anti-EM48 1:150 (#2026373, Chemicon, temecula, USA), mouse anti-PSD-95 1:500 (#QA210648, Thermo Scientific, Massachusetts, USA). After primary antibody incubation, slices were washed three times and then incubated 2 h with shaking at room temperature with specific fluorescent secondary antibodies: Cy3 goat anti-rabbit (1:200) and/or 488 goat anti-mouse (1:200) (both from Jackson ImmunoResearch, West Grove, Pa., USA). No signal was detected in control sections incubated in the absence of the primary antibody.

Primary Hippocampal Neurons Culture and Immunofluorescence

Hippocampal neurons were prepared from Ell C57Bl/6 mouse embryos (pregnant mice from Charles River, Saint Germain Nuelles, France) or from our Pyk2 mice colony as previously described[33]. The neuronal cell suspension was seeded (70,000 cells cm$^{-2}$) on coverslips precoated with poly-D-lysine (0.1 mg/ml, Sigma) in 24-well plates or in 6-well plates without coverslips. Neurobasal medium (GIBCO, Renfrewshire, Scotland, UK) containing 1 ml per 50 ml of B27 supplement (Gibco-BRL) and 50 ml of GlutaMAX (100×) (Gibco-BRL) was used to grow the cells in serum-free medium conditions and maintained at 37° C. in 5% CO2. At DIV21-22 cells were treated with vehicle or 10 µM MK801 (Sigma) for 30 min. Then, cells were treated with vehicle or 40 µM glutamate (Sigma) for 15 min and samples were collected for immunoblot analysis or the glutamate was washed out and cells further incubated for 3 h before being fixed for 10 min with 40 g 1$^{-1}$ paraformaldehyde in PB 0.2M for immunostaining. Fixed cells were permeabilized in 1 ml 1$^{-1}$ Triton X-100 for 10 min and then blocking was performed with 10 g 1$^{-1}$ BSA in PBS for 1 h. Cells were incubated with mouse monoclonal antibodies for PSD-95, (1:500, #QA210648, Millipore) or MAP2 (1:800, #073M4774, Sigma) or rabbit Pyk2 antibodies (1:500, #074M4755, Sigma, XX) at 4° C. overnight. After three washes with PBS cells were incubated with the corresponding fluorescent secondary antibodies, Cy3 or Cy2 (1:200; Jackson ImmunoReseach, West Grove, Pa.). Then, cells were rinsed twice with PBS and incubated with phalloidin-rhodamine 1:1000 (Sigma) for 45 min in PBS. After washing twice with PBS, the coverslips were mounted with Vectashield (Vector laboratories Burlingam, UK). Hippocampal neuron staining was observed with a confocal SP5-II (see below).

Cell Transfection and Constructs

Pyk2$^{+/+}$ and Pyk2$^{-/-}$ hippocampal neurons at DIV 18 were transfected using transfectin (Bio-Rad, Hercules, Calif., USA) following manufacturer's instructions and left for 48-72 h. Cells were transfected with previously described constructs38: GFP (control), GFP-Pyk2, GFP-pyk2$^{1-840}$ (Pyk2 deleted from the FAT domain and the third proline-rich motif) and GFP-pyk2$^{Y402F}$ (Pyk2 with a point mutation of the autophosphorylated tyrosine-402). GFP was fused to the N-terminus of Pyk2

Confocal Imaging and Analysis

Hippocampal neurons in vitro or dorsal hippocampus in fixed tissue were imaged using a Leica Confocal SP5-II with a 63× numerical aperture lens with 5× digital zoom and standard (1 Airy disc) pinhole. Frame averaging (4 frames per z-step) was held constant throughout the study. Confocal z-stacks were taken every 0.2 µm for in vitro experiments and every 2 µm for in vivo experiments, and at 1,024×1,024 pixel resolution. The number and size of labeled PSD95-positive clusters in vivo and in vitro were analyzed with the freeware NIH ImageJ (Wayne Rasband, NIH) as previously described with minor changes68. Briefly, for in vivo imaging analysis, for each mouse, at least 3 slices of 30 µm containing dorsal hippocampal tissue were analyzed. Up to 3 representative images, from CA1stratum radiatum layer, were obtained from each slice. For in vitro imaging, PSD95-positive clusters colocalizing with enriched F-actin (stained with Phalloidin-rodhamine) or GFP-enriched spines in dendrites from hippocampal neurons were quantified as previously described[69] with minor changes using the ImageJ software. At least 20 neurites (1-2 neurites per neuron) per condition were obtained and analyzed from 2-3 different cultures.

Golgi Staining, Spine Counting, and Morphology Analysis

Fresh brain hemispheres were processed following the Golgi-Cox method as described elsewhere[70]. Bright-field images of Golgi-impregnated stratum radiatum dendrites from hippocampal CA1 pyramidal neurons were captured with a Nikon DXM 1200F digital camera attached to a Nikon Eclipse E600 light microscope (×100 oil objective). Only fully impregnated pyramidal neurons with their soma found entirely within the thickness of the section were used. Image z stacks were taken every 0.2 µm and at 1,024×1,024 pixel resolution, yielding an image with pixel dimensions of 49.25×49.25 µm. Z-stacks were deconvolved using the Huygens software (Scientific volume imaging, Hilversum, Netherlands), to improve voxel resolution and reduce optical aberration along the z-axis. Segments of proximal apical dendrites were selected for the analysis of spine density and spine morphology according to the following criteria: (a) segments with no overlap with other branches that would obscure visualization of spines and (b) segments either "parallel" to or "at acute angles" relative to the coronal surface of the section to avoid ambiguous identification of spines. Only spines arising from the lateral surfaces of the dendrites were included in the study; spines located on the top or bottom of the dendrite surface were ignored. Given that spine density increases as a function of the distance from the soma, reaching a plateau 45 µm away from the soma, we selected dendritic segments of basal dendrites 45 µm away from the cell body. The total number of spines was obtained using the cell counter tool in the ImageJ software. At least 60 dendrites per group from at least three mice per genotype were counted. For a more precise description of the dendritic shape changes, the spine head diameter was analyzed as a continuous distribution (between 368 and 418 spines per group were analyzed) using the ImageJ software. Then, a distribution analysis of head diameter was performed. Then, head diameter analysis was performed manually using ImageJ for all the spines in control mice. Spine neck was measured in all spines as the distance from the dendritic shaft to the head of the spine using the ImageJ.

Subcellular Fractionation

To obtain striatal cytosolic and nuclear fractions of R6/1 mice at 20 weeks, the hippocampus was homogenized in lysis buffer (4 mM HEPES, 0.32 M sucrose, 1 mM phenylmethylsulfonyl fluoride (PMSF), 10 mg 1-1 aprotinin, 1 mg 1-1 leupeptin, 2 mM sodium orthovanadate, 0.1 g 1-1 benzamidine) with a Teflon-glass potter and centrifuged at 3000 g for 10 min to obtain the cytosolic (supernatant) and the nuclear (pellet) fractions. The nuclear fraction was resuspended with lysis buffer (10 mM Tris-HCl (pH 7.5), 0.25 M sucrose, 2 mM PMSF, 10 mg $1^{-1}$ aprotinin, 1 mg $1^{-1}$ leupeptin, 2 mM Na3VO4) and sonicated.

Postmortem Brain Tissues

Hippocampal brain tissues were supplied by the Banc de Teixits Neurològics (Biobanc-HC-IDIBAPS), Barcelona, Spain. They included 6 controls (mean±SEM; age 53.5±6.8 years; postmortem intervals, 4-18 hours), 4 patients with HD grades 1-2 (age 72.2±1.7 years; postmortem intervals, 6-14 hours), and 7 patients with HD grades 3-4 (age 54.5±6.5 years; post-mortem intervals of 4-17 hours).

Immunoblot Analysis

Animals were euthanatized by cervical dislocation. The hippocampus was dissected out, frozen using CO2 pellets and stored at −80° C. until use. Briefly, the tissue was lysed by sonication in 250 μl of lysis buffer (PBS, 10 ml $1^{-1}$ Nonidet P-40, 1 mM phenylmethylsulphonyl fluoride, 10 mg $1^{-1}$ aprotinin, 1 mg $1^{-1}$ leupeptin, 2 mg $1^{-1}$ sodium orthovanadate). After lysis, samples were centrifuged at 12,000 rpm for 20 min. Supernatant proteins (15 μg) from total brain regions extracts were loaded in SDS-PAGE and transferred to nitrocellulose membranes (GE Healthcare, LC, UK). Membranes were blocked in TBS-T (150 mM NaCl, 20 mM Tris-HCl, pH 7.5, 0.5 ml $1^{-1}$ Tween 20) with 50 g $1^{-1}$ phospho-Blocker (Cell Biolabs, San Diego, Calif.) or 50 g $1^{-1}$ non fat dry milk and 5 g $1^{-1}$ BSA. Immunoblots were probed with the following antibodies (all diluted 1:1000): rabbit polyclonal antibodies: Pyk2 (#074M4755, Sigma), Pyk2 (#ab32571, Abcam, epitope within the first 100 residues), phosphoY402-Pyk2 (#5), PSD-95 (#QA210648), phosphoY876-GluA2 (#2), and phosphoY1246-GluN2A (#1, Cell Signaling Technology, Danvers, Mass., USA), GluA1 (#JBC1830522, Upstate Biotechnology, NY, USA), phosphoY1472-GluN2B (#04242010009761, Cayman antibodies, Ann Arbor, Mich., USA), phosphoY418-Src reacting with all phosphoSFKs (#GR144140-2), and phosphoY1325-GluN2A (#GR14161032, Abcam, Cambridge, UK), phosphoS831-GluA1 (#2726818), GluN2B (#2697434), GluA2 (#2280905), and GluN2A (#NRG1815904, Millipore Bedford, Mass., USA), mouse monoclonal antibodies: phosphoERK1/2 (#26, Cell Signaling Technology, Danvers, Mass., USA), FAK (#JBC1900835, Santa Cruz Biotechnology, Santa Cruz, Calif., USA), GluN1 (#225310, Millipore, Bedford, Mass., USA). All blots were incubated with the primary antibody overnight at 4° C. by shaking in PBS with 0.2 g $1^{-1}$ sodium azide. After several washes in TBS-T, blots were incubated with secondary anti-rabbit or anti-mouse IgG IRdye800CW-coupled or anti-mouse IgG IRdye700DXcoupled antibodies (1:2000, Rockland Immunochemicals, USA). Secondary antibody binding was detected by Odyssey infrared imaging apparatus (Li-Cor Inc., Lincoln, Nebr.). For loading control a mouse monoclonal antibody for α-tubulin was used (#083M4847V, 1:10000, Sigma) was used.

Statistical Analysis

Statistical analyses were carried out using the GraphPad Prism 6.0 software. Data sets were tested for normality distribution with d'Agostino-Pearson and Shapiro-Wilk tests. When distribution was not different from normal they were analyzed with parametric using Student's t-test (95% confidence), one-way ANOVA or two-way ANOVA, with Holm-Sidak post hoc multiple comparisons test. Two by two comparisons were two-tailed. In cases in which the distribution was significantly different from normal (p<0.05), non-parametric tests were used including Mann and Whitney for two groups comparisons and Kruskal Wallis for more than two groups and Dunn's test for post-hoc multiple comparisons. Kolmogorov-Smirnov test was used as indicated in the figure legends. Values of p<0.05 were considered as statistically significant.

Results

Pyk2 Knockout Impairs Hippocampal-Dependent Memory and LTP

Figure 1B:
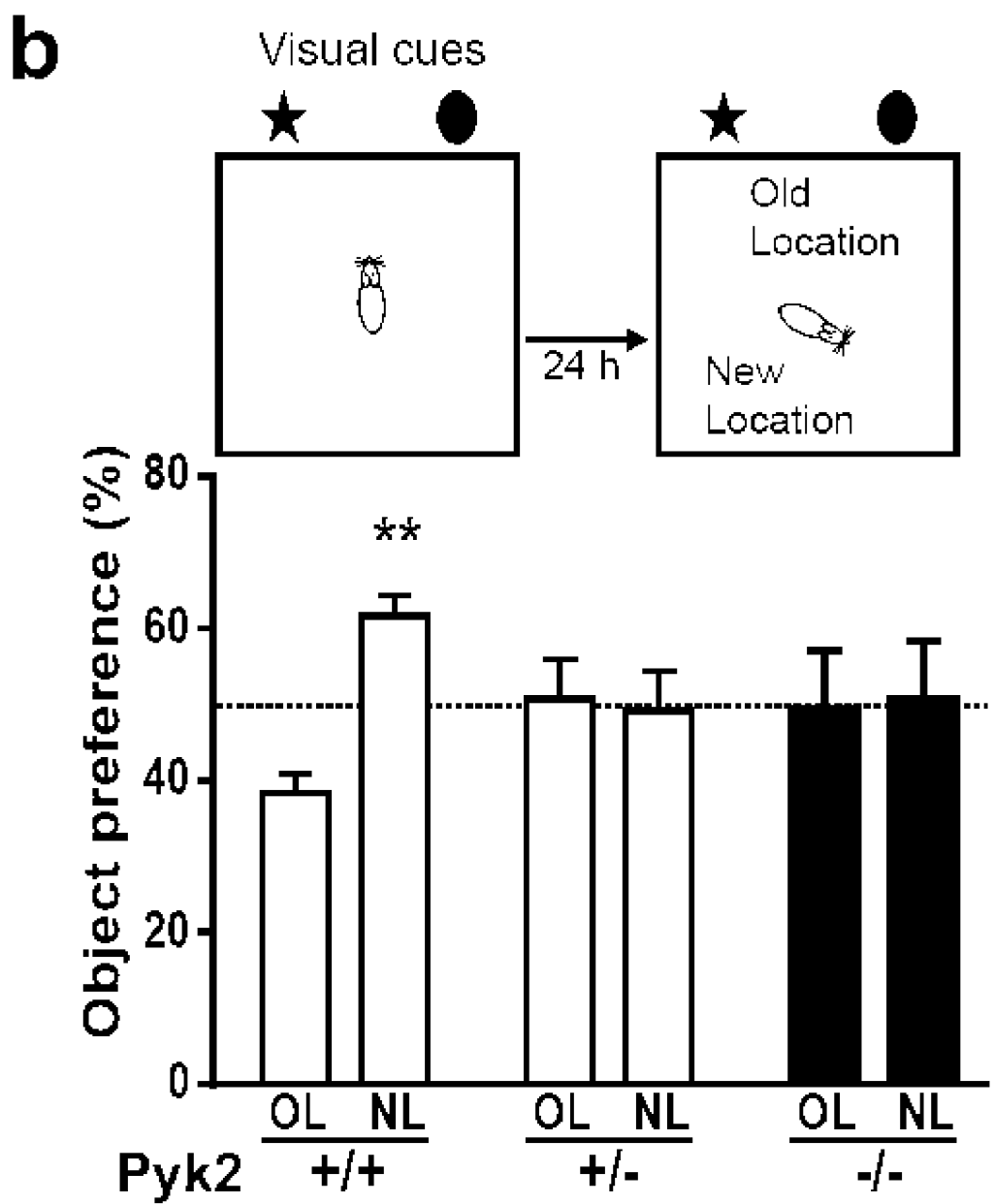

To study the role of Pyk2 in the brain we used a knockout mouse line[20] that we recently generated. As previously observed for a similar line[18], these mice bred normally and there were no differences between Pyk2$^{+/+}$, Pyk2$^{+/-}$, and Pyk2$^{-/-}$ mice in body weight, muscular strength, general locomotor activity, or anxiety levels evaluated in the elevated plus-maze. We tested Pyk2$^{+/+}$, Pyk2$^{+/-}$, and Pyk2$^{-/-}$ littermate mice in two simple tasks that depend on hippocampus-mediated spatial memory[21,22]. In the Y-maze spontaneous alternation task, Pyk2$^{+/+}$ mice showed a significant preference for the new arm 2 hours after exposure to the other arm, whereas both Pyk2$^{+/-}$ and Pyk2$^{-/-}$ littermates explored equally both arms (FIG. 1a). In the novel object location test, 24 h after a first exposure, wild-type mice spent more time exploring the object placed at a new location (FIG. 1b). In contrast, both Pyk2$^{+/-}$ and Pyk2$^{-/-}$ mice did not display any preference for either object (FIG. 1b). These results revealed spatial memory deficits in both heterozygous and homozygous mutant mice.

We next examined whether these behavioral deficits were accompanied by altered synaptic plasticity in hippocampal slices. We restricted our study to CA1, a hippocampal region extensively implicated in spatial learning. High-frequency conditioning tetanus of Schaffer collaterals (5×1 s at 100 Hz) induced LTP in CA1 of wild-type mice (FIG. 1c). In contrast, no LTP was observed in slices from Pyk2$^{+/-}$ or Pyk2$^{-/-}$ mice (FIG. 1c, d). We also examined a form of short-term plasticity at the same synapses. Paired-pulse facilitation was observed in wild-type mice but was markedly decreased in both homozygous and heterozygous Pyk2 mutant mice (FIG. 1e), suggesting the existence of a presynaptic role of Pyk2. Altogether these results show that deletion of Pyk2 has dramatic consequences on hippocampus-dependent memory and synaptic plasticity in CAL Importantly, the heterozygous mutation of Pyk2 was as severe as the full deletion, indicating that Pyk2 levels may be limiting for hippocampal plasticity.

Alteration in NMDA Receptors and PSD-95 in Pyk2 Mutant Mice

Figure 2C:
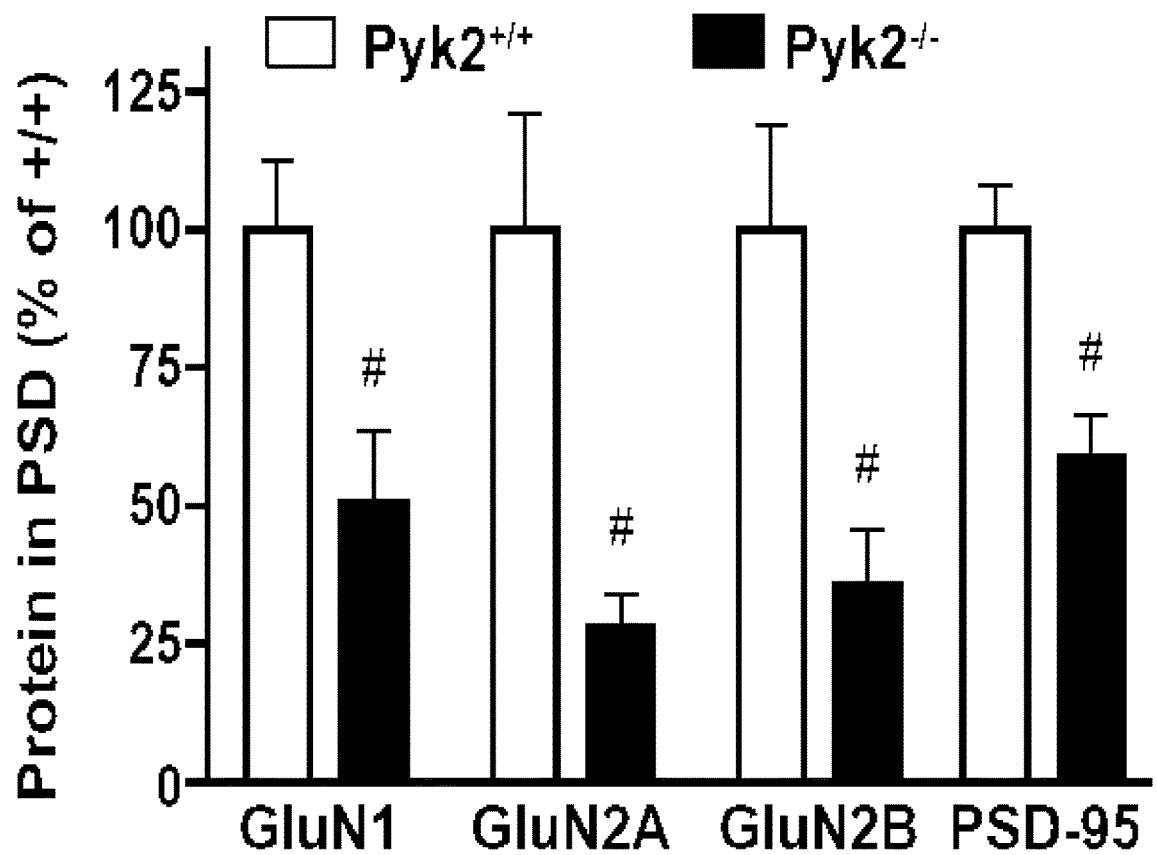

To explore the molecular consequences of Pyk2 deficit we examined by immunoblotting proteins previously associated with the Pyk2 pathway at synapses. In hippocampal tissue of Pyk2$^{+/-}$ mice, Pyk2 protein was decreased by about 50% as compared to wild-type littermates, and was not detectable in Pyk2$^{-/-}$ mice (FIG. 2a). No N-terminal truncated fragment was detected in the knockout mice, showing that deletion of exons 15-18 in the Pyk2 gene[20] destabilized the resulting mRNA and/or protein. There was no compensatory alteration of the related focal adhesion kinase (FAK, FIG. 2a). In both Pyk2$^{+/-}$ and Pyk2$^{-/-}$ mice, the activated form of SFKs (pY-SFK, pTyr420 in Fyn), was markedly reduced, whereas Fyn levels were unchanged (FIG. 2a), underlining the contribution of Pyk2 in regulating SFKs phosphorylation. In contrast, there was no change in the basal phosphorylation (activation) of ERK1/2, reported to be downstream of Pyk2 in some cell systems[10], including in hippocampal neurons in culture[6], but not in adult slices[23]. We then focused on glutamate receptors. We found no consistent change between genotypes in GluA1 and GluA2 AMPA receptors subunits, or in their phosphorylated forms pSer831-GluA1 and pTyr876-GluA2. NMDA receptors GluN1 levels were not changed either (FIG. 2b). In contrast, we observed marked alterations of NMDA receptor N2 subunits. The phosphorylated forms of GluN2A and GluN2B, pTyr1246- and pTyr1325-GluN2A, and pTyr1472-GluN2B, were decreased in both Pyk2$^{-/-}$ compared to wild-type mice. Total GluN2B was not changed indicating deficient tyrosine phosphorylation in the absence of Pyk2 (FIG. 2b). In contrast, total GluN2A was decreased (FIG. 2b). We also examined PSD-95, a post-synaptic scaffolding protein that interacts with both NMDA receptors and Pyk2[5,14]. The levels of PSD-95 were markedly decreased in homozygous mutant mice (FIG. 2b). Thus, in contrast with the behavioral and physiological deficits, which appeared as pronounced in heterozygous as in homozygous mutant mice (see FIG. 1), the protein alterations in Pyk2$^{+/-}$ mice were intermediate between wild-type and Pyk2$^{-/-}$, indicating some proportionality between the decrease in Pyk2 and its consequences on other proteins. To determine the changes in receptors that took place at synapses we carried out subcellular fractionation and isolated postsynaptic densities (PSDs). The amounts of GluN1, GluN2A, GluN2B, and PSD-95 were decreased in the PSD fraction of Pyk2$^{-/-}$ mice as compared to wild-type (FIG. 2c). These results showed that the lack of Pyk2 signaling resulted in decreased tyrosine phosphorylation of SFKs and GluN2B subunits as well as decreased levels of GluN2A and PSD95 total protein. The enrichment of all these proteins in PSDs was markedly decreased, indicating a key role of Pyk2 in regulating the recruitment of post-synaptic proteins to PSDs.

Spines are Altered in the Hippocampus of Pyk2 Mutant Mice

To explore how Pyk2 deficit could induce alterations of synaptic proteins we first determined its localization in CA1. Pyk2 immunofluorescence in the neuropil was punctuate and appeared to surround MAP2-positive dendritic processes. Some Pyk2-positive puncta colocalized with PSD-95-positive puncta, identifying them as postsynaptic densities. We then examined Pyk2 immunoreactivity by electron microscopy. Pyk2-positive immunogold particles were found in both pre-synaptic elements and dendritic spines. Pyk2 was enriched in asymmetric (presumably excitatory) synapses as compared to symmetric (presumably inhibitory) synapses. Because of Pyk2 colocalization with PSD-95 and of the marked decrease of PSD-95 in Pyk2$^{-/-}$ mice, we quantified PSD-95-positive puncta in CA1 stratum radiatum of wild-type and mutant mice. The number of PSD-95-positive puncta was significantly reduced in Pyk2$^{+/-}$ and even more so in Pyk2$^{-/-}$ as compared to Pyk2$^{+/+}$ mice (FIG. 3a). This effect appeared consistent throughout CA1 depth.

To determine the consequences of these alterations on spines, we analyzed spine density and morphology in CA1 pyramidal neurons, using the Golgi-Cox method. The apical dendritic spines density was decreased in Pyk2$^{+/-}$ (−8%) and Pyk2$^{-/-}$ (−16%) mice as compared to wild-type (FIG. 3b). The decrease in spine number was less pronounced that the decrease in PSD-95 puncta, possibly due to an immunofluorescence detection threshold and/or an increased number of spines lacking PSD-95. To determine whether the absence of Pyk2 also affected spine morphology, we quantified the spine head diameter and spine neck length. Spine head size did not change between genotypes (FIG. 3c), whereas spine neck length was decreased in Pyk2 mutant mice (FIG. 3d). Altogether, these data show that the lack of Pyk2 leads to a decrease of PSD-95 at synapses and a decreased number of PSDs and spines.

Adult Hippocampal Pyk2 Deletion Recapitulates the Phenotype

Figure 4C:
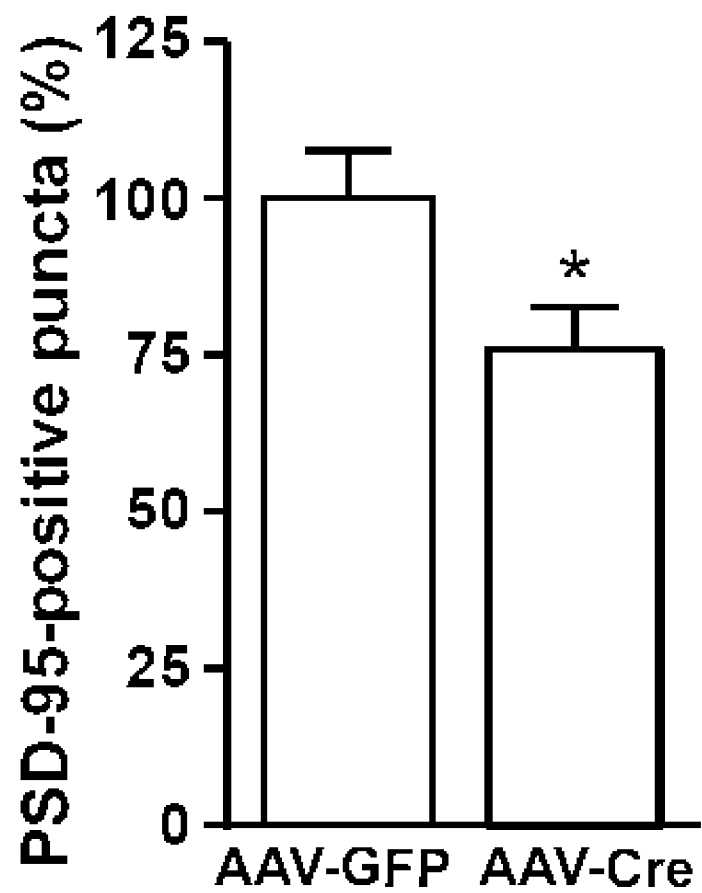

Although Pyk2 expression in the hippocampus is mostly post-natal[4], the severe alterations observed in Pyk2$^{+/-}$ and Pyk2$^{-/-}$ mice could result from developmental effects. In order to rule out this possibility we used 3-month old mice bearing floxed Pyk2 alleles (Pyk2$^{f/f}$ mice). Mice received a bilateral stereotaxic injection in CA1 of adeno-associated virus expressing Cre recombinase and GFP (AAV-Cre) or expressing GFP alone (AAV-GFP), as a control. Three weeks after AAV-Cre injection Pyk2 expression disappeared in CA1 whereas the injection of AAV-GFP had no effect. In the novel object location test, AAV-GFP-injected mice showed increased preference for the object placed in the new location, whereas AAV-Cre-injected mice did not (FIG. 4a). We analyzed spine density in CA1 apical dendrites and found it was significantly reduced in AAV-Cre-injected mice as compared to AAV-GFP-injected mice (FIG. 4b). We also quantified a reduced number of PSD-95-positive puncta in CA1 stratum radiatum of AAV-Cre-injected mice as compared to AAV-GFP-injected mice (FIG. 4c). Altogether these results show that local deletion of Pyk2 in CA1 of adult mice recapitulates behavioral and morphological deficits observed in Pyk2$^{+/-}$ and Pyk2$^{-/-}$ mice, ruling out a developmental effect in the phenotype of Pyk2 mutant mice.

Pyk2 Deficit Alters NMDA-Induced PSD-95 Recruitment in Spines

Figure 5C:
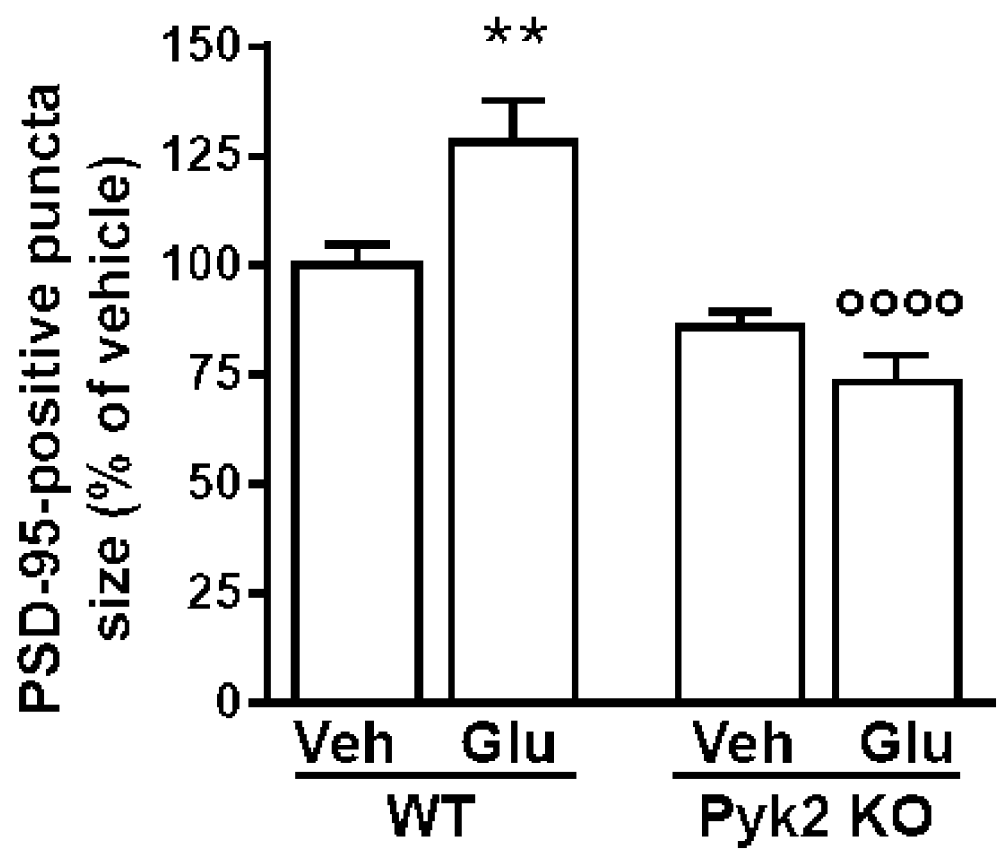

PSD-95 undergoes rapid activity-dependent relocalization[24]. Although neuronal stimulation decreases PSD-95 palmitoylation-dependent synaptic targeting[25] and increases its ubiquitination and degradation[26], prolonged neuronal activity was shown to increase PSD-95 synaptic concentration[27]. PSD-95 is phosphorylated on multiple tyrosine residues and this phosphorylation can increase its synaptic clustering[28,29]. Since PSD-95 synaptic clustering was decreased in the absence of Pyk2, we hypothesized Pyk2 may influence the synaptic localization of PSD-95. We tested this hypothesis using hippocampal neurons in primary culture at ~21-22 DIV. As expected, glutamate treatment (40 µM, 15 min) increased Pyk2 phosphorylation at Tyr402 in hippocampal neurons in culture and this effect was prevented by an NMDA receptor antagonist, MK801 (10 µM, FIG. 5a). The size of PSD-95-positive puncta measured 3 h after glutamate treatment was increased and this effect was also prevented by MK801 (FIG. 5b). We then compared the effects of glutamate on the size of PSD-95 puncta in neurons from wild-type and Pyk2-KO mice (FIG. 5c). In the absence of Pyk2, the effects of glutamate on the size of PSD-95 puncta were lost (FIG. 5c). Altogether these results reveal a role for Pyk2 in NMDA receptor-induced PSD-95 recruitment at post-synaptic sites.

Pyk2 Function in Spines is Partly Phosphorylation-Dependent

Figure 6A:
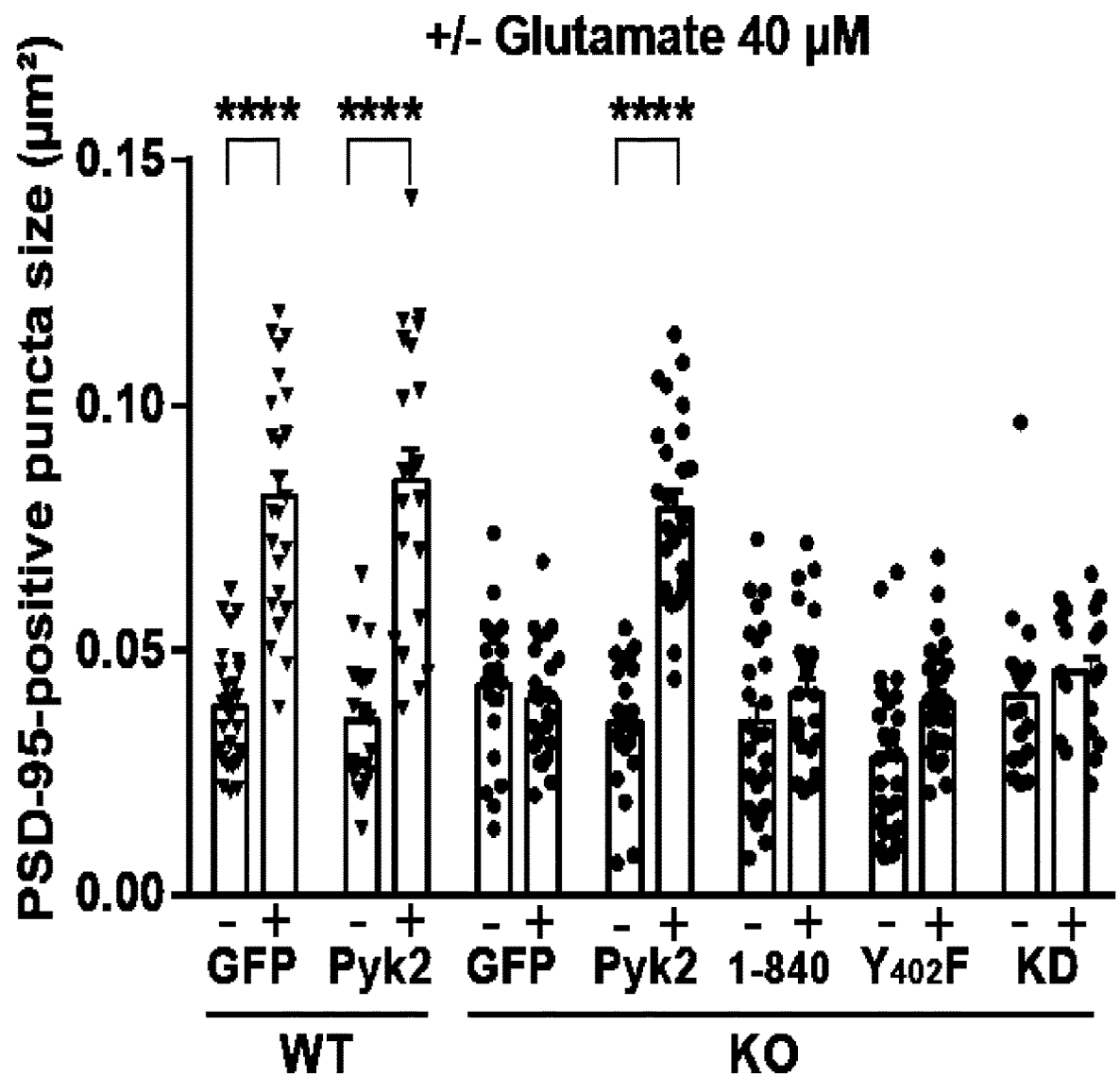

Since Pyk2 is a large protein with tyrosine kinase activity, functionally important autophosphorylation, and interactions with multiple partners[9], we examined which of its molecular properties were required for PSD-95 and spines regulation. We transfected wild-type and Pyk2-KO hippocampal cultures with GFP or GFP fused to either Pyk2, or Pyk2$_{1-840}$, unable to bind to PSD-95[5], or Pyk2$_{Y402F}$ with a point mutation of the autophosphorylation site or to kinase-dead Pyk2 (Pyk2-KD) with a K457A mutation[30]. We first analyzed the size of PSD-95-positive puncta in these various conditions. As in untransfected neurons (see FIG. 5b-c), glutamate treatment increased the size of PSD-95-positive puncta in wild-type cultures transfected with either GFP or GFP:Pyk2, used as controls (FIG. 6a). Glutamate effects were absent in KO cultures transfected with GFP, but were rescued by Pyk2:GFP transfection (FIG. 6a). In contrast, glutamate treatment did not increase PSD-95-positive puncta size in Pyk2$^{-/-}$ cultures transfected with GFP:Pyk2$_{1-840}$, GFP:Pyk2Y$_{402F}$, or GFP:Pyk2-KD (FIG. 6a). These results show that the autophosphorylation site, Tyr-402, the kinase activity, and the C-terminal domain of Pyk2 are all essential for glutamate-induced PSD-95 synaptic translocation.

We then examined the rescue of spine density in cultured hippocampal neurons. Dendritic spine density was reduced in Pyk2-KO neurons as compared to wild-type (FIG. 6b), as observed in vivo (FIG. 3b). Transfection of GFP:Pyk2 rescued spine density in KO neurons (FIG. 6b). Transfection of GFP:Pyk2$_{1-840}$ had no significant effect, but, in contrast to what we observed for PSD-95 puncta rescue (see FIG. 6a), both GFP:Pyk2$_{Y402F}$ and GFP:Pyk2-KD fully restored spine density (FIG. 6b), revealing a role for Pyk2 independent of its autophosphorylation and kinase activity. We also quantified the effects of Pyk2 deletion on spine length (FIG. 6c). In the absence of Pyk2, spines were shorter, as observed in vivo (see FIG. 3d), but this effect was not rescued by re-expression of wild type or mutated Pyk2 (FIG. 6c). This lack of rescue may indicate a contribution of presynaptic Pyk2 in spine length regulation since with the low transfection rate in our culture system, concomitant transfection of pre- and post-synaptic neurons was very rare. Altogether these results show that Pyk2 is important for PSD-95 synaptic enrichment and that this function requires both the C-terminal region involved in PSD-95 interaction and the autophosphorylation site and tyrosine kinase activity. In contrast Tyr402 or kinase activity are not necessary for Pyk2 effects on spine density, revealing the existence of autophosphorylation/kinase activity-dependent and -independent roles of Pyk2 in spines.

Hippocampal Pyk2 is Altered in Huntington's Disease

Since our results emphasized the high sensitivity of hippocampal function to Pyk2 protein expression levels, we hypothesized that any alteration in Pyk2 levels in pathological conditions might have deleterious consequences. HD appeared as an interesting condition since Pyk2 and wild-type Htt interact with the same SH3 domain of PSD-95[14,31]. This interaction is altered in mutant Htt with a pathological polyglutamine expansion[31], resulting in PSD-95 mislocalization to extrasynaptic sites[32]. We noticed that the hippocampal phenotype of Pyk2 KO mice resembled that of Huntington's disease (HD) mouse models, which display spatial learning impairments[33], decreased PSD-95[34], dendritic spines loss[35], and shorter dendritic spine necks[33]. To test the possible involvement of Pyk2 in HD we first measured Pyk2 protein levels in post-mortem hippocampal samples from human patients. In patients with intermediate or late HD (grade 3-4[36]) Pyk2 levels were reduced to 64±8% of controls (mean±SEM, FIG. 7a), whereas in patients at prodromal or early stage (grade 1-2) there was no significant change. Pyk2 was also diminished in the hippocampus of R6/1 mice, an HD mouse model, transgenic for the first exon of the human Htt gene with amplified CAG repeats[37] (64±6% of control levels, mean±SEM, FIG. 7b). Since Pyk2 can traffic between cytoplasm and nucleus[38], and since R6/1 mutated Htt accumulates in the nucleus[39] we looked for the existence of altered cytonuclear distribution of Pyk2 or its possible sequestration in nuclear aggregates. Although Pyk2 was predominantly decreased in the cytoplasm it was not sequestered in intra-nuclear aggregates and did not colocalize with EM48-immunolabeled nuclear aggregates. These results indicated a reduced Pyk2 function in the cytoplasm of HD mice. Indeed, in R6/1 mice we observed changes similar to those in Pyk2 mutant mice, including a decrease in total GluN2A but no change in GluN2B, a decrease in tyrosine phosphorylated GluN2A and GluN2B, and a marked decrease in total PSD-95 (FIG. 7c). Double immunostaining for Pyk2 and PSD-95 in CA1 of wild-type and R6/1 mice showed a decreased number of PSD-95-positive puncta in R6/1 mice as compared to wild-type mice (FIG. 7d), and less colocalization of PSD-95-positive and Pyk2-positive puncta in mutant mice (FIG. 7e). The similarity in the modifications observed in R6/1 mice and Pyk2 mutant mice suggested that the decreased levels of Pyk2 might contribute to PSD-95 and NMDA receptors subunits alterations.

Pyk2 Partly Rescues the Hippocampal Phenotype of R6/1 Mice

Since the levels of Pyk2 in the hippocampus of HD patients and R6/1 mice (FIG. 7b) were close to those in Pyk2+/− mice which displayed a similar phenotype, we asked whether correcting this defect in R6/1 mice could rescue some of their deficits. We stereotaxically injected AAV expressing either Pyk2 and GFP or GFP alone in the dorsal hippocampus of R6/1 mice (R6/1-Pyk2 and R6/1-GFP mice, respectively) or GFP alone in wild-type mice (WT-GFP) as a control. Three weeks after the injection, GFP expression demonstrated a wide spreading of viral transduction within the dorsal hippocampus, but restricted to this brain structure. Immunoblotting showed that Pyk2 levels in R6/1-GFP mice, which were 50±3% of those in WT-GFP mice, were raised to 80±4% in R6/1-Pyk2 mice (FIG. 8a). The recovery of Pyk2 expression restored R6/1 mice performance in the Y-maze spontaneous alternation task (FIG. 8b) and corrected the deficit in the novel object recognition task (FIG. 8c). We also examined LTP in these mice at the same age as for behavioral experiments (4-5 months). In WT-GFP mice, we observed a robust LTP in CA1 after stimulation of Schaffer collaterals (FIG. 8d, e). In contrast, in R6/1-GFP and R6/1-Pyk2 mice synaptic potentiation was not stable (FIG. 8d, e). One hour after HFS, potentiation was observed only in WT-GFP mice (FIG. 8e), revealing that restoration of Pyk2 levels was not sufficient to correct the LTP impairment.

To assess the cellular effects of Pyk2 recovery possibly underlying the behavioral improvements, we analyzed spine density in CA1 apical dendrites by Golgi-Cox. Spine density, which was decreased in R6/1-GFP compared to WT-GFP mice, was partly restored by Pyk2 viral expression in R6/1-Pyk2 mice (FIG. 8f). We also analyzed PSD-95- and Pyk2-positive puncta in CA1 stratum radiatum of the 3 groups of mice. R6/1-GFP mice displayed a reduced number of PSD-95-positive puncta (FIG. 8g) and fewer double-positive PSD-95/Pyk2 puncta (FIG. 8h) compared to WT-GFP mice, in agreement with the results in FIG. 7d, c The numbers of PSD-95-positive puncta (FIG. 8g) and PSD-95/Pyk2 double-positive puncta (FIG. 8h) were both completely rescued in R6/1-Pyk2, reaching values similar to those in WT-GFP mice. These results strongly indicate that Pyk2 deficit contributes to the hippocampal phenotype of the R6/1 HD mouse model, including cognitive deficits, dendritic spine loss, and PSD-95 alteration. Moreover, they show that these deficits can be largely improved by Pyk2 induced expression, although this expression was not sufficient to restore synaptic plasticity in our experimental conditions.

Conclusion

Here we show the functional importance of the $Ca^{2+}$-activated non-receptor tyrosine kinase Pyk2 for hippocampal function and spines physiology. We also provide evidence that Pyk2 deficit plays a significant role in HD, a severe genetic neurodegenerative disorder. Although $Pyk2^{+/-}$ and $Pyk2^{-/-}$ mice develop and breed normally in standard animal facility conditions, and show no gross behavioral defects, they appear strongly deficient in hippocampal-related memory tasks. These behavioral impairments were accompanied by impaired synaptic plasticity, decreased levels and/or tyrosine phosphorylation of NMDA receptor subunits, and alterations in PSDs composition and in spines density and morphology.

A previous study in hippocampal slices using overexpression or interfering constructs, reported that Pyk2 can regulate NMDA receptor function and LTP induction. Here we show that in Pyk2 mutant mice LTP was not induced in standard conditions at Schaffer collaterals synapses on CA1 pyramidal neurons. A number of biochemical alterations at the post-synaptic level are likely to participate in this deficit. Both GluN2A and GluN2B were altered with a decreased total and tyrosine phosphorylated GluN2A and a decreased tyrosine phosphorylation of GluN2B. Moreover, subcellular fractionation revealed a decrease of the three NMDA receptor subunits (GluN1, GluN2A, and GluN2B) in the PSD fraction. The reduction of GluN2B in PSDs may result from its decreased tyrosine phosphorylation, which is known to promote surface expression of GluN2B-containing NMDA receptors[40] and their recruitment to PSDs[41]. This phosphorylation deficit was in agreement with the decreased active form of SFKs we observed in Pyk2 mutant mice, supporting their role in mediating NMDA receptors phosphorylation downstream from Pyk2[7]. In the case of GluN2A the total protein and the phosphorylated form were decreased. Since tyrosine phosphorylation of GluN2A increases NMDA receptor currents[42,43], reduction of both forms of GluN2A may contribute to synaptic defects of Pyk2 knockout mice. These alterations seemed to be specific for the NMDA receptor complex since AMPA receptors levels and phosphorylation were not affected. These combined alterations in NMDA receptor subunits provide a first basis for the functional deficit in LTP induction. Many other aspects of synaptic function and plasticity remain to be investigated in Pyk2 mutant mice, and the modifications induced by the absence of Pyk2 clearly extend beyond NMDA receptors.

A marked alteration observed in Pyk2 mutant mice concerned PSD-95. PSD-95 SH3 domain is known to bind Pyk2 C-terminal Pro-rich motif[14], thereby clustering and activating Pyk2 in response to $Ca^{2+}$ increase[5,14]. In contrast, effects of Pyk2 on PSD-95 have not been described. Our study reveals that Pyk2 has a critical influence on PSD-95, regulating its levels, its localization at PSDs in basal conditions, and its clustering in response to stimulation of NMDA receptors. The decreased PSD-95 expression cannot explain, by itself, the absence of LTP in Pyk2 mutant mice, since PSD-95 knockout mice display an enhanced LTP[44]. Therefore the functional deficit is likely to result from its combination with dysregulation of NMDA receptors and possibly other proteins. PSD-95 is phosphorylated by c-Abl and SFKs on several tyrosine residues, which can favor PSD-95 aggregation and GluN2A activation[28,45]. Thus, there appears to be a reciprocal interaction between Pyk2 and PSD-95, each enhancing the function of the other, thereby directly and indirectly regulating NMDA receptors and PSD organization. In support of this functional association, it has been reported that in hippocampal neurons in culture, corticosterone-induced recruitment of Pyk2, PSD-95, and GluN1 to spines requires Pyk2 activation[46]. NMDA receptor activation recruits Pyk2 to spines through its interaction with PSD-95[5], whereas it also rapidly destabilizes PSD-95 and removes it from PSDs[47]. Our study shows that Pyk2 is required for the later recruitment of PSD-95 to spines revealing its contribution in the coordinated $Ca^{2+}$-dependent dynamics of PSD proteins, a key aspect of synaptic function and plasticity. Importantly, GluN2A, GluN2B, and PSD-95 co-assemble together with PSD-93 into 1.5 MDa "supercomplexes"[48]. PSD-93 is phosphorylated by Fyn[49], which is altered in PyK2 mutant mice. Since both PSD-93 and PSD-95 promote Fyn-mediated tyrosine phosphorylation of GluN2A and/or GluN2B[50,51], it appears that Pyk2 is potentially located at a strategic location to regulate NMDA receptor supercomplexes. Since these supercomplexes have been proposed to be functionally important, with mutations in their key components resulting in abnormal LTP and learning[48], it will be particularly interesting to investigate whether their alteration accounts for LTP and other synaptic deficits in Pyk2 mutant mice.

Dendritic spine density and length were also altered in Pyk2 mutant mice. Our study of the requirement of Pyk2 protein domains and functions for its various roles reveals the complexity of its contribution. The kinase activity of Pyk2 and its autophosphorylation site, Tyr402, which is critical for the recruitment of SFKs, were both necessary for the rescue of PSD-95 clustering in spines in Pyk2 KO neurons. The C-terminal region, which allows interaction with PSD-95[14], was also required for PSD-95 clustering. In contrast, rescue of spine density required the C-terminal region but neither Tyr402 nor the kinase activity, indicating a phosphorylation-independent role of Pyk2 in the regulation of spine number. Such an autophosphorylation/kinase activity-independent function of Pyk2 is reminiscent of those reported for the closely related FAK[52,53] in non-neuronal cells. This alternate signaling is presumably SFK-independent and may be linked to scaffolding properties of Pyk2 and/or its interaction with specific partners.

The current study also suggests a role for Pyk2 at the presynaptic level. Our electron microscopy experiments show the presence of Pyk2 in nerve terminals, confirming previous biochemical observations[54]. Its functional role is indicated by the alteration in paired-pulse facilitation, a form of short-term plasticity that is considered to be mostly presynaptic[55,56], although post-synaptic mechanisms are also possible[57]. Finally, in the absence of Pyk2 spine length was decreased both in vivo and in culture. A possible explanation for this lack of rescue could be a dual role of Pyk2 at the pre- and post-synaptic levels, which were not simultaneously restored at the same synapses in the culture conditions in which the transfection rate was low. At any rate, the mechanisms by which Pyk2 controls spine length are likely to be complex since both positive and negative effects of Pyk2 and FAK on spine growth have been previously reported[58-60] and their elucidation will require further investigation. The important aspect of the present results is the overall deficit in spine number and length in the absence of Pyk2. Interestingly, it has been shown that chronic stress induces a redistribution of activated Pyk2 to the perinuclear region of CA3 neurons, contributing to a deficit in the nuclear pore protein NUP62 and its potential negative consequences on dendritic complexity[61]. The present study suggests that Pyk2 redistribution could also directly contribute to dendritic or synaptic alterations by reducing its local levels.

Our observations thus disclose an essential and complex role of Pyk2 in the regulation of spines, PSDs, and NMDA receptors, whose alterations impair synaptic plasticity and hippocampal-dependent memory in Pyk2-deficient mice. The importance of Pyk2 expression levels is underlined by the unexpected severity of the functional deficits in heterozygous mutant mice. Their behavioral and physiological phenotype was as severe as in homozygous mutant mice, whereas a clear gene dosage effect was observed at the molecular level. This suggests that Pyk2 expression is a critical limiting factor for excitatory synapses function in hippocampus and raises the question of the possible implications of decreased Pyk2 protein levels in pathological conditions. This hypothesis was strongly supported by our results in HD. Pyk2 was decreased in grade 3-4 HD patients and in the R6/1 mouse model of the disease, to a level comparable to that observed in Pyk2+/− heterozygous mutant mice, which displayed a clear behavioral phenotype. Several alterations in R6/1 mice were similar to those in Pyk2 mutant mice including the alterations in NMDA receptors, PSD-95 distribution, and spines. Of course such alterations could potentially result from different mechanisms in the two types of mutant mice, but our results provide strong evidence that Pyk2 deficit is a key player in some of the abnormalities observed in R6/1 mice. Even though enhancing Pyk2 expression by AAV transduction in R6/1 mice was not sufficient to restore a normal LTP in CA1, it corrected several behavioral, molecular and cellular deficits. Thus, our study demonstrates the contribution of Pyk2 in the disease manifestations. Interestingly, the deleterious consequences of Pyk2 deficit are likely to synergize with other factors including increased activity of STEP[62], a tyrosine phosphatase active on Pyk2[63] which is expected to aggravate the functional consequences of Pyk2 insufficiency. Our results suggest that strategies for enhancing Pyk2 expression or activity, or for inhibiting STEP phosphatase activity[64] could have a potential therapeutic interest in HD. Further work will determine whether Pyk2 deficiency could play a role in other neurodegenerative conditions, such as Alzheimer disease[8], besides its possible role as modulator of Tau toxicity[65].

Our study reveals that the absence of Pyk2 has dramatic consequences on synaptic functions and hippocampal-dependent learning and memory. We show that Pyk2 plays critical roles in spines and PSD organization and in the regulation of PSD-95 and NMDA receptors. Although we focused our investigations on hippocampus where Pyk2 expression is the highest, it is likely that it is also important in other neurons, especially in neocortical areas where it is highly expressed and which are known to undergo intense synaptic plasticity. We also reveal the contribution of Pyk2 in hippocampal dysfunction in Huntington's disease and its potential reversibility. Our results should stimulate research on the role of Pyk2 in other pathological conditions in which NMDA receptor dysfunction is directly or indirectly thought to be involved.

EXAMPLE 2: ALZHEIMER'S DISEASE

Material & Methods
Mouse Lines

We used the transgenic mouse line 5×FAD, which overexpress the 695-amino acid isoform of the human amyloid precursor protein (APP695) carrying the Swedish, London, and Florida mutations, under the control of the murine Thy-1 promoter. In addition, these mice express human presenilin-1 (PSEN-1) carrying the M146L/L286V mutations, also under the control of the murine Thy-1 promoter (Oakley et al., 2006 J. Neurosci. 26, 10129-10140). We crossed 5×FAD mice with the recently generated Pyk2 knockout (Pyk2$^{-/-}$) mice (Giralt et al., 2016) in order to obtain 5×FAD mice that are knockout for the Pyk2 gene. Mouse genotyping for Pyk2$^{-/-}$ and 5×FAD mice has already been described (Giralt et al., 2016; Oakley) and was carried out from a tail biopsy by Charles River services. The animals were housed with access to food and water ad libitum in a colony room kept at 19-22° C. and 40-60% humidity, under a 12:12 h light/dark cycle. Animals were all used at 8 months of age and in accordance with the ethical guidelines (Declaration of Helsinki and NIH, publication no. 85-23, revised 1985, European Community Guidelines, and French Agriculture and Forestry Ministry guidelines for handling animals, decree 87849, license A 75-05-22) and approved by the local ethical committee.

Human Samples

Prefrontal cortex samples were from 5 controls and 5 AD patients.

Western Blot

Mice were deeply anesthetized in a $CO_2$ chamber, the brains quickly removed, hippocampus dissected out, frozen in dry ice, and stored at −80° C. until use. Briefly, tissue was sonicated in 250 mL of lysis buffer made of phosphate buffered saline (PBS, NaCl, 137 mM, KCl, 2.7 mM, $Na_2HPO_4$, 10 mM, $KH_2PO_4$, 1.8 mM, pH 7.5) with 1% Nonidet P40 (vol/vol), 1 g/L sodium dodecylsulfate (SDS), 5 g/L sodium deoxycholate, protease inhibitors cocktail 1:1,000 (Sigma), and 2 g/L sodium orthovanadate), centrifuged at 12,000 r.p.m. for 20 min and the pellet was discarded. Prefrontal cortex tissue from post-mortem AD patients was prepared similarly. Proteins (15 mg) from hippocampal or cortical tissue were analyzed by SDS-polyacrylamide gel electrophoresis (7.5% acrylamide, WT/vol) and transferred to nitrocellulose membranes (Millipore, Bedford, Mass.). Membranes were blocked in TBS-T (150 mM NaCl, 20 mM Tris-HCl, pH 7.5, 0.05% [vol/vol] Tween 20) with 50 g/L non-fat dry milk and 50 g/L BSA. Immunoblots were probed with rabbit antibodies for GFAP (1:1,000, Z033429, DAKO A/S, Glostrup, Germany), Pyk2 (1:1,000, P3902, Sigma, Saint Louis Mich.), phospho-Tyr402-Pyk2 (1:1,000, 44618G, Invitrogen, Carlsbad, Calif.), Src (1,000, sc-18 (SRC2) Santa Cruz Biotechnology, Santa Cruz, Calif., USA) or alpha-Tubulin (1:1,000, T9026, Sigma). All blots were incubated overnight at 4° C. with shaking, in the presence of the primary antibody in PBS with 0.2 g/L sodium azide. After several washes in TBS-T, blots were incubated with anti-rabbit IgG IRdye800CW-coupled or antimouse IgG IRdye700DXcoupled antibodies (1/2,000, Rockland Immunochemicals, USA) and signal detected by the Odyssey system (Li-Cor) and analyzed using ImageJ.

Tissue Fixation and Immunofluorescence

Animals were deeply anesthetized with pentobarbital (60 mg/kg) and intracardially perfused with a 4% (WT/vol) paraformaldehyde solution in 0.12 M sodium phosphate, pH 7.2. Brains were removed and post-fixed overnight in the same solution, cryoprotected with 300 g/L sucrose in 20 mM sodium phosphate, pH 7.5, 150 mM NaCl (PBS) with 0.2 g/L sodium azide and frozen in dry ice-cooled isopentane. Serial coronal sections (30 µm) obtained with a cryostat were processed for immunohistochemistry as free floating sections. They were washed three times in PBS, permeabilized 15 min by shaking at room temperature with PBS containing (vol/vol) 0.3% Triton X-100 and 3% normal goat serum (Pierce Biotechnology, Rockford, Ill.). After three washes, brain sections were incubated overnight (o.n.) by shaking at 4° C. with antibodies for Abeta (mouse 1:100, 218111, beta-APP Clone NT78. Synaptic Systems. Gottingen), PSD-95 (rabbit, 1:400, Cell Signaling Technology. Beverly, Mass.), synaptophysin 1 (mouse, 1:500, 101011, Synaptic Systems) or anti-Pyk2 (rabbit, 1:400, Sigma) in PBS with 0.2 g/L sodium azide. After incubation with primary antibody, sections were washed three times and then placed 2 h on a shaking incubator at room temperature with the subtype-specific fluorescent secondary 488 anti-rabbit or anti-mouse 555 (1:250, Molecular Probes, Sunnyvale, Calif.). No signal was detected in control sections incubated in the absence of the primary antibody.

Confocal Imaging and Analysis

Dorsal hippocampus in fixed tissue was imaged using a Leica Confocal SP5-II with a 63× numerical aperture lens with 5× digital zoom and standard (1 Airy disc) pinhole (1 AU) and frame averaging (4 frames per z-step) held constant throughout the study. Confocal z-stacks were taken every 0.2 µm for in vitro experiments and every 2 µm for in vivo experiments, at 1,024×1,024 pixel resolution. The number of labeled PSD95- and synaptophysin 1-positive clusters were analyzed with the NIH ImageJ freeware (Wayne Rasband, NIH), as previously described with minor changes (Prange & El-Husseini et al., 2004 PNAS). For in vivo imaging analysis, at least 3 slices of 30 µm containing dorsal hippocampal tissue were analyzed for each mouse and up to 3 representative images, from CA1-stratum radiatum layer, were obtained from each slice.

Fluorescence Microscopy and Plaque Analysis

Stained beta-amyloid plaques were photographed from the entire hippocampus, from three slices per animal containing the dorsal hippocampus on a DM6000-2 microscope (Leica). Files were analyzed with the ImageJ software and plaques were counted manually in the three hippocampal subregions CA1, CA3 and DG.

Electron Microscopy and Immunocytochemistry

Mice were transcardially perfused with a solution containing 40 g/L paraformaldehyde and 1 g/L glutaraldehyde in 0.1 M phosphate buffer (PB composition), pH 7.4. Brains were then immersed in the same fixative for 12 h at 4° C. Tissue blocks containing the hippocampus were dissected and washed in 0.1 M PB, cryoprotected in 100 and 200 g/L sucrose in 0.1M PB, freeze-thawed in isopentane and liquid nitrogen. Samples were postfixed in 25 g/L glutaraldehyde made up in 0.1 M PB for 20 min, washed and treated with 20 g/L osmium tetroxide in PB for 20 min. They were dehydrated in a series of ethanol and flat embedded in epoxy resin (EPON 812 Polysciences). After polymerization, blocks from the CA1 region were cut at 70-nm thickness using an ultramicrotome (Ultracut E Leica). Sections were cut with a diamond knife, picked up on formvar-coated 200 mesh nickel grids. For etching resin and remove osmium, sections were treated with saturated aqueous sodium periodate ($NaIO_4$). They were then immunostained with rabbit antibodies for Pyk2 (Sigma) and Abeta (Synaptic Systems) following the method described by Slot and Geuze (2007) by indirect immunolabeling protein A-gold probes (20 nm) (CMC Utrecht; Netherlands). After immunolabeling the sections were double stained with uranyl acetate and lead citrate prior to observation with a Philips (CM-100) electron microscope. Digital images were obtained with a CCD camera (Gatan Orius). To test the specificity of the immunostaining procedure, the primary antibody was omitted.

Behavioral Tests

To analyze mouse anxiety, we used the elevated plus maze paradigm. Briefly, the plus maze was made of plastic and consisted of two opposing 30×8 cm open arms, and two opposing 30×8 cm arms enclosed by 15 cm-high walls. The maze was raised 50 cm above the floor and lit by dim light. Each mouse was placed in the central square of the elevated plus maze, facing an open arm and its behavior was scored for 5 min. At the end of each trial, any defecation was removed and the apparatus was wiped with 30% alcohol. We recorded the time spent in the open arms, which normally correlates with low levels of anxiety. Animals were tracked and recorded with SMART junior software (Panlab, Spain).

To measure spontaneous locomotor activity we used the open field. Briefly, the apparatus consisted of a white square arena measuring 40×40×40 cm in length, width and height respectively. The dim light intensity was 60 lux throughout the arena. Animals were placed at the arena center and allowed to explore freely for 30 min. Spontaneous locomotor activity was measured. At the end of each trial, any defecation was removed and the apparatus was wiped with 30% ethanol. Animals were tracked and recorded with SMART junior software (Panlab, Spain).

The device for the novel object recognition test (NORT) consisted in a white square arena measuring 40×40×40 cm in length, width and height respectively. The light intensity was 60 lux throughout the arena and the room temperature was kept at 19-22° C. and 40-60% humidity. Mice were first habituated to the arena in the absence of objects (3 days, 15 min/day). On the fourth day, two similar objects were presented to each mouse during 10 min (A'A" condition) after which they were returned to their home cage for 15 min. After that, the animals were placed in the arena where they were tested during 5 min with a familiar and a new object (A' B condition; short-term memory, STM), and then returned to their home cage. Twenty-four hours later, the same animals were re-tested for 5 min in the arena with a familiar and a new object (BC condition; long-term memory, LTM). The object preference was measured as the time spent exploring each object×100/time exploring both objects. The arena was rigorously cleaned with 30% alcohol between animal trials in order to avoid odors.

The passive avoidance (light-dark) paradigm was conducted in a 2-compartment box, where 1 compartment was dimly lit (20 lux) and preferable to a rodent, and the other compartment was brightly lit (200 lux); both chambers were connected by a door (5 cm×5 cm). During training, mice were placed into the aversive brightly lit compartment, and upon the entry into the preferred dimly lit compartment (with all 4 paws inside the dark chamber), mice were exposed to a mild foot shock (2-second foot shock, 1 mA intensity). The latency of mice to enter into the dark chamber was recorded. Twenty seconds after receiving the foot shock, mice were returned to the home cage until testing, which was carried out 24 hours later (long-term memory). For this retention test, mice were returned to the brightly lit compartment again, and the latency to enter the shock-paired compartment (dark chamber) was measured (retention or recall latency). Ten minutes was used as a time cutoff in the retention test. The animal that learned the task would avoid the location previously paired with the aversive stimulus, and would show greater latency to enter it.

Viral Constructs and Stereotaxic Injection

For specific over-expression of Pyk2 in the hippocampus we stereotaxically injected adeno-associated viruses (AAV) expressing Pyk2 (AAV1-CamKIIα(0.4)-GFP-2A-mPTK2B; Vector Biolabs Malvern, Pa., USA). As a control we injected AAVs expressing GFP (AV-9-PV1917, AAV9.CamKIIα (0.4).eGFP.WPRE.rBG (AAV-GFP) from Perelman). Following anesthesia with pentobarbital (30 mg/kg), we performed bilateral injections of AAV-GFP or AAV-Pyk2 (1 $3.06 \times 10^9$ GS) in the dorsal hippocampus following coordinates from the bregma (millimeters); anteroposterior, $-2.0$; lateral, $+/-1.5$; and dorsoventral, $-1.4$ and $-2.0$ in order to transduce the CA1-CA3 and DG. AAVs were injected over 2 minutes, leaving the cannula in place for 5 additional minutes to ensure complete diffusion of the viruses, and then slowly retracted from the brain. The animals were monitored for 2 hours after administration and then returned to the housing facility for 21 days. After this period, animals were subjected to behavioral assessment and morphological and biochemical analysis.

Statistical Analysis

All data are expressed as mean±SEM. Statistical analysis were performed using the two-tailed unpaired Student's t-test, one-way ANOVA with the Tukey's post hoc test, two-way ANOVA with the Bonferroni's post hoc test as appropriate and indicated in the figure legends. Values of $p<0.05$ were considered as statistically significant.

Results

Figure 9C:
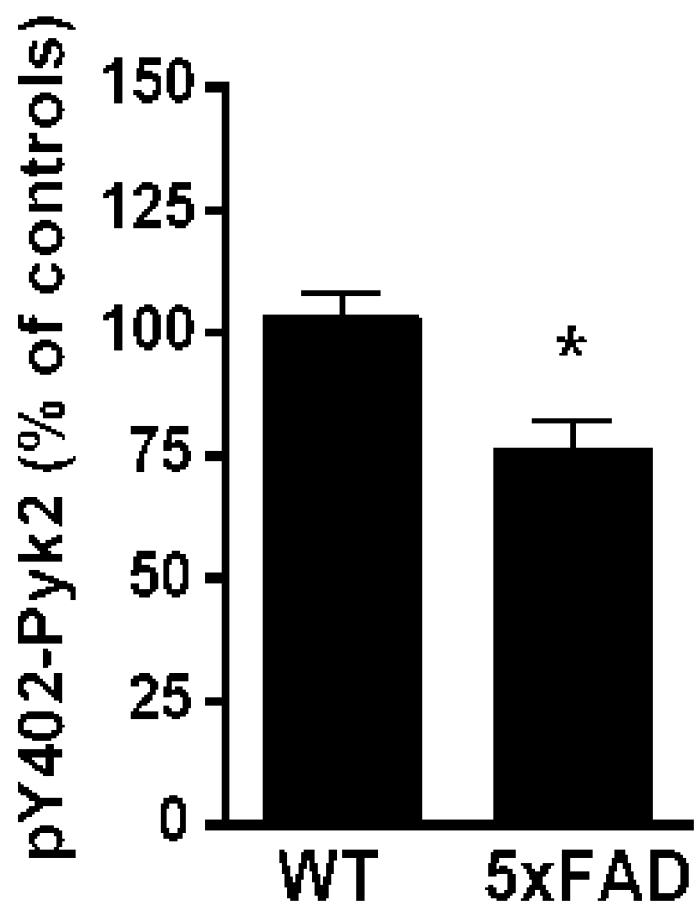

Characterization of Pyk2 Levels and Localization in the 5×FAD Mouse Model of Alzheimer Disease To explore Pyk2 in Alzheimer disease (AD) we first examined by immunoblotting its protein levels in pre-frontal post-mortem samples from AD patients. Pyk2 levels were unchanged. We then analyzed Pyk2 and pTyr402-Pyk2 levels in the hippocampus of 8-month old 5×FAD transgenic mice. Total Pyk2 levels were similar in WT and 5×FAD mice (FIGS. 9A and B). In contrast, pTyr402-Pyk2 levels were decreased in the hippocampus of 5×FAD mice compared to WT mice (FIG. 9C). In human samples due to long and variable post-mortem delays no signal for pTyr402 was detectable.

We then evaluated the localization of Pyk2 in the hippocampus of 5×FAD mice and its relation with Aβ amyloid labeling and plaques. We first observed that Aβ amyloid-positive plaques were completely negative for Py2 staining in the hippocampus of 5×FAD mice. In contrast, Pyk2 and Aβ-like immunoreactivity were colocalized in neuropil zones without amyloid plaque formation. We observed a strong colocalization between Pyk2 and Aβ amyloid-positive staining in all the hippocampal regions. We studied this colocalization with electron microscopy and found that gold particles for Pyk2 and Aβ were in close vicinity at both pre and post-synaptic levels. Altogether suggests that Pyk2 activity and location could be altered in 5×FAD mice.

Genetic Deletion of Pyk2 does not Change the Behavioral Phenotype in 5×FAD Mice

Figure 10A:
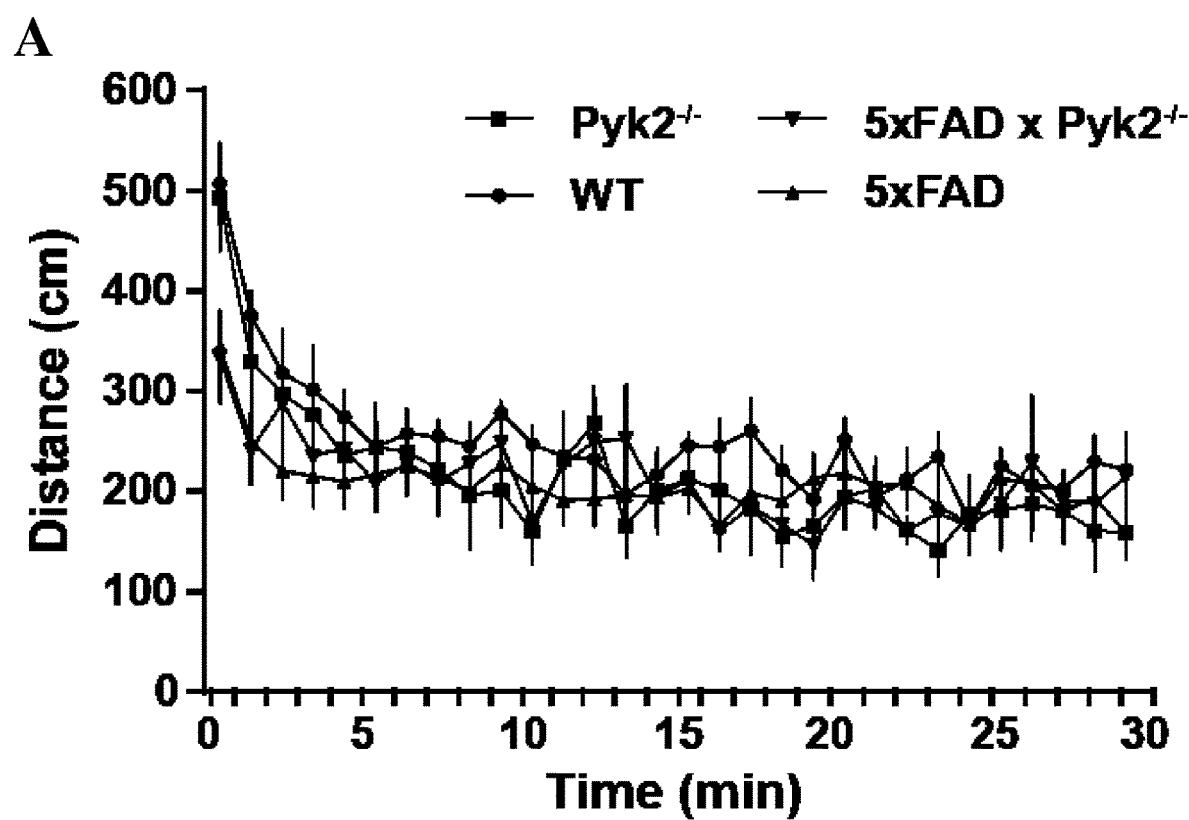

We next sought to test whether the 5×FAD phenotype could be modified by decreasing Pyk2 levels. We crossed 5×FAD mice with Pyk2$^{-/-}$ mice to obtain double mutant mice bearing the human Alzheimer mutations and a functional deletion of the PTK2B gene. The resulting double mutant 5×FAD×Pyk2$^{-/-}$ mice were then characterized at 8 months of age. First, we verified the absence of Pyk2 in 5×FAD×Pyk2$^{-/-}$ mice. Then we carried out a set of behavioral tests to evaluate the neurological and cognitive state in the four genotypes. Since reduced locomotion has been reported in aged 5×FAD mice (Schneider et al., 2014 http://dx.doi.org/10.1016/j.physbeh.2014.05.041; Griñàn-Ferrè et al., AGING, March 2016, Vol. 8 No. 3), we evaluated the spontaneous locomotor activity in the open field during 30 min of WT, Pyk2$^{-/-}$, 5×FAD and 5×FAD×Pyk2$^{-/-}$ mice. All the groups habituated and displayed a similar locomotor activity in the new arena environment (FIG. 10A). Next, we explored short- and long-term memory capabilities in all four genotypes. Since we have previously shown that by itself Pyk2 mutation impairs hippocampus-dependent spatial memory, we used the novel object recognition test (NORT, FIGS. 10B and C). We first habituated all mice to the open field arena and ambient conditions during three consecutive days. After the habituation process, animals were exposed to two similar objects (A and B). All groups similarly explored both objects indicating the lack of spontaneous object or place preference (data not shown). When mice were assessed for short-term memory (STM) by replacing one of the objects by a new one, 20 min after training, all groups preferentially explored the novel object without significant differences between genotypes (FIG. 10B). These results indicated that STM was not affected in any genotype compared to WT mice. Long-term memory (LTM) was then assessed by replacing the previously unchanged object by a new one 24 h later (FIG. 10C). Although WT and Pyk$^{-/-}$ mice explored more the new object than the familiar one, this preference for the new object was completely absent in 5×FAD and 5×FAD×Pyk2$^{-/-}$ mice. These results indicated specific LTM deficits in 5×FAD which were not modified in 5×FAD×Pyk2$^{-/-}$ mice. We next examined associative memory in the passive avoidance task, based on the association formed between an aversive stimulus (electrical foot shock) and a specific environmental context (light-dark, FIG. 10D). Latency to step-through during the training session was similar between genotypes. However, in the testing session, 24 hours after receiving an electrical shock, although all genotypes showed a pronounced increase in the latency to enter the dark compartment, this latency was lower in 5×FAD mutant mice than in WT littermates, revealing a memory deficit (FIG. 10D). A shorter latency was also observed in Pyk2$^{-/-}$ and 5×FAD×Pyk2$^{-/-}$ mice, without significant difference between genotypes (FIG. 10D). Thus, associative memory was similarly impaired in all genotypes compared to WT mice. These results showed that Pyk2 deletion induced by itself a deficit in the passive avoidance performance, and that this deficit was not additive to the alterations observed in 5×FAD mice and did not improve it. Finally, to further characterize the behavioral phenotype of the 5×FAD×Pyk2$^{-/-}$ mice, compared to 5×FAD mice, we used the plus maze, which is mainly used to evaluate anxiety levels. As previously described (Schneider et al., 2014; Griñàn-Ferrè et al., 2016) we observed that 5×FAD mice spent significantly more time in the open arms than their WT littermates (FIG. 10E). Pyk2$^{-/-}$ mice did not differ from WT mice, whereas 5×FAD×Pyk2$^{-/-}$ spent more time in the open arms as the 5×FAD simple mutants (FIG. 2F). These results confirm an altered behavior of 5×FAD mutant mice, possibly linked to decreased anxiety levels, which was not modified by Pyk2 KO.

Genetic Deletion of Pyk2 Induces Minor Changes in 5×FAD Mice Neuropathology

To test whether the lack of Pyk2 can exacerbate or ameliorate β-amyloidosis and astrogliosis in 8-month old 5×FAD mice we carried out an immunofluorescence for A1338-43 and counted the number of plaques in the three regions of the hippocampus (CA1, CA3 and DG) in 5×FAD and 5×FAD×Pyk2$^{-/-}$ mice (FIG. 11A). Aβ$_{38-43}$ immunostaining revealed that hippocampal plaque loads in 5×FAD× Pyk2$^{-/-}$ mice at 8 months of age were indistinguishable from those in age-matched 5×FAD mice in CA1 and DG. However, in the CA3 region we detected a decrease in the number of plaques in 5×FAD×Pyk2$^{-/-}$ mice compared to 5×FAD mice. We then examined by immunoblotting the hippocampal protein levels of the glial fibrillary associated protein (GFAP) to evaluate whether astrogliosis was altered in 5×FAD:Pyk2$^{-/-}$ mice compared to 5×FAD mice (FIG. 11B). GFAP levels were increased in both 5×FAD and 5×FAD×Pyk2$^{-/-}$ mice as compared to WT and Pyk2$^{-/-}$ mice. However, these levels were similar in 5×FAD×Pyk2$^{-/-}$ mice and 5×FAD mice. In summary, the genetic deletion of Pyk2 did not alter the amyloid plaques or astrogliosis in 5×FAD mice, except for a small decrease in the number of plaques in the CA3 region.

Pyk2 Overexpression in the Hippocampus Ameliorates the Behavioral Phenotype of 5×FAD Mice Our results with 5×FAD×Pyk2$^{-/-}$ mice showed that the absence of Pyk2 did not markedly modify the phenotype of Pyk2 5×FAD mice. Since the phosphorylation of Pyk2 on Tyr402 was decreased in these mice, suggesting a functional alteration, we decided to explore the effects of Pyk2 over expression. We targeted the hippocampus, a well-defined region which plays an important role in 5×FAD mice phenotype. Eight-month old WT and 5×FAD mice received a bilateral stereotactic injection into the hippocampus of adeno-associated virus expressing Pyk2 (5×FAD/Pyk2 mice) or expressing GFP (WT/GFP and 5×FAD/GFP mice), as a control. Three weeks after AAV injection, Pyk2 protein levels increased in 5×FAD/Pyk2 mice as compared to WT/GFP and 5×FAD/GFP mice (FIG. 12A). This increase of total Pyk2 levels in 5×FAD/Pyk2 was accompanied by a rescue of hippocampal pTyr402-Pyk2 levels as compared to 5×FAD/GFP mice (FIG. 12B).

Figure 12E:
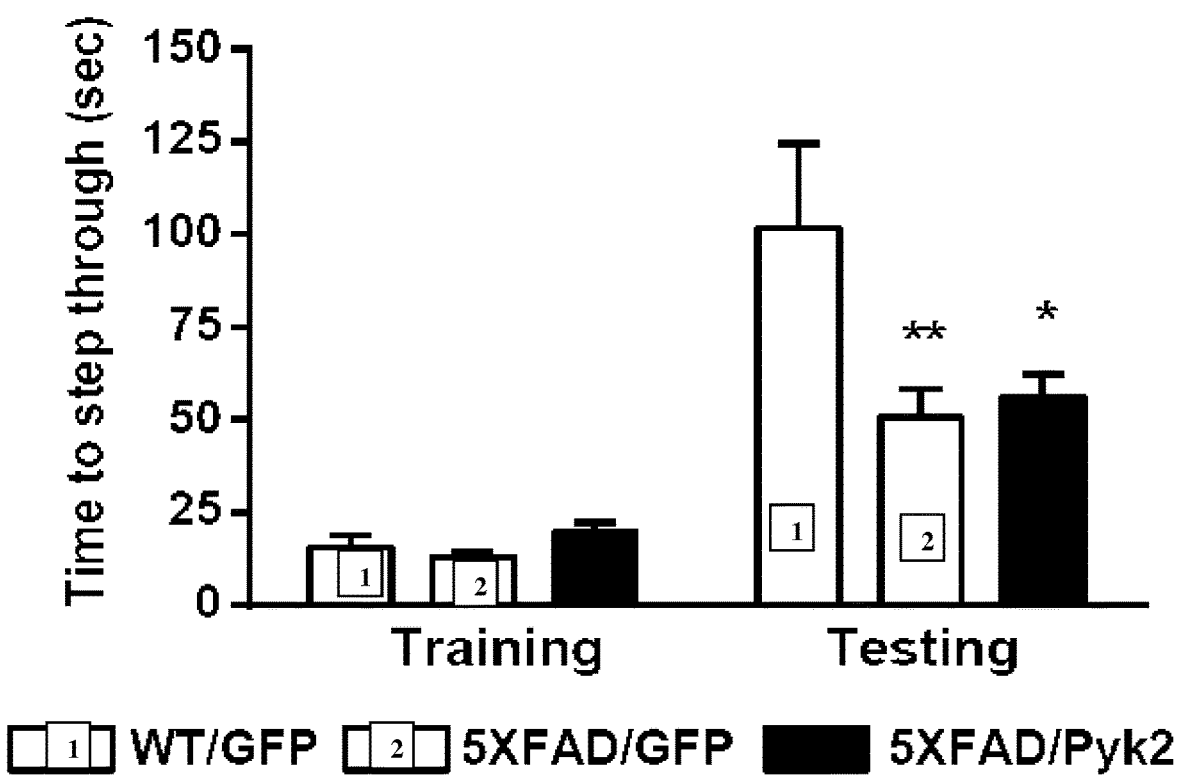

We then conducted the same set of behavioral tests to evaluate the neurological and cognitive state in the three groups as in Pyk2 KO mice (see above FIG. 10). In the elevated plus maze (FIG. 12C) the increase in time spent in the open arms by 5×FAD/GFP mice compared with WT-GFP mice was corrected in 5×FAD/Pyk2 mice. When we evaluated locomotor activity for 30 min in the open field all groups had a similar activity (FIG. 12D). Next we subjected the WT/GFP, 5×FAD/GFP, and 5×FAD/Pyk2 mice to the passive avoidance test to evaluate associative learning (FIG. 12E). Latency to step through during the training session was similar between genotypes. However, in the testing session, although all genotypes showed a significant increase in the latency to enter the dark compartment 24 hours after receiving an electrical shock, this latency was lower in 5×FAD/GFP and 5×FAD/Pyk2 mice than in WT/GFP mice. Furthermore, no differences were observed between 5×FAD/GFP and 5×FAD/Pyk2 mice. Thus, overexpression of Pyk2 in the hippocampus did not restore the associative memory evaluated in the passive avoidance paradigm. Finally, we carried out the NORT paradigm in the three groups of mice (FIGS. 12F and G). As observed in FIG. 2 in the absence of AAV injection, the 5×FAD/GFP mice displayed a deficit in long-term memory (FIG. 12G) but not short term memory, as compared to WT/GFP mice (FIG. 12F). In contrast, this deficit in long-term memory was not found in 5×FAD-Pyk2 mice (FIG. 12G), indicating that hippocampal overexpression of Pyk2 rescued the cognitive deficits of 5×FAD mice in the NORT paradigm. Together these results showed that bilateral overexpression of Pyk2 in the hippocampus of 5×FAD mice rescued some components of their behavioral phenotype, including apparent anxiety in the elevated plus maze and NORT.

Pyk2 Overexpression in the Hippocampus Increases the Number of Plaques without Changing the Astrogliosis Levels To test whether the overexpression of Pyk2 in the hippocampus modified β-amyloidosis in 5×FAD mice we carried out an immunofluorescence for Aβ$_{38-43}$ in 8-month old 5×FAD/GFP and 5×FAD/Pyk2 mice and counted the number of plaques in the three regions of the hippocampus (CA1, CA3, and DG, FIG. 13A). Aβ$_{38-43}$ immunostaining revealed that the plaque number was higher in all the hippocampal regions in 5×FAD/Pyk2 than in 5×FAD/GFP mice. We then examined by immunoblotting the hippocampal protein levels of the glial fibrillary associated protein (GFAP) to evaluate whether astrogliosis was altered in the same groups of mice (FIG. 13B). GFAP levels were increased in both 5×FAD/ GFP and 5×FAD/Pyk2 mice as compared to WT/GFP mice but were similar in 5×FAD/Pyk2 and 5×FAD/GFP mice. In summary, the local hippocampal overexpression of Pyk2 in 5×FAD mice increased the number of Aβ-amyloid plaques in the hippocampus although it did not induce any gross changes in hippocampal astrogliosis.

Pyk2 Over-Expression in the Hippocampus Rescues the Loss of Synaptic Markers in the CA1 of 5×FAD Mice Since two of the major neuropathological markers (astrogliosis and Aβ-amyloid loading) of 5×FAD/Pyk2 mouse line do not correlate positively with the cognitive improvements observed in this group, we then focused on the study of putative changes in synaptic architecture. It has already been described that pre- and post-synaptic markers such as PSD95 and Synaptophysin are decreased in 5×FAD mice models mice correlating well with cognitive decline (Hongpaisan et al., 2011 J Neurosci OI:10.1523/JNEURO-SCI.5209-10.2011; Griñàn-Ferrè et al., 2016; Shao et al., 2011 Acta Neuropathol 10.1007/s00401-011-0843-x). Thus, we wanted to analyze the state of two markers in the stratum radiatum of the CA1 in WT/GFP, 5×FAD/GFP and 5×FAD/ Pyk2 mice.

First, we demonstrated that 5×FAD/GFP mice displayed a significant decrease in the number of PSD-95-positive puncta compared to WT/GFP mice in the stratum radiatum of the CA1 (FIG. 14A). Interestingly, this decrease was rescued in 5×FAD/Pyk2 mice suggesting that over-expression of Pyk2 in the 5×FAD hippocampus restores the levels and the location of PSD-95-positive puncta. In the same line, we also analyzed the number of Synaptophysin-positive puncta in the stratum radiatum of the CA1 in all three groups (FIG. 14B). The Synaptophysin-positive particles analysis revealed that the number of Synaptophysin-positive puncta was also altered in the stratum radiatum of the 5×FAD/GFP mice compared to WT-GFP control group. In contrast, the number of Synaptophysin-positive particles in 5×FAD/Pyk2 mice was recovered being this group indistinguishable from WT/GFP mice for this parameter. These results suggest that the phenotype improvement observed in 5×FAD/k2 mice compared to 5×FAD-GFP mice correlate very well with a rescue in the number and location of pre- and post-synaptic markers indicating improvements in the synaptic architecture of the 5×FAD/Pyk2 mice.

Loss of Pyk2 Levels/Function Induce Src Cleavage

The previous results together pointed to a putative loss of normal function rather than a gain of toxic function of Pyk2 in the 5×FAD mouse model of AD. We then wandered by which molecular mechanism Pyk2 loss of function could induce detrimental and neuropathological processes that would facilitate the appearance or maintenance of the disease. In this line, it has been described that the Src kinase activity, a main downstream target recruited by Pyk2 and that it depends on the Pyk2 phosphorylation (Dikic et al., 1996 Nature. 10.1038/383547a0), is cleaved under neurotoxic and neurodegenerative conditions such as ischemic insults (Hossain et al., 2013 JBC). Interestingly, this cleavage produces a Src product of ~52 kDa which has been described to induce excitotoxicity. Thus, we sought to test whether the lack of Pyk2 could induce Src cleavage producing these ~52 kDa toxic fragments.

To explore this possibility we examined by immunoblotting in hippocampal samples the protein levels of the Src kinase by using an antibody (the SRC2) that recognizes the C-terminal. This antibody allowed to us to detect total and cleaved Src forms. By using this approach we observed that $Pyk2^{+/+}$ control mice did not show a large decrease in total Src (FIG. 15A). However, $Pyk2^{+/-}$ mice showed a significant increase of the cleaved Src. This cleavage was even much more pronounced in $Pyk2^{-/-}$ mice indicating a clear genetic dosage effect on this cleavage. Importantly, we also observed a significant increase in Src cleavage in 5×FAD/GFP mice compared to WT/GFP controls (FIG. 15B). These increased levels of Src cleavage were normalized in 5×FAD/Pyk2 strongly correlating with a recovery of pTyr402-Pyk2 levels in such animals compared to 5×FAD/GFP mice (15C and D). These results indicate that a strong correlation exists between the recovery of pTyr402-Pyk2 levels, the normalization of cleaved Src and the improvements in synaptic architecture and cognitive function in 5×FAD/Pyk2 mice compared with 5×FAD/GFP mice.

Conclusion

In the present work we directly evaluated for the first time the possible role of Pyk2 as a risk factor in AD using an animal model. For that aim we first characterized the levels, activity and location of Pyk2 in the 5×FAD transgenic mouse model of AD and also the total protein levels in human post-mortem samples. We observed a lack of colocalization of Pyk2 with Aβ-amyloid plaques but a strong colocalization between Pyk2 and Aβ-amyloid immunoreactivities in locations without presence of Aβ-amyloid plaques. In line with this, pTyr402-Pyk2 but not total Pyk2 levels were decreased in 5×FAD mice compared to WT mice. Thus, we designed knock-down and over-expression strategies to modulate the Pyk2 levels in 5×FAD mice. We observed that Pyk2 over-expression but not Pyk2 deletion induced significant ameliorations in neurogological and cognitive skills previously described to be affected in 5×FAD mice. These changes correlated well with improvements in hippocampal synaptic architecture. Furthermore, we provide evidence for the first time that a putative molecular mechanism triggered by the Pyk2 loss of function could be a cleavage of the Src kinase likely inducing an initiation of neurotoxic and neurodegenerative processes.

Pyk2 gene (PTK2B) was recently discovered to be associated with an increased risk for AD (Lambert . . . Amouyel 2013 Nat Gen). However, the actual links and potential mechanisms by which the tyrosine kinase could be altering the onset and/or severity of the disease are completely unknown. In the present work we tested whether Pyk2 modifies the disease in an AD model. We first deleted Pyk2 in 5×FAD mice by creating the 5×FAD×$Pyk2^{-/-}$ mice. We did not observe changes in the phenotype of 5×FAD×$Pyk2^{-/-}$ mice compared with 5×FAD mice indicating that the deficits of the $Pyk2^{-/-}$ were similar compared to those in 5×FAD mice. The only exception was a small decrease in the number of Aβ-positive plaques in CA3. This result suggests that genetic deletion of Pyk2 in 5×FAD mice was redundant since Pyk2 activity is already altered in these animals as shown by the decreased pTyr402-Pyk2. In support to this idea, we demonstrated that a partial deletion of Pyk2 in mice (heterozygous mice for Pyk2) induces dramatic changes and alterations in hippocampal-related learning and structural and functional synaptic plasticity. Accordingly, the same type of changes are also seen in the 5×FAD mice (Clinton et al., 2007 j.nbd. 2007.06.013; Knafo et al., 2009 10.1002/path.2565; Oakley et al., 10.1523/JNEUROSCI.1202-06.2006; Shukla et al., 2013 10.1096/fj.12-217497; Zhang et al., 2011 10.1016/j.bbr.2011.03.072). Thus, with the idea of a possible decrease in Pyk2 activity in AD model, we then over-expressed Pyk2 in the hippocampus of 5×FAD mice. We observed a remarkable improvement of several cognitive functions in 5×FAD mice due to the Pyk2 function recovery. Regarding the gross neuropathology we observed that over-expressing Pyk2 did not change astrogliosis in 5×FAD mice. In contrast, over-expression of Pyk2 increased the number of plaques, which is striking since the number of plaques, when reduced, is considered as an amelioration of the 5×FAD mice phenotype (Murphy and LeVine, 2010 10.3233/JAD-2010-1221). However, some previous studies correlated an hyper-aggregation with an improvement of the AD transgenic mice phenotype due to a lower presence of soluble Aβ which is the most toxic form of the molecule (Cohen et al., 2009, 10.1016/j.cell.2009.11.014; Lubin et al., 2010 10.1002/msj.20160; Castellani et al., 2009 10.3233/JAD-2009-1151). In line with this, we observed no colocalization between Aβ-positive plaques and Pyk2 but a strong colocalization between Aβ and Pyk2 immunoreactivities outside of the Aβ-positive plaques, in the CA1-CA3 and in the DG. This result led us to think that the cognitive improvements observed in 5×FAD mice over-expressing Pyk2 could be more related with a synaptic amelioration rather than with neuropathological changes. Thus, we observed that two of the most affected synaptic markers, synaptophysin and PSD-95 (Hongpaisan et al., 2011; Griñàn-Ferrè et al., 2016; Shao et al., 2011), showed a significant and robust rescue in the CA1 of 5×FAD mice over-expressing Pyk2 compared to control 5×FAD mice.

Concerning the molecular mechanisms involved, here we show that a possible role of Pyk2 as a risk factor in AD is a loss of function due to a decrease in its phosphorylation levels at tyrosine 402 which in turn is responsible of its activation and kinase activity initiation (Girault et al., 1999 TINS 22(6):257-63). It has been shown that Pyk2 can regulate long-term potentiation (LTP) (Huang et al., 2001; Giralt et al., 2017), a cellular model of memory storage and synaptic plasticity (Bliss and Collindrige 1993 Sicence). Pyk2 can also regulate the presence of PSD-95 in the excitatory synapses, the density and morphology of dendritic spines and the formation of hippocampal-related memories (Giralt et al., 2017). Furthermore, Pyk2 could modulate the function of N-methyl-D-aspartate receptors (NMDARs) since these molecules co-precipitate in immuno-precipitation studies (Liu et al., Brain Res. 2001 Aug. 3; 909(1-2):51-8; Zalewska et al., 2005 Brain Res. 2005 May 3; 1042(2):214-23.). Interestingly, alterations in NMDARs have already been described in AD mouse models (Kook et al., 2014 10.1038/cdd.2014.67; Liu et al., 2015

Mol Neurodeg 10.1186/s13024-015-0002-2; Wang et al., 2013 10.1007/s12264-013-1383-2). However, although Pyk2 has the potential to directly phosphorylate the different tyrosine residues located in GluN2A-B subunits (Giralt et al., 2017), the exact mechanism remains unclear.

A potential alternative mechanism could be that Pyk2 could regulate indirectly NMDARs and other molecules by an intermediary step such as a modulation of Src kinase family. Indeed, one of the Pyk2 main targets is the recruitment of Src kinase family members in order to induce their activity (Dikic et al., 1996). A deficit in this recruitment could lead to an aberrant phosphorylation state of Src and/or a mislocalization of the protein. Another possibility could be an aberrant degradation or cleavage of Src. It has already been described that neurotoxic/neurodegenerative processes such as ischemic insults induce a cleavage of Src producing a toxic fragment (Hossain et al., 2013 JBC). Here we show that Src is more cleaved in the hippocampus of 5×FAD mice. Furthermore, we show that a partial Pyk2 deficiency is sufficient to induce this cleavage. This is corrected in 5×FAD mice over-expressing Pyk2. We propose that this rescue of Src cleavage could be one of the mechanisms by which Pyk2 over-expression could ameliorate the 5×FAD phenotype for several reasons. First, a Src loss of function has already been described in amyloid beta models of AD inducing LTP alterations (Xiang et al., Neurobiology of Aging 40 (2016) 98e102) and it could explain deficits in PSD-95 localization in the synapse (Kalia and Salter, Neuropharmacology 45 (2003) 720-728). Furthermore, although recovery of Src function could improve synaptic function, it could also increase the Aβ production as described elsewhere (Gianni et al., 2003; 10.1074/jbc.M211899200; Dunning et al., 2016; 10.1111/jnc.13571) and increasing the number of Aβ plaques as we observed in 5×FAD mice over-expressing Pyk2. In accordance, it is noteworthy that the decrease of Aβ plaques in the 5×FAD mice with Pyk2 genetic deletion strengthening such hypothesis.

Taken together these results indicate that there is a possible decrease in Pyk2 activity in AD and that the recovery of its activity by increasing the Pyk2 levels has beneficial effects. However this statement should be taken with caution since the pathway Pyk2-Src kinase family could be directly involved with the formation of Aβ plaques that in turn could be protective if such process is able to prevent the maintenance of soluble and more toxic Aβ oligomers.

EXAMPLE 3: MOTOR DEFICIT IMPAIREMENT IN HUNTINGTON DISEASE

To determine whether the observations on the decreased Pyk2 expression in the hippocampus of patients with Huntington's disease and on the therapeutic potential of increasing Pyk2 levels to improve behavioral symptomatology, we investigated the existence of an alteration of Pyk2 in the striatum, which is central to the movement disorder of the disease.

Pyk2 expression was determined in post-mortem samples from the putamen of 7 patients with Huntington's disease (HD) and 7 controls without striatal alteration. Pyk2 was measured by immunoblotting, quantified with Li-Cor Odyssey and expressed as a percentage of the mean levels in controls. Pyk2 levels were significantly decreased in the putamen of patients (FIG. 16).

Pyk2 expression was then investigated in the striatum of two mouse models of the disease: R6/1 and R6/2 mice. These models were used to determine the time course of Pyk2 variation during the evolution of the disease. Pyk2 levels were investigated by immunoblotting as above. The levels of Pyk2 were significantly decreased in the striatum of R6/1 mice as compared to matched wild type (WT) controls at 20 and 30 weeks of age (FIG. 17).

In R6/2 mice which have a more severe phenotype than R6/1 mice, the levels of Pyk2 were measured at 6 and 12 weeks (FIG. 18). Pyk2 levels were markedly decreased at 12 weeks.

To determine whether it was possible to use an AAV1 expressing Pyk2 to restore the expression of this protein we used a bilateral stereotactic injection of AAV1-GFP-PTK2B in the dorsal striatum of wild type mice. One week later the fluorescence of GFP was observed in neurons of the dorsal striatum in the two sides of the brain (FIG. 19).

REFERENCES

Throughout this application, various references, including United States patents and patent applications, describe the state of the art to which this invention pertains. The disclosures of these references are hereby incorporated by reference in entirety into the present disclosure.

1. Giralt, J. A., Costa, A., Derkinderen, P., Studler, J. M. & Toutant, M. FAK and PYK2/CAKbeta in the nervous system: a link between neuronal activity, plasticity and survival? *Trends Neurosci.* 22, 257-263 (1999).
2. Salter, M. W. & Kalia, L. V. Src kinases: a hub for NMDA receptor regulation. *Nat. Rev. Neurosci.* 5, 317-328 (2004).
3. Lev, S., et al. Protein tyrosine kinase PYK2 involved in Ca(2+)-induced regulation of ion channel and MAP kinase functions. *Nature* 376, 737-745 (1995).
4. Menegon, A., et al. FAK+ and PYK2/CAKbeta, two related tyrosine kinases highly expressed in the central nervous system: similarities and differences in the expression pattern. *Eur. J. Neurosci.* 11, 3777-3788 (1999).
5. Bartos, J. A., et al. Postsynaptic clustering and activation of Pyk2 by PSD-95. *J. Neurosci.* 30, 449-463 (2010).
6. Hsin, H., Kim, M. J., Wang, C. F. & Sheng, M. Proline-rich tyrosine kinase 2 regulates hippocampal long-term depression. *J. Neurosci.* 30, 11983-11993 (2010).
7. Huang, Y., et al. CAKbeta/Pyk2 kinase is a signaling link for induction of long-term potentiation in CA1 hippocampus. *Neuron* 29, 485-496 (2001).
8. Lambert, J. C., et al. Meta-analysis of 74,046 individuals identifies 11 new susceptibility loci for Alzheimer's disease. *Nat. Genet.* 45, 1452-1458 (2013).
9. Walkiewicz, K. W., Giralt, J. A. & Arold, S. T. How to awaken your nanomachines: Site-specific activation of focal adhesion kinases through ligand interactions. *Prog. Biophys. Mol. Biol.* 119, 60-71 (2015).
10. Dikic, I., Tokiwa, G., Lev, S., Courtneidge, S. A. & Schlessinger, J. A role for Pyk2 and Src in linking G-protein-coupled receptors with MAP kinase activation. *Nature* 383, 547-550 (1996).
11. Siciliano, J. C., Toutant, M., Derkinderen, P., Sasaki, T. & Girault, J. A. Differential regulation of proline-rich tyrosine kinase 2/cell adhesion kinase beta (PYK2/CAKbeta) and pp125(FAK) by glutamate and depolarization in rat hippocampus. *J. Biol. Chem.* 271, 28942-28946 (1996).
12. Heidinger, V., et al. Metabotropic glutamate receptor 1-induced upregulation of NMDA receptor current: mediation through the Pyk2/Src-family kinase pathway in cortical neurons. *J. Neurosci.* 22, 5452-5461 (2002).

13. Husi, H., Ward, M. A., Choudhary, J. S., Blackstock, W. P. & Grant, S. G. Proteomic analysis of NMDA receptor-adhesion protein signaling complexes. *Nat. Neurosci.* 3, 661-669 (2000).
14. Seabold, G. K., Burette, A., Lim, I. A., Weinberg, R. J. & Hell, J. W. Interaction of the tyrosine kinase Pyk2 with the N-methyl-D-aspartate receptor complex via the Src homology 3 domains of PSD-95 and SAP102. *J. Biol. Chem.* 278, 15040-15048 (2003).
15. Bongiorno-Borbone, L., Kadare, G., Benfenati, F. & Girault, J. A. FAK and PYK2 interact with SAP90/PSD-95-Associated Protein-3. *Biochem. Biophys. Res. Commun.* 337, 641-646 (2005).
16. Grant, S. G., et al. Impaired long-term potentiation, spatial learning, and hippocampal development in fyn mutant mice. *Science* 258, 1903-1910 (1992).
17. O'Dell, T. J., Kandel, E. R. & Grant, S. G. Long-term potentiation in the hippocampus is blocked by tyrosine kinase inhibitors. *Nature* 353, 558-560 (1991).
18. Okigaki, M., et al. Pyk2 regulates multiple signaling events crucial for macrophage morphology and migration. *Proc. Natl. Acad. Sci. USA* 100, 10740-10745 (2003).
19. A novel gene containing a trinucleotide repeat that is expanded and unstable on Huntington's disease chromosomes. The Huntington's Disease Collaborative Research Group. *Cell* 72, 971-983 (1993).
20. Giralt, A., Coura, R. & Girault, J. A. Pyk2 is essential for astrocytes mobility following brain lesion. *Glia* 64, 620-634 (2016).
21. Assini, F. L., Duzzioni, M. & Takahashi, R. N. Object location memory in mice: pharmacological validation and further evidence of hippocampal CA1 participation. *Behav. Brain Res.* 204, 206-211 (2009).
22. Cunningham, J. I., Raudensky, J., Tonkiss, J. & Yamamoto, B. K. MDMA pretreatment leads to mild chronic unpredictable stress-induced impairments in spatial learning. *Behav. Neurosci.* 123, 1076-1084 (2009).
23. Corvol, J. C., et al. Depolarization activates ERK and proline-rich tyrosine kinase 2 (PYK2) independently in different cellular compartments in hippocampal slices. *J. Biol. Chem.* 280, 660-668 (2005).
24. Gray, N. W., Weimer, R. M., Bureau, I. & Svoboda, K. Rapid redistribution of synaptic PSD-95 in the neocortex in vivo. *PLoS Biol.* 4, e370 (2006).
25. El-Husseini Ael, D., et al. Synaptic strength regulated by palmitate cycling on PSD-95. *Cell* 108, 849-863 (2002).
26. Colledge, M., et al. Ubiquitination regulates PSD-95 degradation and AMPA receptor surface expression. *Neuron* 40, 595-607 (2003).
27. Ehlers, M. D. Activity level controls postsynaptic composition and signaling via the ubiquitin-proteasome system. *Nat. Neurosci.* 6, 231-242 (2003).
28. Perez de Arce, K., et al. Synaptic clustering of PSD-95 is regulated by c-Abl through tyrosine phosphorylation. *J. Neurosci.* 30, 3728-3738 (2010).
29. Zhang, J., Petit, C. M., King, D. S. & Lee, A. L. Phosphorylation of a PDZ domain extension modulates binding affinity and interdomain interactions in postsynaptic density-95 (PSD-95) protein, a membrane-associated guanylate kinase (MAGUK). *J. Biol. Chem.* 286, 41776-41785 (2011).
30. Faure, C., et al. Calcineurin is essential for depolarization-induced nuclear translocation and tyrosine phosphorylation of PYK2 in neurons. *J. Cell Sci.* 120, 3034-3044 (2007).
31. Sun, Y., Savanenin, A., Reddy, P. H. & Liu, Y. F. Polyglutamine-expanded huntingtin promotes sensitization of N-methyl-D-aspartate receptors via post-synaptic density 95. *J. Biol. Chem.* 276, 24713-24718 (2001).
32. Fan, J., et al. P38 MAPK is involved in enhanced NMDA receptor-dependent excitotoxicity in YAC transgenic mouse model of Huntington disease. *Neurobiol. Dis.* 45, 999-1009 (2012).
33. Brito, V., et al. Neurotrophin receptor p75(NTR) mediates Huntington's disease-associated synaptic and memory dysfunction. *J. Clin. Invest.* 124, 4411-4428 (2014).
34. Nithianantharajah, J., Barkus, C., Murphy, M. & Hannan, A. J. Gene-environment interactions modulating cognitive function and molecular correlates of synaptic plasticity in Huntington's disease transgenic mice. *Neurobiol. Dis.* 29, 490-504 (2008).
35. Miguez, A., et al. Fingolimod (FTY720) enhances hippocampal synaptic plasticity and memory in Huntington's disease by preventing p75NTR up-regulation and astrocyte-mediated inflammation. *Hum. Mol. Genet.* 24, 4958-4970 (2015).
36. Vonsattel, J. P., et al. Neuropathological classification of Huntington's disease. *J. Neuropathol. Exp. Neurol.* 44, 559-577 (1985).
37. Mangiarini, L., et al. Exon 1 of the HD gene with an expanded CAG repeat is sufficient to cause a progressive neurological phenotype in transgenic mice. *Cell* 87, 493-506 (1996).
38. Faure, C., Ramos, M. & Girault, J. A. Pyk2 cytonuclear localization: mechanisms and regulation by serine dephosphorylation. *Cell. Mol. Life Sci.* 70, 137-152 (2013).
39. Van Raamsdonk, J. M., Murphy, Z., Slow, E. J., Leavitt, B. R. & Hayden, M. R. Selective degeneration and nuclear localization of mutant huntingtin in the YAC128 mouse model of Huntington disease. *Hum. Mol. Genet.* 14, 3823-3835 (2005).
40. Prybylowski, K., et al. The synaptic localization of NR2B-containing NMDA receptors is controlled by interactions with PDZ proteins and AP-2. *Neuron* 47, 845-857 (2005).
41. Hallett, P. J., Spoelgen, R., Hyman, B. T., Standaert, D. G. & Dunah, A. W. Dopamine D1 activation potentiates striatal NMDA receptors by tyrosine phosphorylation-dependent subunit trafficking. *J. Neurosci.* 26, 4690-4700 (2006).
42. Köhr, G. & Seeburg, P. H. Subtype-specific regulation of recombinant NMDA receptor-channels by protein tyrosine kinases of the src family. *J. Physiol.* (Lond.) 492, 445-452 (1996).
43. Taniguchi, S., et al. Involvement of NMDAR2A tyrosine phosphorylation in depression-related behaviour. *EMBO J.* 28, 3717-3729 (2009).
44. Migaud, M., et al. Enhanced long-term potentiation and impaired learning in mice with mutant postsynaptic density-95 protein. *Nature* 396, 433-439 (1998).
45. Zhao, C., et al. The upregulation of NR2A-containing N-methyl-D-aspartate receptor function by tyrosine phosphorylation of postsynaptic density 95 via facilitating Src/proline-rich tyrosine kinase 2 activation. *Mol. Neurobiol.* 51, 500-511 (2015).
46. Yang, S., Roselli, F., Patchev, A. V., Yu, S. & Almeida, O. F. Non-receptor-tyrosine kinases integrate fast glucocorticoid signaling in hippocampal neurons. *J. Biol. Chem.* 288, 23725-23739 (2013).
47. Sturgill, J. F., Steiner, P., Czervionke, B. L. & Sabatini, B. L. Distinct domains within PSD-95 mediate synaptic 48. Frank, R. A., et al. NMDA receptors are selectively partitioned into complexes and supercomplexes during synapse maturation. *Nat. Commun.* 7, 11264 (2016).
49. Nada, S., et al. Identification of PSD-93 as a substrate for the Src family tyrosine kinase Fyn. *J. Biol. Chem.* 278, 47610-47621 (2003).
50. Sato, Y., Tao, Y. X., Su, Q. & Johns, R. A. Post-synaptic density-93 mediates tyrosine-phosphorylation of the N-methyl-D-aspartate receptors. *Neuroscience* 153, 700-708 (2008).
51. Tezuka, T., Umemori, H., Akiyama, T., Nakanishi, S. & Yamamoto, T. PSD-95 promotes Fyn-mediated tyrosine phosphorylation of the N-methyl-D-aspartate receptor subunit NR2A. *Proc. Natl. Acad. Sci. USA* 96, 435-440 (1999).
52. Corsi, J. M., et al. Autophosphorylation-independent and -dependent functions of focal adhesion kinase during development. *J. Biol. Chem.* 284, 34769-34776 (2009).
53. Zhao, X., Peng, X., Sun, S., Park, A. Y. & Guan, J. L. Role of kinase-independent and -dependent functions of FAK in endothelial cell survival and barrier function during embryonic development. *J. Cell Biol.* 189, 955-965 (2010).
54. Bongiorno-Borbone, L., et al. The translocation of focal adhesion kinase in brain synaptosomes is regulated by phosphorylation and actin assembly. *J. Neurochem.* 81, 1212-1222 (2002).
55. Regehr, W. G. Short-term presynaptic plasticity. *Cold Spring Harb. Perspect. Biol.* 4, a005702 (2012).
56. Zucker, R. S. Short-term synaptic plasticity. *Annu. Rev. Neurosci.* 12, 13-31 (1989).
57. Yang, S., Santos, M. D., Tang, C. M., Kim, J. G. & Yang, S. A Postsynaptic Role for Short-Term Neuronal Facilitation in Dendritic Spines. *Front. Cell. Neurosci.* 10, 224 (2016).
58. Bourgin, C., Murai, K. K., Richter, M. & Pasquale, E. B. The EphA4 receptor regulates dendritic spine remodeling by affecting beta1-integrin signaling pathways. *J. Cell Biol.* 178, 1295-1307 (2007).
59. Shi, Y., Pontrello, C. G., DeFea, K. A., Reichardt, L. F. & Ethell, I. M. Focal adhesion kinase acts downstream of EphB receptors to maintain mature dendritic spines by regulating cofilin activity. *J. Neurosci.* 29, 8129-8142 (2009).
60. Suo, L., Lu, H., Ying, G., Capecchi, M. R. & Wu, Q. Protocadherin clusters and cell adhesion kinase regulate dendrite complexity through Rho GTPase. *J. Mol. Cell. Biol.* 4, 362-376 (2012).
61. Kinoshita, Y., et al. Role for NUP62 depletion and PYK2 redistribution in dendritic retraction resulting from chronic stress. *Proc. Natl. Acad. Sci. USA* 111, 16130-16135 (2014).
62. Gladding, C. M., et al. Calpain and STriatal-Enriched protein tyrosine phosphatase (STEP) activation contribute to extrasynaptic NMDA receptor localization in a Huntington's disease mouse model. *Hum. Mol. Genet.* 21, 3739-3752 (2012).
63. Xu, J., et al. Striatal-enriched protein-tyrosine phosphatase (STEP) regulates Pyk2 kinase activity. *J. Biol. Chem.* 287, 20942-20956 (2012).
64. Xu, J., et al. Inhibitor of the tyrosine phosphatase STEP reverses cognitive deficits in a mouse model of Alzheimer's disease. *PLoS Biol.* 12, e1001923 (2014).
65. Dourlen, P., et al. Functional screening of Alzheimer risk loci identifies PTK2B as an in vivo modulator and early marker of Tau pathology. *Mol. Psychiatry* (2016).
66. Giralt, A., Carreton, O., Lao-Peregrin, C., Martin, E. D. & Alberch, J. Conditional BDNF release under pathological conditions improves Huntington's disease pathology by delaying neuronal dysfunction. *Mol. Neurodegener.* 6, 71 (2011).
67. Slot, J. W. & Geuze, H. J. Cryosectioning and immunolabeling. *Nat. Protoc.* 2, 2480-2491 (2007).
68. Prange, O., Wong, T. P., Gerrow, K., Wang, Y. T. & El-Husseini, A. A balance between excitatory and inhibitory synapses is controlled by PSD-95 and neuroligin. *Proc. Natl. Acad. Sci. USA* 101, 13915-13920 (2004).
69. Shao, C. Y., Sondhi, R., van de Nes, P. S. & Sacktor, T. C. PKMzeta is necessary and sufficient for synaptic clustering of PSD-95. *Hippocampus* 22, 1501-1507 (2012).
70. Marco, S., et al. Suppressing aberrant GluN3A expression rescues synaptic and behavioral impairments in Huntington's disease models. *Nature Medicine* 19, 1030-1038 (2013).

The invention claimed is:

1. A method of treating a neurodegenerative disease in a subject in need thereof comprising administering to the subject a therapeutically effective amount of a viral vector comprising a nucleic acid molecule encoding for a protein tyrosine kinase 2 beta (PYK2) polypeptide, wherein the viral vector is delivered by intracerebral injection, intravenous injection, intrathecal delivery, intracerebroventricular injection, or intra-nasal injection.

2. The method of claim 1 wherein the neurodegenerative disease is selected from the group consisting of Alzheimer's disease, amyotrophic lateral sclerosis (ALS) with frontotemporal dementia, inclusion body myopathy, frontotemporal dementia (IBMPFD), frontotemporal lobar degeneration, synucleopathies, Huntington's disease, amyloidopathies, angiopathies, tauopathies and Lewy bodies dementia.

3. The method of claim 2 wherein the neurodegenerative disease is Alzheimer's disease or Huntington's disease.

4. The method of claim 1, wherein the nucleic acid molecule encodes a PYK2 polypeptide comprising an amino acid sequence having at least 90% identity with the sequence as set forth in SEQ ID NO:1 or SEQ ID NO:2.

5. The method of claim 1, wherein the nucleic acid molecule comprises a sequence having at least 70% identity with the nucleic acid sequence as set forth in SEQ ID NO:3, or SEQ ID NO:4.

6. The method of claim 1 wherein the viral vector is an adeno-associated virus (AAV) vector.

7. The method of claim 6 wherein the AAV vector is a vector derived from an AAV serotype having tropism for and high transduction efficiencies in cells of the mammalian central and peripheral nervous system.

8. The method of claim 6 wherein the AAV vector is an AAV4, AAV9, AAVrh10, or an AAV10 vector.

9. The method of claim 1, wherein the nucleic acid molecule is operatively linked to a promoter sequence.

10. The method of claim 1, wherein the vector is delivered by intrathecal delivery.

11. The method of claim 7, wherein cells of the mammalian central and peripheral nervous system are neurons, neuronal progenitors, astrocytes, oligodendrocytes or glial cells.

* * * * *